US008685738B2

(12) United States Patent
Berka et al.

(10) Patent No.: US 8,685,738 B2
(45) Date of Patent: Apr. 1, 2014

(54) **METHODS OF OBTAINING GENETIC COMPETENCE IN *BACILLUS* CELLS**

(71) Applicant: Novozymes, Inc., Davis, CA (US)

(72) Inventors: Randy Berka, Davis, CA (US); Michelle Maranta, Davis, CA (US); Maria Tang, Fairfield, CA (US); Barbara Cherry, Winters, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/760,763

(22) Filed: Feb. 6, 2013

(65) Prior Publication Data

US 2013/0157309 A1 Jun. 20, 2013

Related U.S. Application Data

(63) Continuation of application No. 12/520,075, filed as application No. PCT/US2007/088186 on Dec. 19, 2007, now Pat. No. 8,389,283.

(60) Provisional application No. 60/877,053, filed on Dec. 21, 2006.

(51) Int. Cl.

| | |
|---|---|
| ***C12P 21/06*** | (2006.01) |
| ***C12N 1/21*** | (2006.01) |
| ***C12N 15/75*** | (2006.01) |

(52) U.S. Cl.
USPC ...................... 435/471; 435/69.1; 435/525.31

(58) Field of Classification Search
None
See application file for complete search history.

(56) References Cited

U.S. PATENT DOCUMENTS

2011/0262953 A1 10/2011 Collier et al.

FOREIGN PATENT DOCUMENTS

WO 0214490 A2 2/2002

OTHER PUBLICATIONS

Ashikaga 2000, J Bacteriol 182 (9), 2411-2415.
D'Souza 1994, Proc Natl Acad Sci USA 91, 9397-9401.
Hahn 1996, Mol Microbiol 21(4), 763-775.
Liu 1996, J Bacteriol 178 (17), 5144-515.
Kunst et al, 1997, Genbank Access No. NC_0009641.
Kunst et al, 1997, Genbank Access No. NP_388923.1.
D'Souza et al, 1994, Genbank Access No. U10926.1.
Anagnostopoulos et al., 1961, J Bacteriol 81, 741-746.
Avery et al 2005, Trends Microbiol 53, 217-244.
Berka et al 2002, Mol Microbiol 43 (5), 1331-134.
Blattner et al 1997, Science 277m 1453-1474.
Brzuszhierwicz et al 2006, Proc Natl Acad Sci USA 103, 12879-12884.
Dubnau et al 1999, Annual Rev Microbiol 53, 217-44.
Gwinn et al., 1964, J Bacteriol 87 (3), 519-526.
Hayashi et al 2006, Mol Sys Biol, 1-5.
Leonard et al 1964, J Bacteriol 88 (1), 220-225.
Perna et al 2001, Nature 409, 529-533.
Pragai et al 1994, Microbiol 140(2), 305-310.
Tangney et al 1994, Biotechnol Techniq 8, 463-466.
Thorne et al., 1966, J Bacteriol 91,1012-1020.
Turgay et al 1998m EMBO J 17, 6730-6738.
Velikonja et al 1994, Plasmid 31, 201-206.
Welch et al 2002, Proc Natl Acad Sci USA 99, 17020-17024.
Tortosa et al 2000, Molecular Microbiology 35(5), 1110-1119.

*Primary Examiner* — Nancy T Vogel
(74) *Attorney, Agent, or Firm* — Eric J. Fechter

(57) ABSTRACT

The present invention relates to methods of obtaining genetic competence in non-competent *Bacillus* cells for their transformation with exogenous DNA.

27 Claims, 24 Drawing Sheets

```
 M  F  Y  T  N  Q  P  A  I  N  C  T  T  Y  K  Q  M  L  R  S
ATGTTCTATACTAATCAACCAGCCATCAACTGCACTACATACAAACAAATGCTCCGCTCA    60

 T  G  S  L  S  N  L  F  S  E  S  D  S  P  Y  L  V  S  R  N
ACTGGTTCGCTATCCAATTTGTTCTCTGAAAGTGACTCGCCTTATTTGGTCTCAAGGAAT   120

 V  E  N  A  F  C  E  A  F  G  A  E  N  L  G  R  S  D  C  S
GTGGAAAATGCTTTTTGTGAAGCATTTGGAGCTGAAAACTTGGGGAGGTCAGACTGTTCT   180

 A  D  A  S  L  N  R  V  G  I  G  I  K  T  F  L  H  G  N  G
GCTGACGCTTCATTAAATCGTGTCGGAATTGGTATTAAGACTTTTCTTCATGGTAATGGT   240

 H  T  L  Q  K  V  A  E  F  N  K  D  S  D  L  Y  R  G  K  S
CATACTCTTCAAAAAGTAGCTGAATTCAATAAAGACTCAGACTTGTATCGTGGGAAATCT   300

 P  K  E  L  I  N  T  V  A  S  L  R  N  E  R  I  E  F  T  K
CCAAAAGAGCTAATAAACACGGTTGCTTCTCTCCGTAACGAGAGAATTGAATTTACTAAA   360

 R  T  Y  G  I  D  S  M  I  Y  H  C  V  T  R  K  P  G  K  I
AGAACATATGGTATTGATTCAATGATATACCACTGTGTAACAAGAAAGCCAGGGAAAATT   420

 L  I  F  E  E  P  M  D  L  V  E  I  S  S  I  T  N  V  K  V
CTTATTTTTGAAGAGCCAATGGACTTGGTTGAAATCTCCTCAATTACAAATGTGAAAGTA   480

 S  N  N  R  N  T  I  T  F  E  D  G  L  H  E  Y  S  F  N  V
AGTAACAACAGAAATACAATCACCTTTGAAGACGGTCTACACGAATACAGCTTTAATGTC   540

 T  K  S  T  L  Y  K  R  F  I  T  D  K  P  I  E  E  I  N  V
ACTAAGAGCACCCTTTATAAGCGTTTTATCACTGATAAACCTATTGAAGAAATTAATGTT   600
```

Fig 2A

```
 E  I  L  E  N  P  Y  H  E  L  A  K  L  F  G  F  E  I  P  K
GAAATCTTAGAAAATCCTTATCATGAATTGGCTAAACTATTTGGCTTTGAAATTCCAAAA     660

 I  P  A  P  T  V  N  P  F  E  N  L  E  H  V  I  L  P  L  F
ATTCCAGCACCAACTGTCAATCCTTTTGAAAACCTTGAGCACGTTATTCTTCCACTCTTT     720

 S  D  R  G  S  K  R  H  V  P  E  K  S  G  L  N  Q  W  N  A
TCAGACCGTGGCTCAAAGCGTCATGTACCAGAAAAAAGCGGTCTAAACCAATGGAATGCT     780

 L  G  R  P  R  N  P  N  E  I  Y  I  P  I  P  K  W  I  H  N
TTAGGTCGACCACGAAACCCTAACGAGATTTATATACCAATTCCAAAATGGATTCATAAT     840

 V  F  P  T  F  F  P  A  R  D  K  P  F  Q  L  R  L  P  D  K
GTATTCCCAACATTTTTCCCAGCTCGTGATAAACCTTTTCAGTTACGCTTGCCAGACAAA     900

 S  L  L  S  A  K  V  C  Q  D  N  S  K  A  L  M  S  N  P  N
TCGCTTTTATCAGCCAAGGTATGCCAAGACAATAGTAAAGCACTTATGTCTAATCCAAAT     960

 S  A  L  G  E  W  L  L  R  Q  V  M  N  L  E  E  K  E  L  L
AGTGCTCTTGGAGAATGGCTACTAAGACAAGTTATGAACTTAGAGGAAAAAGAACTTCTA     1020

 T  Y  E  M  L  E  R  L  N  I  D  S  V  I  V  Y  K  H  S  E
ACCTATGAAATGCTGGAAAGACTAAATATTGACTCAGTAATTGTTTATAAACACAGCGAA     1080

 Q  H  Y  S  I  D  F  C  E  M  G  S  Y  D  E  F  E  N  E  N
CAACATTACTCCATTGATTTTTGTGAAATGGGTTCTTATGATGAATTTGAAAATGAAAAC     1140

 K  *
AAATAA                                                           1146
```

Fig 2B

TCATGTTCCCATATTCTTTTAATGTTCCAATCCTTTTCCTCGTAATATTTATTAACTTCC 60
TTATCTCTTTTTTTATTTCTTTCGAGTTTTTTCTCCCAATATTCCGTATTACTTTTTGGT 120
ATATTCCCGTGTTTTTCACACGCATGCCAGAAACAAGAATCAATGAATATGACTATTTTA 180
TATTTCTGTATTACTATATCTGGACTACCGTATAATTTCTTAACATTTTTTCGGAATCTT 240
ATTCCACGGTGCCATAGTTCTTTAGTAACCTTATCTTCTAATTTTGAACGAGATTTGATT 300
GCCTGCATGTTTTTTCTTCTTTGTTCTTTTGAAACCGTGTCAGTCATAGAAGAGTCCTCC 360
AAAGCCACAATAATTGTATTCTATAAACGAGGAAGCAAGCCCTCAAGCTTACCCCCTCTT 420
AGTTCCTTTTTTGCCTACTTATTTATTTGTTTTCATTTTCAAATTCATCATAAGAACCCA 480
TTTCACAAAAATCAATGGAGTAATGTTGTTCGCTGTGTTTATAAACAATTACTGAGTCAA 540
TATTTAGTCTTTCCAGCATTTCATAGGTTAGAAGTTCTTTTTCCTCTAAGTTCATAACTT 600
GTCTTAGTAGCCATTCTCCAAGAGCACTATTTGGATTAGACATAAGTGCTTTACTATTGT 660
CTTGGCATACCTTGGCTGATAAAAGCGATTTGTCTGGCAAGCGTAACTGAAAAGGTTTAT 720
CACGAGCTGGGAAAAATGTTGGGAATACATTATGAATCCATTTTGGAATTGGTATATAAA 780
TCTCGTTAGGGTTTCGTGGTCGACCTAAAGCATTCCATTGGTTTAGACCGCTTTTTTCTG 840
GTACATGACGCTTTGAGCCACGGTCTGAAAAGAGTGGAAGAATAACGTGCTCAAGGTTTT 900
CAAAAGGATTGACAGTTGGTGCTGGAATTTTTGGAATTTCAAAGCCAAATAGTTTAGCCA 960
ATTCATGATAAGGATTTTCTAAGATTTCAACATTAATTTCTTCAATAGGTTTATCAGTGA 1020
TAAAACGCTTATAAAGGGTGCTCTTAGTGACATTAAAGCTGTATTCGTGTAGACCGTCTT 1080

Fig. 3A

| | |
|---|---|
| CAAAGGTGATTGTATTTCTGTTGTTACTTACTTTCACATTTGTAATTGAGGAGATTTCAA | 1140 |
| CCAAGTCCATTGGCTCTTCAAAAATAAGAATTTTCCCTGGCTTTCTTGTTACACAGTGGT | 1200 |
| ATATCATTGAATCAATACCATATGTTCTTTTAGTAAATTCAATTCTCTCGTTACGGAGAG | 1260 |
| AAGCAACCGTGTTTATTAGCTCTTTTGGAGATTTCCCACGATACAAGTCTGAGTCTTTAT | 1320 |
| TGAATTCAGCTACTTTTTGAAGAGTATGACCATTACCATGAAGAAAAGTCTTAATACCAA | 1380 |
| TTCCGACACGATTTAATGAAGCGTCAGCAGAACAGTCTGACCTCCCCAAGTTTTCAGCTC | 1440 |
| CAAATGCTTCACAAAAAGCATTTTCCACATTCCTTGAGACCAAATAAGGCGAGTCACTTT | 1500 |
| CAGAGAACAAATTGGATAGCGAACCAGTTGAGCGGAGCATTTGTTTGTATGTAGTGCAGT | 1560 |
| TGATGGCTGGTTGATTAGTATAGAACATTATTTTTCCTCCTCTTTTATGCTTGTCATTTC | 1620 |
| TTCTTTCAGACCCAAAAGGTAGTCAGCTGATACGTTCAATGTTTCAGCTATTCTTTTGAA | 1680 |
| AGTGTCCAATGATGGAGTTCTATTTTCACTTTCATATAGTGACCAAGTGCTTCTAGTGAC | 1740 |
| CCCGACTTTTTCAGCGATTTGGCTGGGTAATAACCTACGAGCTTCTCTTGCATTTTGAAT | 1800 |
| ACGATTTCCAAGGAAAGGTATCATTTTTGCACCTCCAAGATTTGTTGTTTTCAGAGTATC | 1860 |
| ACCAGAACCCCCGAAAATAGTCCAAAGTTAGCTAACAGCAAACAAATAAAAATAAATAAG | 1920 |
| TTGTTTACTCTTAGCAAACTTGTTACTAAAATTTGATAAAGTTATTCATTTAATCCAGCT | 1980 |
| CTTATGCTAAAATTGCATTAGCGGACAAGCTTAATGTTTGCAAGGAGGTATAATTTTGAC | 2040 |
| TTATCGAGTAGGTAGTATGTTTGCTGGGATAGGTGGAACTTGTTTAGGGTTTATCCAAGC | 2100 |
| TGGCGCTAGGATTGTCTGGGCAAATGAAATAGACAAAAATGCTTGTATTACTTATAGAAA | 2160 |
| TTATTTTGGGGATGCTTACTTACAAGAGGGTGACATTAACCTAATAGATAAAAACTCCAT | 2220 |

Fig. 3B

ACCTGAACTGGACATTTTGATTGGAGGTTTTCCTTGCCAAGCCTTCTCTATAGCTGGCTA 2280
TCGTAAAGGGTTTGAAGATGAAAGGGGAAACGTGTTCTTTCAAATATTAGAGGTATTGGA 2340
AGCACAAAGAAATGTTTATGGACACTTACCCCAAGCAATAATGCTTGAGAATGTAAAGAA 2400
CTTATTTACACATGATAGAGGTAATACGTACAGAGTAATAAAAGAGGCTTTGGAAGCCTT 2460
TGGTTATACCGTAAAAGCTGAGGTTCTTAATTCAATGGAATACGGTAACGTGCCACAAAA 2520
CAGAGAGCGGATTTATATTGTAGGTTTTCAAGATGAGAGCCAAGCTGAAAGGTTTAGCTT 2580
TCCAGACCCAATTCCTTTAACAAATCAACTTAATGATGTAATTGACCGAACTCGGAGAGT 2640
TGATAAAAGATATTATTATGATGAAACCTCTCAATATTATGATATGTTGCGAGAAGCCAT 2700
GGACAGTACAGATACAACTTATCAAATAAGACGTATATATGTTCGAGAAAATAGAAGCAA 2760
TGTTTGTCCTACACTGACAGCGAATATGGGAACTGGAGGGCATAATGTTCCTATTGTATT 2820
AGACTTTGAAAATAATATAAGAAAACTAACACCAGAAGAATGCTTACTATTGCAAGGTTT 2880
CCCAGCTGACTATCATTTTCCAGAAGGCATGGCAAACACTCACAAATATAAACAAGCTGG 2940
TAACTCTGTTACGGTGCCAGTTATAAGAAGAATTGCCACTAATATTATTAGCGTATTGAA 3000
CATTGGAATGAATATAAATCAAGAACATGAATATGCAATAGCTGAATAA 3049

Fig. 3C

```
B. lic.   1  MDRQNKAGFSLPKNATGIPFHPLSNG-CMPSIILKRTERATTCRLFSCWKAYLIRIA
     56
             |   |::|..|   .:.|..:|..:| |:.||.|.:..:|||..|:.||:
B. sub.   1  M---NRSGKHL---ISSIILYPRPSGECISSISLDKQTQATTSPLYFCWREK
     46
```

Amino acid sequence alignment of ComS proteins from *Bacillus licheniformis* (B. lic.) and *Bacillus subtilis* (B. sub.). Underlined residues in the *Bacillus subtilis* ComS sequence were found to be critical for biological activitiy (Ogura *et al.*, 1999, Mol. Microbiol. 32: 799-812).

Fig. 15

SEQUENCE LISTING

<160> NUMBER OF SEQ ID NOS: 71

<210> SEQ ID NO 1
<211> LENGTH: 141
<212> TYPE: DNA
<213> ORGANISM: Bacillus subtilis

<400> SEQUENCE: 1
ttgaaccgat caggcaagca tcttatcagc agcattatcc tgtatccccg gcccagcgga 60
gaatgtatat cctcaatcag cttggacaag caaacacaag ctacaacgtc cccgctgtac 120
ttctgctgga gggagaagta g 141

<210> SEQ ID NO 2
<211> LENGTH: 46
<212> TYPE: PRT
<213> ORGANISM: Bacillus subtilis

<400> SEQUENCE: 2

Met Asn Arg Ser Gly Lys His Leu Ile Ser Ser Ile Ile Leu Tyr Pro
1 5 10 15

Arg Pro Ser Gly Glu Cys Ile Ser Ser Ile Ser Leu Asp Lys Gln Thr
20 25 30

Gln Ala Thr Thr Ser Pro Leu Tyr Phe Cys Trp Arg Glu Lys
35 40 45

<210> SEQ ID NO 3
<211> LENGTH: 141
<212> TYPE: DNA
<213> ORGANISM: Bacillus subtilis var. natto

<400> SEQUENCE: 3
ttgaaccgat caggcaagca tcttatcagc tgcattatcc tgtatccccg gcccagcgga 60
gaatgtatat cctcaatcag cttggacaag caaacacaag ctacaacgtc cccgctgtac 120
ttctgctgga gggagaagta g 141

<210> SEQ ID NO 4
<211> LENGTH: 46
<212> TYPE: PRT
<213> ORGANISM: Bacillus amyloliquefaciens

<400> SEQUENCE: 4

Met Asn Arg Ser Asp Lys Arg Leu Ile Arg Ser Ile Ile Leu Phe Pro
1 5 10 15

Gln His Ser Ala Gly Cys Ile Ser Leu Ile Ser Ser Asp Arg Pro Ala
20 25 30

Arg Ala Thr Thr Ser Leu Leu Tyr Phe Cys Trp Lys Gly Gln
35 40 45

<210> SEQ ID NO 5
<211> LENGTH: 141
<212> TYPE: DNA
<213> ORGANISM: Bacillus amyloliquefaciens

<400> SEQUENCE: 5
ttgaaccgat ccgacaagcg ccttatcaga agcattatcc tgtttcctca gcacagcgca 60
ggatgtatat ccttaatcag ctcggacagg ccagcacgag ctacaacgtc cctgctgtac 120
ttttgctgga agggtcagta g 141

<210> SEQ ID NO 6
<211> LENGTH: 46
<212> TYPE: PRT
<213> ORGANISM: Bacillus subtilis subsp. natto

<400> SEQUENCE: 6

Met Asn Arg Ser Gly Lys His Leu Ile Ser Cys Ile Ile Leu Tyr Pro
1               5                   10                  15

Arg Pro Ser Gly Glu Cys Ile Ser Ser Ile Ser Leu Asp Lys Gln Thr
            20                  25                  30

Gln Ala Thr Thr Ser Pro Leu Tyr Phe Cys Trp Arg Glu Lys
        35                  40                  45

<210> SEQ ID NO 7
<211> LENGTH: 171
<212> TYPE: DNA
<213> ORGANISM: Bacillus licheniformis

<400> SEQUENCE: 7
atggacaggc agaacaaagc gggattcagc ctgccgaaaa acgcgactgg tatcccgttt 60
catccgctca gcaacggatg tatgccctcc atcatattga aaagaacgga acgggctaca 120
acatgccgtc tgttctcatg ctggaaggcg tacttgatac ggatcgctta a 171

<210> SEQ ID NO 8
<211> LENGTH: 56
<212> TYPE: PRT
<213> ORGANISM: Bacillus licheniformis

<400> SEQUENCE: 8

Met Asp Arg Gln Asn Lys Ala Gly Phe Ser Leu Pro Lys Asn Ala Thr
1               5                   10                  15

Gly Ile Pro Phe His Pro Leu Ser Asn Gly Cys Met Pro Ser Ile Ile
            20                  25                  30

Leu Lys Arg Thr Glu Arg Ala Thr Thr Cys Arg Leu Phe Ser Cys Trp
        35                  40                  45

Lys Ala Tyr Leu Ile Arg Ile Ala
    50                  55

<210> SEQ ID NO 9
<211> LENGTH: 171
<212> TYPE: DNA
<213> ORGANISM: Bacillus licheniformis

<400> SEQUENCE: 9
atggacaggc agaacaaagc gggattcagc ctgccgaaaa acgcgactgg tatcccgttt 60
catccgctca gcaacggatg tatgccctcc atcatattga aaagaacgga acgggctaca 120
acatgccgtc tgttctcatg ctggaaggcg tacttgatac ggatcgctta a 171

<210> SEQ ID NO 10
<211> LENGTH: 56
<212> TYPE: PRT
<213> ORGANISM: Bacillus licheniformis

<400> SEQUENCE: 10

Met Asp Arg Gln Asn Lys Ala Gly Phe Ser Leu Pro Lys Asn Ala Thr
1               5                   10                  15

Gly Ile Pro Phe His Pro Leu Ser Asn Gly Cys Met Pro Ser Ile Ile
            20                  25                  30

Leu Lys Arg Thr Glu Arg Ala Thr Thr Cys Arg Leu Phe Ser Cys Trp

```
        35                  40                  45

Lys Ala Tyr Leu Ile Arg Ile Ala
    50                  55


<210> SEQ ID NO 11
<211> LENGTH: 576
<212> TYPE: DNA
<213> ORGANISM: Bacillus subtilis

<400> SEQUENCE: 11

atgagccaga agaccgacgc ccccctggag agctacgagg tgaacggcgc caccatcgcc      60

gtgctgcccg aggagatcga cggcaagatc tgcagcaaga tcatcgagaa ggactgcgtg     120

ttctacgtga acatgaagcc cctgcagatc gtggacagaa gctgcagatt cttcggcagc     180

agctacgccg gcagaaaggc cggcacctac gaggtgacca agatcagcca caagcccccc     240

atcatggtgg accccagcaa ccagatcttc ctgttcccca ccctgagcag caccagaccc     300

cagtgcggct ggatcagcca cgtgcacgtg aaggagttca aggccaccga gttcgacgac     360

accgaggtga ccttcagcaa cggcaagacc atggagctgc ccatcagcta caacagcttc     420

gagaaccagg tgtacagaac cgcctggctg agaaccaagt tccaggacag aatcgaccac     480

agagtgccca agagacagga gttcatgctg taccccaagg aggagagaac caagatgatc     540

tacgacttca tcctgagaga gctgggcgag agatac                               576


<210> SEQ ID NO 12
<211> LENGTH: 192
<212> TYPE: PRT
<213> ORGANISM: Bacillus subtilis

<400> SEQUENCE: 12

Met Ser Gln Lys Thr Asp Ala Pro Leu Glu Ser Tyr Glu Val Asn Gly
1               5                   10                  15

Ala Thr Ile Ala Val Leu Pro Glu Glu Ile Asp Gly Lys Ile Cys Ser
            20                  25                  30

Lys Ile Ile Glu Lys Asp Cys Val Phe Tyr Val Asn Met Lys Pro Leu
        35                  40                  45

Gln Ile Val Asp Arg Ser Cys Arg Phe Phe Gly Ser Ser Tyr Ala Gly
    50                  55                  60

Arg Lys Ala Gly Thr Tyr Glu Val Thr Lys Ile Ser His Lys Pro Pro
65                  70                  75                  80

Ile Met Val Asp Pro Ser Asn Gln Ile Phe Leu Phe Pro Thr Leu Ser
                85                  90                  95

Ser Thr Arg Pro Gln Cys Gly Trp Ile Ser His Val His Val Lys Glu
            100                 105                 110

Phe Lys Ala Thr Glu Phe Asp Asp Thr Glu Val Thr Phe Ser Asn Gly
        115                 120                 125

Lys Thr Met Glu Leu Pro Ile Ser Tyr Asn Ser Phe Glu Asn Gln Val
    130                 135                 140

Tyr Arg Thr Ala Trp Leu Arg Thr Lys Phe Gln Asp Arg Ile Asp His
145                 150                 155                 160

Arg Val Pro Lys Arg Gln Glu Phe Met Leu Tyr Pro Lys Glu Glu Arg
                165                 170                 175

Thr Lys Met Ile Tyr Asp Phe Ile Leu Arg Glu Leu Gly Glu Arg Tyr
            180                 185                 190


<210> SEQ ID NO 13
<211> LENGTH: 579
```

-continued

<212> TYPE: DNA
<213> ORGANISM: Bacillus weihenstephanensis

<400> SEQUENCE: 13
atggagagca aggtggagag atacgtggag aactacgtgg tgagcaagaa caccatggcc 60
ctgctgcccg tggtgctggg cgagaagaag gtggtgacca gaatcgtgga gatggaggac 120
agcttcttcg tgttccagaa gcccctggac atcatcgaga gaagctgcag aaagcacggc 180
agcagcttct tcggcagaaa ggagggcacc aaggagctga ccagaatcac ccacaaggcc 240
cccatcgcca tcagccccac cgaccagctg tacttcttcc ccacctacag ctacagcaga 300
aaggagtgcg cctggctgag ccacttccac atcgaggaca acaaggagct gaaggacggc 360
aacctgatca tcagattcat caacggcttc gccgtgaagc tggagatgag caagagcagc 420
ttcgagaacc agcagaacag aaccgccaag ctgagaaccg agtacgagga cagaaagaag 480
aagcagggca acccctgctt caaggagatc gacaagaacg aggagagcaa gctgaccccc 540
gcctacgaga aggtgtactt cgtgaaggag ggcgaggtg 579

<210> SEQ ID NO 14
<211> LENGTH: 192
<212> TYPE: PRT
<213> ORGANISM: Bacillus licheniformis

<400> SEQUENCE: 14

Met Ser Thr Glu Asp Met Thr Lys Asp Thr Tyr Glu Val Asn Ser Ser
1 5 10 15

Thr Met Ala Val Leu Pro Leu Gly Glu Gly Glu Lys Pro Ala Ser Lys
20 25 30

Ile Leu Glu Thr Asp Arg Thr Phe Arg Val Asn Met Lys Pro Phe Gln
35 40 45

Ile Ile Glu Arg Ser Cys Arg Tyr Phe Gly Ser Ser Tyr Ala Gly Arg
50 55 60

Lys Ala Gly Thr Tyr Glu Val Ile Lys Val Ser His Lys Pro Pro Ile
65 70 75 80

Met Val Asp His Ser Asn Asn Ile Phe Leu Phe Pro Thr Phe Ser Ser
85 90 95

Thr Arg Pro Gln Cys Gly Trp Leu Ser His Ala His Val His Glu Phe
100 105 110

Cys Ala Ala Lys Tyr Asp Asn Thr Phe Val Thr Phe Val Asn Gly Glu
115 120 125

Thr Leu Glu Leu Pro Val Ser Ile Ser Ser Phe Glu Asn Gln Val Tyr
130 135 140

Arg Thr Ala Trp Leu Arg Thr Lys Phe Ile Asp Arg Ile Glu Gly Asn
145 150 155 160

Pro Met Gln Lys Lys Gln Glu Phe Met Leu Tyr Pro Lys Glu Asp Arg
165 170 175

Asn Gln Leu Ile Tyr Glu Phe Ile Leu Arg Glu Leu Lys Lys Arg Tyr
180 185 190

<210> SEQ ID NO 15
<211> LENGTH: 579
<212> TYPE: DNA
<213> ORGANISM: Bacillus sp.

<400> SEQUENCE: 15
atgaaccacc tggacatgca caagaagaga ctggtggagg agtacgagat caaccccagc 60
accatgatca tcctgcccca gatctacggc aagaagatct acagcagaat cttcgaggtg 120

```
gaggacgagt tcctgagccc cttcaagctg ttcgacatcg tgaagaagag ctgcggctac    180

ttcggcagca gctacgaggg cagaaaggac gccaccaagg acatcatcgg cgtgacccac    240

aaggtgccca tcgtgatcga ccccaccaac ctgctgtact tcttccccac caccagcccc    300

aacaaccccg actgcatctg gatcagctac gagcacatcg ccgcccacca cagaaccgac    360

cccagccaca ccaaggtggt gttcggcaac aagcacaccc tgatcctgcc cgtgagcagc    420

agcagcttcg agaaccagct gctgagaacc gcccacctga gaaccaagct gcaccagaga    480

atcgagggcc acggcagaaa gatgttctac ttcaccgaca accagagact gaacagagcc    540

agcgagcccg tgggcagcta cagaaacaga aagctggag                           579
```

<210> SEQ ID NO 16
<211> LENGTH: 192
<212> TYPE: PRT
<213> ORGANISM: Bacillus licheniformis

<400> SEQUENCE: 16

```
Met Ser Thr Glu Asp Met Thr Lys Asp Thr Tyr Glu Val Asn Ser Ser
1               5                   10                  15

Thr Met Ala Val Leu Pro Leu Gly Glu Gly Glu Lys Pro Ala Ser Lys
            20                  25                  30

Ile Leu Glu Thr Asp Arg Thr Phe Arg Val Asn Met Lys Pro Phe Gln
        35                  40                  45

Ile Ile Glu Arg Ser Cys Arg Tyr Phe Gly Ser Ser Tyr Ala Gly Arg
    50                  55                  60

Lys Ala Gly Thr Tyr Glu Val Ile Lys Val Ser His Lys Pro Pro Ile
65                  70                  75                  80

Met Val Asp His Ser Asn Asn Ile Phe Leu Phe Pro Thr Phe Ser Ser
                85                  90                  95

Thr Arg Pro Gln Cys Gly Trp Leu Ser His Ala His Val His Glu Phe
            100                 105                 110

Cys Ala Ala Lys Tyr Asp Asn Thr Phe Val Thr Phe Val Asn Gly Glu
        115                 120                 125

Thr Leu Glu Leu Pro Val Ser Ile Ser Ser Phe Glu Asn Gln Val Tyr
    130                 135                 140

Arg Thr Ala Trp Leu Thr Thr Lys Phe Ile Asp Arg Ile Glu Gly Asn
145                 150                 155                 160

Pro Met Gln Lys Lys Gln Glu Phe Met Leu Tyr Pro Lys Glu Asp Arg
                165                 170                 175

Asn Gln Leu Ile Tyr Glu Phe Ile Leu Arg Glu Leu Lys Lys Arg Tyr
            180                 185                 190
```

<210> SEQ ID NO 17
<211> LENGTH: 588
<212> TYPE: DNA
<213> ORGANISM: Bacillus cereus

<400> SEQUENCE: 17

```
atggacggca gagccgagag atacgtggag aactacgtga tcaacaagaa gaccatggcc     60

ctgctgcccg tgatcctggg cgagaagaac gtgatcacca gagtgatcga ggtggaggac    120

agcttcttca tgttccagaa gcccctggac atcgtggaga gaagctgcag aaagcacggc    180

agcagcttcc tgggcagaaa ggagggcacc aaggagctga ccagaatcac ccacaaggcc    240

cccatcgcca tcagccccac cgaccagctg tacttcttcc ccacctacag ctacagcaga    300

aaggagtgcg cctggctgag ccacttccac atcgccagca acaaggagct ggccgacggc    360
```

-continued

```
aacctgatca tcagattcat caacggcttc gccgtgaagc tggagatgag caagagcagc    420

ttcgagaacc agcagaacag aaccgccaag ctgagaaccg agtacgagga cagaaaggac    480

aagcagggca acctgcagtt caagcccgtg gccaaggagg ccatcagcac cctgagaccc    540

gcctacgaga aggtgtacct ggtgaaggag gaggacatcg agggcgag                 588


<210> SEQ ID NO 18
<211> LENGTH: 134
<212> TYPE: PRT
<213> ORGANISM: Bacillus sp.

<400> SEQUENCE: 18

Gly Glu Lys Pro Ala Ser Lys Ile Leu Glu Thr Asp Arg Thr Phe Arg
1               5                   10                  15

Val Asn Met Lys Pro Phe Gln Ile Ile Glu Arg Ser Cys Arg Tyr Phe
            20                  25                  30

Gly Ser Ser Tyr Ala Gly Arg Lys Ala Gly Thr Tyr Glu Val Ile Lys
        35                  40                  45

Val Ser His Lys Pro Pro Ile Met Val Asp His Ser Asn Asn Ile Phe
    50                  55                  60

Leu Phe Pro Thr Phe Ser Ser Thr Arg Pro Gln Cys Gly Trp Leu Ser
65                  70                  75                  80

His Ala His Val His Glu Phe Cys Ala Ala Lys Tyr Gly Asn Thr Phe
                85                  90                  95

Val Thr Phe Val Asn Gly Glu Thr Leu Glu Leu Pro Val Ser Ile Ser
            100                 105                 110

Ser Phe Glu Asn Gln Val Tyr Arg Thr Ala Trp Leu Arg Thr Lys Phe
        115                 120                 125

Ile Asp Arg Ile Glu Gly
    130


<210> SEQ ID NO 19
<211> LENGTH: 423
<212> TYPE: DNA
<213> ORGANISM: Bacillus sp.

<400> SEQUENCE: 19

aactacgtgg tgaacaagaa caccatggcc ctgctgccca tcatcctgag cgagaagaga     60

atcgtgacca gagtggtgga gatggaggac agcttcttcg tgttccagaa gcccctggac    120

atcatcgaga gaagctgcag aaagcacggc agcagcttcc tgggcagaaa ggagggcacc    180

aaggagctga cccacatcac ccacaaggcc cccatcgcca tcagccccac cgaccagctg    240

tacttcttcc ccacctacag ctacagcaga aaggagtgcg cctggctgag ccacttctac    300

atcgagagca acaaggagag caaggacggc aacgtgatcg tgagattcat caacggcttc    360

gccgtgaagc tggagatcag caagagcagc ttcgagaacc agctgaacag aaccgccaag    420

ctg                                                                  423


<210> SEQ ID NO 20
<211> LENGTH: 193
<212> TYPE: PRT
<213> ORGANISM: Bacillus weihenstephanensis

<400> SEQUENCE: 20

Met Glu Ser Lys Val Glu Arg Tyr Val Glu Asn Tyr Val Val Ser Lys
1               5                   10                  15

Asn Thr Met Ala Leu Leu Pro Val Val Leu Gly Glu Lys Lys Val Val
```

```
            20                  25                  30

Thr Arg Ile Val Glu Met Glu Asp Ser Phe Phe Val Phe Gln Lys Pro
        35                  40                  45

Leu Asp Ile Ile Glu Arg Ser Cys Arg Lys His Gly Ser Ser Phe Phe
    50                  55                  60

Gly Arg Lys Glu Gly Thr Lys Glu Leu Thr Arg Ile Thr His Lys Ala
65                  70                  75                  80

Pro Ile Ala Ile Ser Pro Thr Asp Gln Leu Tyr Phe Phe Pro Thr Tyr
                85                  90                  95

Ser Tyr Ser Arg Lys Glu Cys Ala Trp Leu Ser His Phe His Ile Glu
            100                 105                 110

Asp Asn Lys Glu Leu Lys Asp Gly Asn Leu Ile Ile Arg Phe Ile Asn
        115                 120                 125

Gly Phe Ala Val Lys Leu Glu Met Ser Lys Ser Ser Phe Glu Asn Gln
    130                 135                 140

Gln Asn Arg Thr Ala Lys Leu Arg Thr Glu Tyr Glu Asp Arg Lys Lys
145                 150                 155                 160

Lys Gln Gly Asn Pro Cys Phe Lys Glu Ile Asp Lys Asn Glu Glu Ser
                165                 170                 175

Lys Leu Thr Pro Ala Tyr Glu Lys Val Tyr Phe Val Lys Glu Gly Glu
            180                 185                 190

Val
```

<210> SEQ ID NO 21
<211> LENGTH: 423
<212> TYPE: DNA
<213> ORGANISM: Bacillus sp.

<400> SEQUENCE: 21

```
aactacgtgg tgaccaagaa caccatggcc ctgctgcccg tgatcctgag cgagaagaag      60

atcgccacca gagtggtgga gatgaacgac agcttcttcg tgttccagaa gcccctggac     120

atcatcgaga gaagctgcag aaagcacggc agcagcttcc tgggcagaaa ggagggcacc     180

aaggagctga cccacatcac ccacaaggcc cccatcgcca tcagccccgc cgaccagctg     240

tacttcttcc ccacctacag ctacagcaga aaggagtgcg cctggctgag ccacttctac     300

atcgagagca acaaggagct gaaggacggc aacctgatca tcagattcat caacggcttc     360

gccgtgaagc tggagatcag caagaccagc ttcgagaacc agcagaacag aaccgccaag     420

ctg                                                                   423
```

<210> SEQ ID NO 22
<211> LENGTH: 193
<212> TYPE: PRT
<213> ORGANISM: Bacillus thuringiensis

<400> SEQUENCE: 22

```
Met Glu Asn Lys Val Glu Arg Tyr Val Glu Asn Tyr Val Val Asn Lys
1               5                   10                  15

Asn Thr Met Ala Leu Leu Pro Val Ile Leu Ser Glu Lys Lys Ile Val
            20                  25                  30

Thr Arg Val Val Glu Val Gln Asp Ser Phe Phe Val Phe Gln Lys Pro
        35                  40                  45

Leu Asp Ile Ile Glu Arg Ser Cys Arg Lys His Gly Ser Ser Phe Leu
    50                  55                  60

Gly Arg Lys Glu Gly Thr Lys Glu Leu Thr His Ile Thr His Lys Ala
65                  70                  75                  80
```

-continued

Pro Ile Ala Ile Ser Pro Thr Asp Gln Leu Tyr Phe Phe Pro Thr Tyr
85 90 95

Ser Tyr Ser Arg Lys Glu Cys Ala Trp Leu Ser His Phe Tyr Ile Glu
100 105 110

Ser Asn Lys Glu Leu Lys Asp Gly Asn Leu Ile Ile Arg Phe Ile Asn
115 120 125

Gly Phe Ala Val Lys Leu Glu Ile Ser Lys Thr Ser Phe Glu Asn Gln
130 135 140

Gln Asn Arg Thr Ala Lys Leu Arg Thr Glu Tyr Glu Asp Arg Arg Lys
145 150 155 160

Lys Gln Gly Asn Pro Cys Phe Lys Glu Val Asp Gln Arg Asp Glu Ser
165 170 175

Thr Leu Arg Pro Ala Tyr Glu Arg Val Tyr Val Val Arg Glu Glu Asp
180 185 190

Val

<210> SEQ ID NO 23
<211> LENGTH: 423
<212> TYPE: DNA
<213> ORGANISM: Bacillus sp.

<400> SEQUENCE: 23
aactacgtgg tgaacaagaa caccatggcc ctgctgcccg tgatcctgag cgagaagaag 60
atcgtgacca gagtggtgga gatgggcgac agcttcttcg tgttccagga gcccctggac 120
atcatcgaga gaagctgcag aaagcacggc agcagcttcc tgggcagaaa ggagggcacc 180
aaggagctga cccacatcac ccacaaggcc cccatcgcca tcagccccac cgaccagctg 240
tacttcttcc ccacctacag ctacagcaga aaggagtgcg cctggctgag ccacttctac 300
atcgagagca acaaggagag caaggacggc aacgtgatca tcagattcat caacggcttc 360
gccgtgaagc tggagatcag caagagcagc ttcgagaacc agctgaacag aaccgccaag 420
ctg 423

<210> SEQ ID NO 24
<211> LENGTH: 193
<212> TYPE: PRT
<213> ORGANISM: Bacillus cereus

<400> SEQUENCE: 24

Met Glu Ser Lys Val Glu Arg Tyr Val Glu Asn Tyr Val Val Asn Lys
1 5 10 15

Asn Thr Met Ala Leu Leu Pro Val Ile Leu Ser Glu Lys Lys Ile Val
20 25 30

Thr Arg Val Val Glu Val Gln Asp Ser Phe Phe Val Phe Gln Lys Pro
35 40 45

Leu Asp Ile Ile Glu Arg Ser Cys Arg Lys His Gly Ser Ser Phe Leu
50 55 60

Gly Arg Lys Glu Gly Thr Lys Glu Leu Thr His Ile Thr His Lys Ala
65 70 75 80

Pro Ile Ala Ile Ser Pro Thr Asp Gln Leu Tyr Phe Phe Pro Thr Tyr
85 90 95

Ser Tyr Ser Arg Lys Glu Cys Ala Trp Leu Ser His Phe Tyr Ile Glu
100 105 110

Ser Asn Lys Glu Leu Lys Asp Gly Asn Leu Ile Ile Arg Phe Ile Asn
115 120 125

Gly Phe Ala Val Lys Leu Glu Ile Ser Lys Thr Ser Phe Glu Asn Gln
    130                 135                 140

Gln Asn Arg Thr Ala Lys Leu Arg Thr Glu Tyr Glu Asp Arg Arg Lys
145                 150                 155                 160

Lys Gln Gly Asn Pro Cys Phe Lys Glu Val Asp Gln Arg Asp Glu Ser
                165                 170                 175

Thr Leu Arg Pro Ala Tyr Glu Lys Val Tyr Phe Val Arg Glu Glu Asp
            180                 185                 190

Leu

<210> SEQ ID NO 25
<211> LENGTH: 423
<212> TYPE: DNA
<213> ORGANISM: Bacillus sp.

<400> SEQUENCE: 25
aactacgtgg tgaccaagaa caccatggcc ctgctgcccg tgatcctgag cgagaagaag      60
atcgtgacca gagtggtgga gatgaacgac agcttcttcg tgttccagaa gcccctggac     120
atcatcgaga gaagctgcag aaagaacggc agcagcttcc tgggcagaaa ggagggcacc     180
aaggagctga cccacatcac ccacaaggcc cccatcgcca tcagccccgc cgaccagctg     240
tacttcttcc ccacctacag ctacagcaga aaggagtgcg cctggctgag ccacttctac     300
atcgagagca acaaggagct gaaggacggc aacctgatca tcagattcat caacggcttc     360
gccgtgaagc tggagatcag caagaccagc ttcgagaacc agcagaacag aaccgccaag     420
ctg                                                                   423

<210> SEQ ID NO 26
<211> LENGTH: 193
<212> TYPE: PRT
<213> ORGANISM: Bacillus cereus

<400> SEQUENCE: 26

Met Glu Asn Lys Val Glu Arg Tyr Val Glu Asn Tyr Val Val Asn Lys
1               5                   10                  15

Asn Thr Met Ala Leu Leu Pro Val Ile Leu Ser Glu Lys Lys Ile Val
            20                  25                  30

Thr Arg Val Val Glu Val Gln Asp Ser Phe Phe Val Phe Gln Lys Pro
        35                  40                  45

Leu Asp Ile Ile Glu Arg Ser Cys Arg Lys His Gly Ser Ser Phe Leu
    50                  55                  60

Gly Arg Lys Glu Gly Thr Lys Glu Leu Thr His Ile Thr His Lys Ala
65                  70                  75                  80

Pro Ile Ala Ile Ser Pro Thr Asp Gln Leu Tyr Phe Phe Pro Thr Tyr
                85                  90                  95

Ser Tyr Ser Arg Lys Glu Cys Ala Trp Leu Ser His Phe Tyr Ile Glu
            100                 105                 110

Ser Asn Lys Glu Leu Lys Asp Gly Asn Leu Ile Ile Arg Phe Ile Asn
        115                 120                 125

Gly Phe Ala Val Lys Leu Glu Ile Ser Lys Thr Ser Phe Glu Asn Gln
    130                 135                 140

Gln Asn Arg Thr Ala Lys Leu Arg Thr Glu Tyr Glu Asp Arg Arg Lys
145                 150                 155                 160

Lys Gln Gly Asn Pro Cys Phe Lys Glu Val Asp Lys Lys Glu Glu Ser
                165                 170                 175

Arg Leu Lys Pro Ala Tyr Glu Ser Val Tyr Phe Val Lys Glu Glu Glu 180 185 190

Val

<210> SEQ ID NO 27
<211> LENGTH: 423
<212> TYPE: DNA
<213> ORGANISM: Bacillus sp.

<400> SEQUENCE: 27
aactacgtgg tgaacaagaa caccatggcc ctgctgcccg tgatcctgag cgagaagaag 60
atcgtgacca gagtggtgga gatggaggac agcttcttcg tgttccagaa gcccctggac 120
atcatcgaga gaagctgcag aaagcacggc agcagcttcc tgggcagaaa ggagggcacc 180
aaggagctga cccacatcac ccacaaggcc cccatcgcca tcagccccgc cgaccagttc 240
tacttcttcc ccacctacag ctacagcaga aaggagtgcg cctggctgag ccacttctac 300
atcgagagca acaaggagct gaaggacggc aacgtgatcg tgagattcat caacggcttc 360
gccgtgaagc tggagatcag caagagcagc agcgagaacc agctgaacag aaccgccaag 420
ctg 423

<210> SEQ ID NO 28
<211> LENGTH: 193
<212> TYPE: PRT
<213> ORGANISM: Bacillus cereus

<400> SEQUENCE: 28

Met Glu Ser Lys Val Glu Arg Tyr Val Glu Asn Tyr Val Val Asn Lys
1 5 10 15

Asn Thr Met Ala Leu Leu Pro Ile Ile Leu Ser Glu Lys Lys Ile Val
20 25 30

Thr Arg Val Val Glu Val Gln Asp Ser Phe Phe Val Phe Gln Lys Pro
35 40 45

Leu Asp Ile Ile Glu Arg Ser Cys Arg Lys His Gly Ser Ser Phe Leu
50 55 60

Gly Arg Lys Glu Gly Thr Lys Glu Leu Thr His Ile Thr His Lys Ala
65 70 75 80

Pro Ile Ala Ile Ser Pro Thr Asp Gln Leu Tyr Phe Phe Pro Thr Tyr
85 90 95

Ser Tyr Ser Arg Lys Glu Cys Ala Trp Leu Ser His Phe Tyr Ile Glu
100 105 110

Asn Asn Lys Glu Leu Lys Asp Gly Asn Leu Ile Ile Arg Phe Ile Asn
115 120 125

Gly Phe Ala Val Lys Leu Glu Ile Ser Lys Thr Ser Phe Glu Asn Gln
130 135 140

Gln Asn Arg Thr Ala Lys Leu Arg Thr Glu Tyr Glu Asp Arg Arg Lys
145 150 155 160

Lys Gln Gly Asn Pro Cys Phe Lys Glu Ile Asp Lys Ser Glu Glu Ser
165 170 175

Thr Leu Arg Pro Ala Tyr Glu Lys Val Tyr Val Val Arg Glu Glu Glu
180 185 190

Val

<210> SEQ ID NO 29
<211> LENGTH: 423
<212> TYPE: DNA
<213> ORGANISM: Bacillus sp.

<400> SEQUENCE: 29
aactacgtgg tgaacaagaa caccatggcc ctgctgagcg tgatcctgag cgagaagaag 60
atcgtgacca gagtggtgga gatgggcgac agcttcttcg tgttccagaa gcccctggac 120
atcatcgaga gaagctgcag aaagcacggc agcagcttcc tgggcagaaa ggagggcacc 180
aaggagctga cccacatcac ccacaaggcc cccatcgcca tcagccccac cgaccagctg 240
tacttcttcc ccacctacag ctacagcaga aaggagtgcg cctggctgag ccacttctac 300
atcgagagca acaaggagag caaggacggc aacgtgatca tcagattcat caacggcttc 360
gccgtgaagc tggagatcag caagagcagc ttcgagaacc agctgaacag aaccgccaag 420
ctg 423

<210> SEQ ID NO 30
<211> LENGTH: 193
<212> TYPE: PRT
<213> ORGANISM: Bacillus cereus

<400> SEQUENCE: 30

Met Glu Asn Lys Val Glu Arg Tyr Val Glu Asn Tyr Val Val Asn Lys
1               5                   10                  15

Asn Thr Met Ala Leu Leu Pro Val Ile Leu Ser Glu Lys Lys Ile Val
            20                  25                  30

Thr Arg Val Val Glu Val Gln Asp Ser Phe Phe Val Phe Gln Lys Pro
        35                  40                  45

Leu Asp Ile Ile Glu Arg Ser Cys Arg Lys His Gly Ser Ser Phe Leu
    50                  55                  60

Gly Arg Lys Glu Gly Thr Lys Glu Leu Thr His Ile Thr His Lys Ala
65                  70                  75                  80

Pro Ile Ala Ile Ser Pro Thr Asp Gln Leu Tyr Phe Phe Pro Thr Tyr
                85                  90                  95

Ser Tyr Ser Arg Lys Glu Cys Ala Trp Leu Ser His Phe Tyr Ile Glu
            100                 105                 110

Ser Asn Lys Glu Leu Lys Asp Gly Asn Leu Ile Ile Arg Phe Ile Asn
        115                 120                 125

Gly Phe Ala Val Lys Leu Glu Ile Ser Lys Thr Ser Phe Glu Asn Gln
    130                 135                 140

Gln Asn Arg Thr Ala Lys Leu Arg Thr Glu Tyr Glu Asp Arg Arg Lys
145                 150                 155                 160

Lys Gln Gly Asn Pro Cys Phe Lys Glu Val Asp Lys Asn Glu Glu Ser
                165                 170                 175

Arg Leu Lys Pro Ala Tyr Glu Ser Val Tyr Phe Val Lys Glu Glu Glu
            180                 185                 190

Val

<210> SEQ ID NO 31
<211> LENGTH: 402
<212> TYPE: DNA
<213> ORGANISM: Bacillus sp.

<400> SEQUENCE: 31
ggcgagaagc ccgccagcaa gatcctggag accgacagaa ccttcagagt gaacatgaag 60
cccttccaga tcatcgagag aagctgcaga tacttcggca gcagctacgc cggcagaaag 120
gccggcacct acgaggtgat caaggtgagc cacaagcccc ccatcatggt ggaccacagc 180
aacaacatct tcctgttccc caccttcagc agcaccagac cccagtgcgg ctggctgagc 240

```
cacgcccacg tgcacgagtt ctgcgccgcc aagtacggca acaccttcgt gaccttcgtg    300

aacggcgaga ccctggagct gcccgtgagc atcagcagct tcgagaacca ggtgtacaga    360

accgcctggc tgagaaccaa gttcatcgac agaatcgagg gc                      402


<210> SEQ ID NO 32
<211> LENGTH: 193
<212> TYPE: PRT
<213> ORGANISM: Bacillus cereus

<400> SEQUENCE: 32

Met Glu Ser Lys Val Glu Arg Tyr Val Glu Asn Tyr Val Val Thr Lys
1               5                   10                  15

Asn Thr Met Ala Leu Leu Pro Val Ile Leu Ser Glu Lys Lys Ile Val
            20                  25                  30

Thr Arg Val Val Glu Met Asn Asp Ser Phe Phe Val Phe Gln Lys Pro
        35                  40                  45

Leu Asp Ile Ile Glu Arg Ser Cys Arg Lys His Gly Ser Ser Phe Leu
    50                  55                  60

Gly Arg Lys Glu Gly Thr Lys Glu Leu Thr His Ile Thr His Lys Ala
65                  70                  75                  80

Pro Ile Ala Ile Ser Pro Ala Asp Gln Leu Tyr Phe Phe Pro Thr Tyr
                85                  90                  95

Ser Tyr Ser Arg Lys Glu Cys Ala Trp Leu Ser His Phe Tyr Ile Glu
            100                 105                 110

Ser Asn Lys Glu Leu Lys Asp Gly Asn Leu Ile Ile Arg Phe Ile Asn
        115                 120                 125

Gly Phe Ala Val Lys Leu Glu Ile Ser Lys Thr Ser Phe Glu Asn Gln
    130                 135                 140

Gln Asn Arg Thr Ala Lys Leu Arg Thr Glu Tyr Glu Asp Arg Arg Lys
145                 150                 155                 160

Lys Gln Gly Asn Pro Cys Phe Lys Glu Val Asp Lys Lys Glu Glu Ser
                165                 170                 175

Thr Leu Arg Pro Ala Tyr Glu Ser Val Tyr Phe Val Lys Glu Gly Glu
            180                 185                 190

Val


<210> SEQ ID NO 33
<211> LENGTH: 504
<212> TYPE: DNA
<213> ORGANISM: Bacillus thuringiensis

<400> SEQUENCE: 33

atgaacgacg agaacaacat catcatcagc agcagcacca tgatgctggt gccctacaac     60

cacccctact acagaaccaa gatcatcgac agcagcggca acgacctgtg cagctgccag    120

accgccctgc agctgatcaa gaagagctgc ctgacccaga tccacagcac ctaccagggc    180

agaagaaacg ccgtgcagac caacttcaga ttcaagcaga acgtgcccat ccccatcaac    240

cacagagagt acatctgcac cttccccacc gagagcccca gcagccccaa ctgcatctgg    300

ctgttctaca accacatcca cgacatcgag ttctgccaga agatcaagga ggccaagatc    360

cacttcagca acggcaccac caccaccatc agcatcagcc cccacaagct gcagcagcag    420

ctgctgaagg ccggctacat cctgagcaga atgaacatgc aggacagcct gcagttcaag    480

aacccccctgc tgcacctgct gcac                                         504


<210> SEQ ID NO 34
```

```
<211> LENGTH: 196
<212> TYPE: PRT
<213> ORGANISM: Bacillus cereus

<400> SEQUENCE: 34

Met Asp Gly Arg Ala Glu Arg Tyr Val Glu Asn Tyr Val Ile Asn Lys
1               5                   10                  15

Lys Thr Met Ala Leu Leu Pro Val Ile Leu Gly Glu Lys Asn Val Ile
            20                  25                  30

Thr Arg Val Ile Glu Val Glu Asp Ser Phe Phe Met Phe Gln Lys Pro
        35                  40                  45

Leu Asp Ile Val Glu Arg Ser Cys Arg Lys His Gly Ser Ser Phe Leu
    50                  55                  60

Gly Arg Lys Glu Gly Thr Lys Glu Leu Thr Arg Ile Thr His Lys Ala
65                  70                  75                  80

Pro Ile Ala Ile Ser Pro Thr Asp Gln Leu Tyr Phe Phe Pro Thr Tyr
                85                  90                  95

Ser Tyr Ser Arg Lys Glu Cys Ala Trp Leu Ser His Phe His Ile Ala
            100                 105                 110

Ser Asn Lys Glu Leu Ala Asp Gly Asn Leu Ile Ile Arg Phe Ile Asn
        115                 120                 125

Gly Phe Ala Val Lys Leu Glu Met Ser Lys Ser Ser Phe Glu Asn Gln
    130                 135                 140

Gln Asn Arg Thr Ala Lys Leu Arg Thr Glu Tyr Glu Asp Arg Lys Asp
145                 150                 155                 160

Lys Gln Gly Asn Leu Gln Phe Lys Pro Val Ala Lys Glu Ala Ile Ser
                165                 170                 175

Thr Leu Arg Pro Ala Tyr Glu Lys Val Tyr Leu Val Lys Glu Glu Asp
            180                 185                 190

Ile Glu Gly Glu
        195


<210> SEQ ID NO 35
<211> LENGTH: 579
<212> TYPE: DNA
<213> ORGANISM: Bacillus cereus

<400> SEQUENCE: 35

atggagagca aggtggagag atacgtggag aactacgtgg tgaacaagaa caccatggcc      60

ctgctgccca tcatcctgag cgagaagaag atcgtgacca gagtggtgga ggtgcaggac     120

agcttcttcg tgttccagaa gcccctggac atcatcgaga gaagctgcag aaagcacggc     180

agcagcttcc tgggcagaaa ggagggcacc aaggagctga cccacatcac ccacaaggcc     240

cccatcgcca tcagccccac cgaccagctg tacttcttcc ccacctacag ctacagcaga     300

aaggagtgcg cctggctgag ccacttctac atcgagaaca acaaggagct gaaggacggc     360

aacctgatca tcagattcat caacggcttc gccgtgaagc tggagatcag caagaccagc     420

ttcgagaacc agcagaacag aaccgccaag ctgagaaccg agtacgagga cagaagaaag     480

aagcagggca acccctgctt caaggagatc gacaagagcg aggagagcac cctgagaccc     540

gcctacgaga aggtgtacgt ggtgagagag gaggaggtg                            579


<210> SEQ ID NO 36
<211> LENGTH: 193
<212> TYPE: PRT
<213> ORGANISM: Bacillus sp.

<400> SEQUENCE: 36
```

-continued

Met Asn His Leu Asp Met His Lys Lys Arg Leu Val Glu Glu Tyr Glu
1 5 10 15

Ile Asn Pro Ser Thr Met Ile Ile Leu Pro Gln Ile Tyr Gly Lys Lys
20 25 30

Ile Tyr Ser Arg Ile Phe Glu Val Glu Asp Glu Phe Leu Ser Pro Phe
35 40 45

Lys Leu Phe Asp Ile Val Lys Lys Ser Cys Gly Tyr Phe Gly Ser Ser
50 55 60

Tyr Glu Gly Arg Lys Asp Ala Thr Lys Asp Ile Ile Gly Val Thr His
65 70 75 80

Lys Val Pro Ile Val Ile Asp Pro Thr Asn Leu Leu Tyr Phe Phe Pro
85 90 95

Thr Thr Ser Pro Asn Asn Pro Asp Cys Ile Trp Ile Ser Tyr Glu His
100 105 110

Ile Ala Ala His His Arg Thr Asp Pro Ser His Thr Lys Val Val Phe
115 120 125

Gly Asn Lys His Thr Leu Ile Leu Pro Val Ser Ser Ser Ser Phe Glu
130 135 140

Asn Gln Leu Leu Arg Thr Ala His Leu Arg Thr Lys Leu His Gln Arg
145 150 155 160

Ile Glu Gly His Gly Arg Lys Met Phe Tyr Phe Thr Asp Asn Gln Arg
165 170 175

Leu Asn Arg Ala Ser Glu Pro Val Gly Ser Tyr Arg Asn Arg Lys Leu
180 185 190

Glu

<210> SEQ ID NO 37
<211> LENGTH: 579
<212> TYPE: DNA
<213> ORGANISM: Bacillus cereus

<400> SEQUENCE: 37
atggagaaca aggtggagag atacgtggag aactacgtgg tgaacaagaa caccatggcc 60
ctgctgcccg tgatcctgag cgagaagaag atcgtgacca gagtggtgga ggtgcaggac 120
agcttcttcg tgttccagaa gcccctggac atcatcgaga gaagctgcag aaagcacggc 180
agcagcttcc tgggcagaaa ggagggcacc aaggagctga cccacatcac ccacaaggcc 240
cccatcgcca tcagccccac cgaccagctg tacttcttcc ccacctacag ctacagcaga 300
aaggagtgcg cctggctgag ccacttctac atcgagagca acaaggagct gaaggacggc 360
aacctgatca tcagattcat caacggcttc gccgtgaagc tggagatcag caagaccagc 420
ttcgagaacc agcagaacag aaccgccaag ctgagaaccg agtacgagga cagaagaaag 480
aagcagggca acccctgctt caaggaggtg gacaagaagg aggagagcag actgaagccc 540
gcctacgaga gcgtgtactt cgtgaaggag gaggaggtg 579

<210> SEQ ID NO 38
<211> LENGTH: 141
<212> TYPE: PRT
<213> ORGANISM: Bacillus sp.

<400> SEQUENCE: 38

Asn Tyr Val Val Asn Lys Asn Thr Met Ala Leu Leu Pro Ile Ile Leu
1 5 10 15

Ser Glu Lys Arg Ile Val Thr Arg Val Val Glu Met Glu Asp Ser Phe
20 25 30

```
Phe Val Phe Gln Lys Pro Leu Asp Ile Ile Glu Arg Ser Cys Arg Lys
        35                  40                  45

His Gly Ser Ser Phe Leu Gly Arg Lys Glu Gly Thr Lys Glu Leu Thr
    50                  55                  60

His Ile Thr His Lys Ala Pro Ile Ala Ile Ser Pro Thr Asp Gln Leu
65                  70                  75                  80

Tyr Phe Phe Pro Thr Tyr Ser Tyr Ser Arg Lys Glu Cys Ala Trp Leu
                85                  90                  95

Ser His Phe Tyr Ile Glu Ser Asn Lys Glu Ser Lys Asp Gly Asn Val
            100                 105                 110

Ile Val Arg Phe Ile Asn Gly Phe Ala Val Lys Leu Glu Ile Ser Lys
        115                 120                 125

Ser Ser Phe Glu Asn Gln Leu Asn Arg Thr Ala Lys Leu
    130                 135                 140


<210> SEQ ID NO 39
<211> LENGTH: 576
<212> TYPE: DNA
<213> ORGANISM: Bacillus licheniformis

<400> SEQUENCE: 39

atgagcaccg aggacatgac caaggacacc tacgaggtga acagcagcac catggccgtg      60

ctgcccctgg gcgagggcga gaagcccgcc agcaagatcc tggagaccga cagaaccttc     120

agagtgaaca tgaagccctt ccagatcatc gagagaagct gcagatactt cggcagcagc     180

tacgccggca gaaaggccgg cacctacgag gtgatcaagg tgagccacaa gcccccccatc    240

atggtggacc acagcaacaa catcttcctg ttccccacct tcagcagcac cagaccccag     300

tgcggctggc tgagccacgc ccacgtgcac gagttctgcg ccgccaagta cgacaacacc     360

ttcgtgacct tcgtgaacgg cgagaccctg gagctgcccg tgagcatcag cagcttcgag     420

aaccaggtgt acagaaccgc ctggctgaga accaagttca tcgacagaat cgagggcaac     480

cccatgcaga agaagcagga gttcatgctg taccccaagg aggacagaaa ccagctgatc     540

tacgagttca tcctgagaga gctgaagaag agatac                               576


<210> SEQ ID NO 40
<211> LENGTH: 141
<212> TYPE: PRT
<213> ORGANISM: Bacillus sp.

<400> SEQUENCE: 40

Asn Tyr Val Val Asn Lys Asn Thr Met Ala Leu Leu Pro Val Ile Leu
1               5                   10                  15

Ser Glu Lys Lys Ile Val Thr Arg Val Val Glu Met Gly Asp Ser Phe
            20                  25                  30

Phe Val Phe Gln Glu Pro Leu Asp Ile Ile Glu Arg Ser Cys Arg Lys
        35                  40                  45

His Gly Ser Ser Phe Leu Gly Arg Lys Glu Gly Thr Lys Glu Leu Thr
    50                  55                  60

His Ile Thr His Lys Ala Pro Ile Ala Ile Ser Pro Thr Asp Gln Leu
65                  70                  75                  80

Tyr Phe Phe Pro Thr Tyr Ser Tyr Ser Arg Lys Glu Cys Ala Trp Leu
                85                  90                  95

Ser His Phe Tyr Ile Glu Ser Asn Lys Glu Ser Lys Asp Gly Asn Val
            100                 105                 110

Ile Ile Arg Phe Ile Asn Gly Phe Ala Val Lys Leu Glu Ile Ser Lys
```

```
        115                 120                 125

Ser Ser Phe Glu Asn Gln Leu Asn Arg Thr Ala Lys Leu
    130                 135                 140


<210> SEQ ID NO 41
<211> LENGTH: 579
<212> TYPE: DNA
<213> ORGANISM: Bacillus thuringiensis

<400> SEQUENCE: 41

atggagaaca aggtggagag atacgtggag aactacgtgg tgaacaagaa caccatggcc      60

ctgctgcccg tgatcctgag cgagaagaag atcgtgacca gagtggtgga ggtgcaggac     120

agcttcttcg tgttccagaa gcccctggac atcatcgaga gaagctgcag aaagcacggc     180

agcagcttcc tgggcagaaa ggagggcacc aaggagctga cccacatcac ccacaaggcc     240

cccatcgcca tcagccccac cgaccagctg tacttcttcc ccacctacag ctacagcaga     300

aaggagtgcg cctggctgag ccacttctac atcgagagca acaaggagct gaaggacggc     360

aacctgatca tcagattcat caacggcttc gccgtgaagc tggagatcag caagaccagc     420

ttcgagaacc agcagaacag aaccgccaag ctgagaaccg agtacgagga cagaagaaag     480

aagcagggca acccctgctt caaggaggtg gaccagagag acgagagcac cctgagaccc     540

gcctacgaga gagtgtacgt ggtgagagag gaggacgtg                            579


<210> SEQ ID NO 42
<211> LENGTH: 141
<212> TYPE: PRT
<213> ORGANISM: Bacillus sp.

<400> SEQUENCE: 42

Asn Tyr Val Val Asn Lys Asn Thr Met Ala Leu Leu Pro Val Ile Leu
1               5                   10                  15

Ser Glu Lys Lys Ile Val Thr Arg Val Val Glu Met Glu Asp Ser Phe
            20                  25                  30

Phe Val Phe Gln Lys Pro Leu Asp Ile Ile Glu Arg Ser Cys Arg Lys
        35                  40                  45

His Gly Ser Ser Phe Leu Gly Arg Lys Glu Gly Thr Lys Glu Leu Thr
    50                  55                  60

His Ile Thr His Lys Ala Pro Ile Ala Ile Ser Pro Ala Asp Gln Phe
65                  70                  75                  80

Tyr Phe Phe Pro Thr Tyr Ser Tyr Ser Arg Lys Glu Cys Ala Trp Leu
                85                  90                  95

Ser His Phe Tyr Ile Glu Ser Asn Lys Glu Leu Lys Asp Gly Asn Val
            100                 105                 110

Ile Val Arg Phe Ile Asn Gly Phe Ala Val Lys Leu Glu Ile Ser Lys
        115                 120                 125

Ser Ser Ser Glu Asn Gln Leu Asn Arg Thr Ala Lys Leu
    130                 135                 140


<210> SEQ ID NO 43
<211> LENGTH: 579
<212> TYPE: DNA
<213> ORGANISM: Bacillus cereus

<400> SEQUENCE: 43

atggagagca aggtggagag atacgtggag aactacgtgg tgaacaagaa caccatggcc      60

ctgctgcccg tgatcctgag cgagaagaag atcgtgacca gagtggtgga ggtgcaggac     120
```

-continued

```
agcttcttcg tgttccagaa gcccctggac atcatcgaga gaagctgcag aaagcacggc    180

agcagcttcc tgggcagaaa ggagggcacc aaggagctga cccacatcac ccacaaggcc    240

cccatcgcca tcagccccac cgaccagctg tacttcttcc ccacctacag ctacagcaga    300

aaggagtgcg cctggctgag ccacttctac atcgagagca acaaggagct gaaggacggc    360

aacctgatca tcagattcat caacggcttc gccgtgaagc tggagatcag caagaccagc    420

ttcgagaacc agcagaacag aaccgccaag ctgagaaccg agtacgagga cagaagaaag    480

aagcagggca acccctgctt caaggaggtg gaccagagag acgagagcac cctgagaccc    540

gcctacgaga aggtgtactt cgtgagagag gaggacctg                          579
```

<210> SEQ ID NO 44
<211> LENGTH: 141
<212> TYPE: PRT
<213> ORGANISM: Bacillus sp.

<400> SEQUENCE: 44

```
Asn Tyr Val Val Asn Lys Asn Thr Met Ala Leu Leu Ser Val Ile Leu
1               5                   10                  15

Ser Glu Lys Lys Ile Val Thr Arg Val Val Glu Met Gly Asp Ser Phe
            20                  25                  30

Phe Val Phe Gln Lys Pro Leu Asp Ile Ile Glu Arg Ser Cys Arg Lys
        35                  40                  45

His Gly Ser Ser Phe Leu Gly Arg Lys Glu Gly Thr Lys Glu Leu Thr
    50                  55                  60

His Ile Thr His Lys Ala Pro Ile Ala Ile Ser Pro Thr Asp Gln Leu
65                  70                  75                  80

Tyr Phe Phe Pro Thr Tyr Ser Tyr Ser Arg Lys Glu Cys Ala Trp Leu
                85                  90                  95

Ser His Phe Tyr Ile Glu Ser Asn Lys Glu Ser Lys Asp Gly Asn Val
            100                 105                 110

Ile Ile Arg Phe Ile Asn Gly Phe Ala Val Lys Leu Glu Ile Ser Lys
        115                 120                 125

Ser Ser Phe Glu Asn Gln Leu Asn Arg Thr Ala Lys Leu
    130                 135                 140
```

<210> SEQ ID NO 45
<211> LENGTH: 579
<212> TYPE: DNA
<213> ORGANISM: Bacillus cereus

<400> SEQUENCE: 45

```
atggagagca aggtggagag atacgtggag aactacgtgg tgaccaagaa caccatggcc     60

ctgctgcccg tgatcctgag cgagaagaag atcgtgacca gagtggtgga gatgaacgac    120

agcttcttcg tgttccagaa gcccctggac atcatcgaga gaagctgcag aaagcacggc    180

agcagcttcc tgggcagaaa ggagggcacc aaggagctga cccacatcac ccacaaggcc    240

cccatcgcca tcagccccgc cgaccagctg tacttcttcc ccacctacag ctacagcaga    300

aaggagtgcg cctggctgag ccacttctac atcgagagca acaaggagct gaaggacggc    360

aacctgatca tcagattcat caacggcttc gccgtgaagc tggagatcag caagaccagc    420

ttcgagaacc agcagaacag aaccgccaag ctgagaaccg agtacgagga cagaagaaag    480

aagcagggca acccctgctt caaggaggtg gacaagaagg aggagagcac cctgagaccc    540

gcctacgaga gcgtgtactt cgtgaaggag ggcgaggtg                          579
```

<210> SEQ ID NO 46
<211> LENGTH: 141
<212> TYPE: PRT
<213> ORGANISM: Bacillus sp.

<400> SEQUENCE: 46

Asn Tyr Val Val Thr Lys Asn Thr Met Ala Leu Leu Pro Val Ile Leu
1 5 10 15

Ser Glu Lys Lys Ile Ala Thr Arg Val Val Glu Met Asn Asp Ser Phe
20 25 30

Phe Val Phe Gln Lys Pro Leu Asp Ile Ile Glu Arg Ser Cys Arg Lys
35 40 45

His Gly Ser Ser Phe Leu Gly Arg Lys Glu Gly Thr Lys Glu Leu Thr
50 55 60

His Ile Thr His Lys Ala Pro Ile Ala Ile Ser Pro Ala Asp Gln Leu
65 70 75 80

Tyr Phe Phe Pro Thr Tyr Ser Tyr Ser Arg Lys Glu Cys Ala Trp Leu
85 90 95

Ser His Phe Tyr Ile Glu Ser Asn Lys Glu Leu Lys Asp Gly Asn Leu
100 105 110

Ile Ile Arg Phe Ile Asn Gly Phe Ala Val Lys Leu Glu Ile Ser Lys
115 120 125

Thr Ser Phe Glu Asn Gln Gln Asn Arg Thr Ala Lys Leu
130 135 140

<210> SEQ ID NO 47
<211> LENGTH: 579
<212> TYPE: DNA
<213> ORGANISM: Bacillus anthracis

<400> SEQUENCE: 47
atggagaaca aggtggagag atacgtggag aactacgtgg tgaacaagaa caccatggcc 60
ctgctgcccg tgatcctgag cgagaagaag atcgtgacca gagtggtgga ggtgcaggac 120
agcttcttcg tgttccagaa gcccctggac atcatcgaga gaagctgcag aaagcacggc 180
agcagcttcc tgggcagaaa ggagggcacc aaggagctga cccacatcac ccacaaggcc 240
cccatcgcca tcagccccac cgaccagctg tacttcttcc ccacctacag ctacagcaga 300
aaggagtgcg cctggctgag ccacttctac atcgagagca acaaggagct gaaggacggc 360
aacctgatca tcagattcat caacggcttc gccgtgaagc tggagatcag caagaccagc 420
ttcgagaacc agcagaacag aaccgccaag ctgagaaccg agtacgagga cagaagaaag 480
aagcagggca acccctgctt caaggaggtg gacaagaacg aggagagcag actgaagccc 540
gcctacgaga gcgtgtactt cgtgaaggag gaggaggtg 579

<210> SEQ ID NO 48
<211> LENGTH: 141
<212> TYPE: PRT
<213> ORGANISM: Bacillus sp.

<400> SEQUENCE: 48

Asn Tyr Val Val Thr Lys Asn Thr Met Ala Leu Leu Pro Val Ile Leu
1 5 10 15

Ser Glu Lys Lys Ile Val Thr Arg Val Val Glu Met Asn Asp Ser Phe
20 25 30

Phe Val Phe Gln Lys Pro Leu Asp Ile Ile Glu Arg Ser Cys Arg Lys
35 40 45

Asn Gly Ser Ser Phe Leu Gly Arg Lys Glu Gly Thr Lys Glu Leu Thr 50 55 60

His Ile Thr His Lys Ala Pro Ile Ala Ile Ser Pro Ala Asp Gln Leu
65 70 75 80

Tyr Phe Phe Pro Thr Tyr Ser Tyr Ser Arg Lys Glu Cys Ala Trp Leu
85 90 95

Ser His Phe Tyr Ile Glu Ser Asn Lys Glu Leu Lys Asp Gly Asn Leu
100 105 110

Ile Ile Arg Phe Ile Asn Gly Phe Ala Val Lys Leu Glu Ile Ser Lys
115 120 125

Thr Ser Phe Glu Asn Gln Gln Asn Arg Thr Ala Lys Leu
130 135 140

<210> SEQ ID NO 49
<211> LENGTH: 576
<212> TYPE: DNA
<213> ORGANISM: Bacillus licheniformis

<400> SEQUENCE: 49
atgagcaccg aggacatgac caaggacacc tacgaggtga acagcagcac catggccgtg 60
ctgcccctgg gcgagggcga gaagcccgcc agcaagatcc tggagaccga cagaaccttc 120
agagtgaaca tgaagccctt ccagatcatc gagagaagct gcagatactt cggcagcagc 180
tacgccggca gaaaggccgg cacctacgag gtgatcaagg tgagccacaa gccccccatc 240
atggtggacc acagcaacaa catcttcctg ttccccacct tcagcagcac cagaccccag 300
tgcggctggc tgagccacgc ccacgtgcac gagttctgcg ccgccaagta cgacaacacc 360
ttcgtgacct tcgtgaacgg cgagaccctg gagctgcccg tgagcatcag cagcttcgag 420
aaccaggtgt acagaaccgc ctggctgacc accaagttca tcgacagaat cgagggcaac 480
cccatgcaga agaagcagga gttcatgctg taccccaagg aggacagaaa ccagctgatc 540
tacgagttca tcctgagaga gctgaagaag agatac 576

<210> SEQ ID NO 50
<211> LENGTH: 168
<212> TYPE: PRT
<213> ORGANISM: Bacillus thuringiensis

<400> SEQUENCE: 50

Met Asn Asp Glu Asn Asn Ile Ile Ile Ser Ser Ser Thr Met Met Leu
1 5 10 15

Val Pro Tyr Asn His Pro Tyr Tyr Arg Thr Lys Ile Ile Asp Ser Ser
20 25 30

Gly Asn Asp Leu Cys Ser Cys Gln Thr Ala Leu Gln Leu Ile Lys Lys
35 40 45

Ser Cys Leu Thr Gln Ile His Ser Thr Tyr Gln Gly Arg Arg Asn Ala
50 55 60

Val Gln Thr Asn Phe Arg Phe Lys Gln Asn Val Pro Ile Pro Ile Asn
65 70 75 80

His Arg Glu Tyr Ile Cys Thr Phe Pro Thr Glu Ser Pro Ser Ser Pro
85 90 95

Asn Cys Ile Trp Leu Phe Tyr Asn His Ile His Asp Ile Glu Phe Cys
100 105 110

Gln Lys Ile Lys Glu Ala Lys Ile His Phe Ser Asn Gly Thr Thr Thr
115 120 125

Thr Ile Ser Ile Ser Pro His Lys Leu Gln Gln Gln Leu Leu Lys Ala
130 135 140

```
Gly Tyr Ile Leu Ser Arg Met Asn Met Gln Asp Ser Leu Gln Phe Lys
145                 150                 155                 160

Asn Pro Leu Leu His Leu Leu His
                165
```

<210> SEQ ID NO 51
<211> LENGTH: 1143
<212> TYPE: DNA
<213> ORGANISM: Bacillus licheniformis

<400> SEQUENCE: 51

```
atgttctata ctaatcaacc agccatcaac tgcactacat acaaacaaat gctccgctca      60

actggttcgc tatccaattt gttctctgaa agtgactcgc cttatttggt ctcaaggaat     120

gtggaaaatg ctttttgtga agcatttgga gctgaaaact tggggaggtc agactgttct     180

gctgacgctt cattaaatcg tgtcggaatt ggtattaaga cttttcttca tggtaatggt     240

catactcttc aaaaagtagc tgaattcaat aaagactcag acttgtatcg tgggaaatct     300

ccaaaagagc taataaacac ggttgcttct ctccgtaacg agagaattga atttactaaa     360

agaacatatg gtattgattc aatgatatac cactgtgtaa caagaaagcc agggaaaatt     420

cttatttttg aagagccaat ggacttggtt gaaatctcct caattacaaa tgtgaaagta     480

agtaacaaca gaaatacaat cacctttgaa gacggtctac acgaatacag ctttaatgtc     540

actaagagca ccctttataa gcgttttatc actgataaac ctattgaaga aattaatgtt     600

gaaatcttag aaaatcctta tcatgaattg gctaaactat ttggctttga aattccaaaa     660

attccagcac caactgtcaa tccttttgaa aaccttgagc acgttattct tccactcttt     720

tcagaccgtg gctcaaagcg tcatgtacca gaaaaaagcg gtctaaacca atggaatgct     780

ttaggtcgac cacgaaaccc taacgagatt tatataccaa ttccaaaatg gattcataat     840

gtattcccaa catttttccc agctcgtgat aaaccttttc agttacgctt gccagacaaa     900

tcgcttttat cagccaaggt atgccaagac aatagtaaag cacttatgtc taatccaaat     960

agtgctcttg gagaatggct actaagacaa gttatgaact tagaggaaaa agaacttcta    1020

acctatgaaa tgctggaaag actaaatatt gactcagtaa ttgtttataa acacagcgaa    1080

caacattact ccattgattt ttgtgaaatg ggttcttatg atgaatttga aaatgaaaac    1140

aaa                                                                  1143
```

<210> SEQ ID NO 52
<211> LENGTH: 381
<212> TYPE: PRT
<213> ORGANISM: Bacillus licheniformis

<400> SEQUENCE: 52

```
Met Phe Tyr Thr Asn Gln Pro Ala Ile Asn Cys Thr Thr Tyr Lys Gln
1               5                   10                  15

Met Leu Arg Ser Thr Gly Ser Leu Ser Asn Leu Phe Ser Glu Ser Asp
            20                  25                  30

Ser Pro Tyr Leu Val Ser Arg Asn Val Glu Asn Ala Phe Cys Glu Ala
        35                  40                  45

Phe Gly Ala Glu Asn Leu Gly Arg Ser Asp Cys Ser Ala Asp Ala Ser
    50                  55                  60

Leu Asn Arg Val Gly Ile Gly Ile Lys Thr Phe Leu His Gly Asn Gly
65                  70                  75                  80

His Thr Leu Gln Lys Val Ala Glu Phe Asn Lys Asp Ser Asp Leu Tyr
                85                  90                  95
```

-continued

```
Arg Gly Lys Ser Pro Lys Glu Leu Ile Asn Thr Val Ala Ser Leu Arg
            100                 105                 110

Asn Glu Arg Ile Glu Phe Thr Lys Arg Thr Tyr Gly Ile Asp Ser Met
        115                 120                 125

Ile Tyr His Cys Val Thr Arg Lys Pro Gly Lys Ile Leu Ile Phe Glu
    130                 135                 140

Glu Pro Met Asp Leu Val Glu Ile Ser Ser Ile Thr Asn Val Lys Val
145                 150                 155                 160

Ser Asn Asn Arg Asn Thr Ile Thr Phe Glu Asp Gly Leu His Glu Tyr
                165                 170                 175

Ser Phe Asn Val Thr Lys Ser Thr Leu Tyr Lys Arg Phe Ile Thr Asp
            180                 185                 190

Lys Pro Ile Glu Glu Ile Asn Val Glu Ile Leu Glu Asn Pro Tyr His
        195                 200                 205

Glu Leu Ala Lys Leu Phe Gly Phe Glu Ile Pro Lys Ile Pro Ala Pro
    210                 215                 220

Thr Val Asn Pro Phe Glu Asn Leu Glu His Val Ile Leu Pro Leu Phe
225                 230                 235                 240

Ser Asp Arg Gly Ser Lys Arg His Val Pro Glu Lys Ser Gly Leu Asn
                245                 250                 255

Gln Trp Asn Ala Leu Gly Arg Pro Arg Asn Pro Asn Glu Ile Tyr Ile
            260                 265                 270

Pro Ile Pro Lys Trp Ile His Asn Val Phe Pro Thr Phe Phe Pro Ala
        275                 280                 285

Arg Asp Lys Pro Phe Gln Leu Arg Leu Pro Asp Lys Ser Leu Leu Ser
    290                 295                 300

Ala Lys Val Cys Gln Asp Asn Ser Lys Ala Leu Met Ser Asn Pro Asn
305                 310                 315                 320

Ser Ala Leu Gly Glu Trp Leu Leu Arg Gln Val Met Asn Leu Glu Glu
                325                 330                 335

Lys Glu Leu Leu Thr Tyr Glu Met Leu Glu Arg Leu Asn Ile Asp Ser
            340                 345                 350

Val Ile Val Tyr Lys His Ser Glu Gln His Tyr Ser Ile Asp Phe Cys
        355                 360                 365

Glu Met Gly Ser Tyr Asp Glu Phe Glu Asn Glu Asn Lys
    370                 375                 380
```

<210> SEQ ID NO 53
<211> LENGTH: 3049
<212> TYPE: DNA
<213> ORGANISM: Bacillus licheniformis

<400> SEQUENCE: 53

```
tcatgttccc atattctttt aatgttccaa tccttttcct cgtaatattt attaacttcc      60

ttatctcttt ttttatttct ttcgagtttt ttctcccaat attccgtatt actttttggt     120

atattcccgt gtttttcaca cgcatgccag aaacaagaat caatgaatat gactatttta     180

tatttctgta ttactatatc tggactaccg tataatttct taacattttt tcggaatctt     240

attccacggt gccatagttc tttagtaacc ttatcttcta attttgaacg agatttgatt     300

gcctgcatgt tttttcttct ttgttctttt gaaaccgtgt cagtcataga agagtcctcc     360

aaagccacaa taattgtatt ctataaacga ggaagcaagc cctcaagctt accccctctt     420

agttcctttt ttgcctactt atttatttgt tttcattttc aaattcatca taagaaccca     480

tttcacaaaa atcaatggag taatgttgtt cgctgtgttt ataaacaatt actgagtcaa     540
```

-continued

```
tatttagtct ttccagcatt tcataggtta gaagttcttt ttcctctaag ttcataactt    600
gtcttagtag ccattctcca agagcactat ttggattaga cataagtgct ttactattgt    660
cttggcatac cttggctgat aaaagcgatt tgtctggcaa gcgtaactga aaaggtttat    720
cacgagctgg gaaaaatgtt gggaatacat tatgaatcca ttttggaatt ggtatataaa    780
tctcgttagg gtttcgtggt cgacctaaag cattccattg gtttagaccg ctttttttctg    840
gtacatgacg ctttgagcca cggtctgaaa agagtggaag aataacgtgc tcaaggtttt    900
caaaaggatt gacagttggt gctggaattt ttggaatttc aaagccaaat agtttagcca    960
attcatgata aggattttct aagatttcaa cattaatttc ttcaataggt ttatcagtga   1020
taaaacgctt ataaagggtg ctcttagtga cattaaagct gtattcgtgt agaccgtctt   1080
caaaggtgat tgtatttctg ttgttactta ctttcacatt tgtaattgag gagatttcaa   1140
ccaagtccat tggctcttca aaaataagaa ttttccctgg ctttcttgtt acacagtggt   1200
atatcattga atcaatacca tatgttcttt tagtaaattc aattctctcg ttacggagag   1260
aagcaaccgt gtttattagc tcttttggag atttcccacg atacaagtct gagtctttat   1320
tgaattcagc tactttttga agagtatgac cattaccatg aagaaaagtc ttaataccaa   1380
ttccgacacg atttaatgaa gcgtcagcag aacagtctga cctccccaag ttttcagctc   1440
caaatgcttc acaaaaagca ttttccacat tccttgagac caaataaggc gagtcacttt   1500
cagagaacaa attggatagc gaaccagttg agcggagcat ttgtttgtat gtagtgcagt   1560
tgatggctgg ttgattagta tagaacatta tttttcctcc tcttttatgc ttgtcatttc   1620
ttctttcaga cccaaaaggt agtcagctga tacgttcaat gtttcagcta ttcttttgaa   1680
agtgtccaat gatggagttc tattttcact ttcatatagt gaccaagtgc ttctagtgac   1740
cccgactttt tcagcgattt ggctgggtaa taacctacga gcttctcttg cattttgaat   1800
acgatttcca aggaaaggta tcatttttgc acctccaaga tttgttgttt tcagagtatc   1860
accagaaccc ccgaaaatag tccaaagtta gctaacagca aacaaataaa aataaataag   1920
ttgtttactc ttagcaaact tgttactaaa atttgataaa gttattcatt taatccagct   1980
cttatgctaa aattgcatta gcggacaagc ttaatgtttg caaggaggta taattttgac   2040
ttatcgagta ggtagtatgt ttgctgggat aggtggaact tgtttagggt ttatccaagc   2100
tggcgctagg attgtctggg caaatgaaat agacaaaaat gcttgtatta cttatagaaa   2160
ttattttggg gatgcttact tacaagaggg tgacattaac ctaatagata aaaactccat   2220
acctgaactg gacattttga ttggaggttt tccttgccaa gccttctcta tagctggcta   2280
tcgtaaaggg tttgaagatg aaaggggaaa cgtgttcttt caaatattag aggtattgga   2340
agcacaaaga aatgtttatg gacacttacc ccaagcaata atgcttgaga atgtaaagaa   2400
cttatttaca catgatagag gtaatacgta cagagtaata aaagaggctt tggaagcctt   2460
tggttatacc gtaaaagctg aggttcttaa ttcaatggaa tacggtaacg tgccacaaaa   2520
cagagagcgg atttatattg taggttttca agatgagagc caagctgaaa ggtttagctt   2580
tccagaccca attcctttaa caaatcaact taatgatgta attgaccgaa ctcggagagt   2640
tgataaaaga tattattatg atgaaacctc tcaatattat gatatgttgc gagaagccat   2700
ggacagtaca gatacaactt atcaaataag acgtatatat gttcgagaaa atagaagcaa   2760
tgtttgtcct acactgacag cgaatatggg aactggaggg cataatgttc ctattgtatt   2820
agactttgaa aataatataa gaaaactaac accagaagaa tgcttactat tgcaaggttt   2880
cccagctgac tatcattttc cagaaggcat ggcaaacact cacaaatata aacaagctgg   2940
```

taactctgtt acggtgccag ttataagaag aattgccact aatattatta gcgtattgaa 3000
cattggaatg aatataaatc aagaacatga atatgcaata gctgaataa 3049

<210> SEQ ID NO 54
<211> LENGTH: 26
<212> TYPE: DNA
<213> ORGANISM: Bacillus licheniformis

<400> SEQUENCE: 54
gagctctgca aggaggtata attttg 26

<210> SEQ ID NO 55
<211> LENGTH: 27
<212> TYPE: DNA
<213> ORGANISM: Bacillus licheniformis

<400> SEQUENCE: 55
acgcgtttat tcagctattg catattc 27

<210> SEQ ID NO 56
<211> LENGTH: 37
<212> TYPE: DNA
<213> ORGANISM: Bacillus licheniformis

<400> SEQUENCE: 56
ccaggcctta agggccgcat gcgtccttct ttgtgct 37

<210> SEQ ID NO 57
<211> LENGTH: 27
<212> TYPE: DNA
<213> ORGANISM: Bacillus licheniformis

<400> SEQUENCE: 57
gagctccttt caatgtgata catatga 27

<210> SEQ ID NO 58
<211> LENGTH: 24
<212> TYPE: DNA
<213> ORGANISM: Bacillus licheniformis

<400> SEQUENCE: 58
gcggccgctc gctttccaat ctga 24

<210> SEQ ID NO 59
<211> LENGTH: 24
<212> TYPE: DNA
<213> ORGANISM: Bacillus licheniformis

<400> SEQUENCE: 59
atcgatcagc ttggataaac ccta 24

<210> SEQ ID NO 60
<211> LENGTH: 26
<212> TYPE: DNA
<213> ORGANISM: Bacillus licheniformis

<400> SEQUENCE: 60
gagctctgca aggaggtata attttg 26

<210> SEQ ID NO 61
<211> LENGTH: 28
<212> TYPE: DNA
<213> ORGANISM: Bacillus licheniformis

<400> SEQUENCE: 61
cgtcgacgcc tttgcggtag tggtgctt 28

<210> SEQ ID NO 62
<211> LENGTH: 19
<212> TYPE: DNA
<213> ORGANISM: Bacillus megaterium

<400> SEQUENCE: 62
gagctcggat cccatttcc 19

<210> SEQ ID NO 63
<211> LENGTH: 94
<212> TYPE: DNA
<213> ORGANISM: Bacillus megaterium

<400> SEQUENCE: 63
atctctgagc tcgcgatgat taattaattc agaacgctcg gttgccgccg ggcgtttttt 60
atgcagcaat ggcaagaacg tcccggttag ctcc 94

<210> SEQ ID NO 64
<211> LENGTH: 43
<212> TYPE: DNA
<213> ORGANISM: Bacillus megaterium

<400> SEQUENCE: 64
cttctcgaga ataatatttc cttctaagtc ggttaggatt ccg 43

<210> SEQ ID NO 65
<211> LENGTH: 79
<212> TYPE: DNA
<213> ORGANISM: Bacillus megaterium

<400> SEQUENCE: 65
caagcatcaa aaaacaccaa cttagttcgg tggataaaca aaggagtggt tattattcaa 60
attgcagatc aggctttag 79

<210> SEQ ID NO 66
<211> LENGTH: 27
<212> TYPE: DNA
<213> ORGANISM: Bacillus licheniformis

<400> SEQUENCE: 66
gtggatccga ttaggaggat caaaatg 27

<210> SEQ ID NO 67
<211> LENGTH: 54
<212> TYPE: DNA
<213> ORGANISM: Bacillus licheniformis

<400> SEQUENCE: 67
cagtactgca gtcaatagcg ctttttcagc tccctgagga taaattcgta tatc 54

<210> SEQ ID NO 68
<211> LENGTH: 24
<212> TYPE: DNA
<213> ORGANISM: Bacillus licheniformis

<400> SEQUENCE: 68
ctgaaacaac aaaaacggct ttac 24

<210> SEQ ID NO 69

-continued

```
<211> LENGTH: 30
<212> TYPE: DNA
<213> ORGANISM: Bacillus licheniformis

<400> SEQUENCE: 69

actgaagctt ggttgcggtc agcgggatcg                                30


<210> SEQ ID NO 70
<211> LENGTH: 25
<212> TYPE: DNA
<213> ORGANISM: Bacillus licheniformis

<400> SEQUENCE: 70

agtcgaattc gactggaagc agagc                                     25


<210> SEQ ID NO 71
<211> LENGTH: 28
<212> TYPE: DNA
<213> ORGANISM: Bacillus licheniformis

<400> SEQUENCE: 71

tcaggagctc agtaccattt tccctata                                  28
```

METHODS OF OBTAINING GENETIC COMPETENCE IN *BACILLUS* CELLS

CROSS-REFERENCE TO RELATED APPLICATIONS

This application is a continuation of U.S. patent application Ser. No. 12/520,075, which is a 35 U.S.C. 371 national application of PCT/US2007/088186 filed on Dec. 19, 2007, which claims priority from U.S. provisional application Ser. No. 60/877,053 filed on Dec. 21, 2006. The contents of these applications are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to methods of obtaining genetic competence in non-competent *Bacillus* cells.

2. Description of the Related Art

Genetic competence is a physiological state in which exogenous DNA can be internalized, leading to a transformation event (Berka et al., 2002, *Mol. Microbiol.* 43: 1331-45), but is distinct from artificial transformation involving electroporation, protoplasts, and heat shock or $CaCl_2$ treatment. Natural competence has been observed in both Gram positive and Gram negative bacterial species (Dubnau, 1999, *Annual Rev. Microbiol.* 53: 217-44), and the process requires more than a dozen proteins whose expression is precisely choreographed to the needs of each organism.

Several hypotheses have been proposed regarding the purpose of natural competence, and they can be summarized as DNA for food, DNA for repair, and DNA for genetic diversity (Dubnau, 1999, supra). The DNA for food hypothesis is supported by observations that competence is a stationary phase phenomenon that occurs when cells are nutrient limited, and often a powerful nonspecific nuclease is co-expressed with transformation specific proteins. Evidence for the second hypothesis comes from the fact that genes encoding DNA repair enzymes are coordinately expressed with those encoding DNA transport proteins. Lastly, the DNA for genetic diversity hypothesis proposes that competence is a mechanism for exploring the fitness landscape via horizontal gene transfer. Observations that competence is regulated by a quorum-sensing mechanism and that it is a bistable condition (Avery, 2005, *Trends Microbiol.* 13: 459-462) support this hypothesis.

Public databases now contain a multitude of complete bacterial genomes, including several genomes from different strains of the same species. Recent analyses have shown, using pairwise whole genome alignments, that different strains of the same species may vary substantially in gene content. For example, genome comparisons of *Escherichia coli* strains CFT073, EDL933, and MG1655 revealed that only 39.2% of their combined set of proteins (gene products) are common to all three strains, highlighting the astonishing diversity among strains of the same species (Blattner et al., 1997, *Science* 277: 1453-74; Hayashi et al., 2006, *Mol. Syst. Biol.* doi:10.1038:msb4100049; Perna et al., 2001, *Nature* 409: 529-33; Welch et al., 2002, *Proc. Natl. Acad. Sci. USA* 99: 17020-17024). Furthermore, the genome sequence of *E. coli* strain CFT073 revealed 1,623 strain-specific genes (21.2%). From comparisons of this type, it is clearly seen that bacterial genomes are segmented into a common conserved backbone and strain-specific sequences. Typically the genome of a given strain within a species shows a mosaic structure in terms of the distribution of conserved "backbone" genes conserved among all strains and non-conserved genes that may have been acquired by horizontal transfer (Brzuszkiewicz et al., 2006, *Proc. Natl. Acad. Sci. USA* 103: 12879-12884; Welch et al., 2002, supra).

In terms of practical utility, transformation via natural competence is an extremely useful tool for constructing bacterial strains, e.g., *Bacillus*, that may contain altered alleles for chromosomal genes or plasmids assembled via recombinant DNA methods. Although transformation of certain species with plasmids and chromosomal DNA may be achieved via artificial means as noted above (e.g., electroporation, protoplasts, and heat shock or $CaCl_2$ treatment), introduction of DNA by natural competence offers clear advantages of simplicity, convenience, speed, and efficiency.

In *Bacillus subtilis*, only 5-10% of the cells in a population differentiate to a competent state (termed the K-state) via a process that involves quorum-sensing, signal transduction, and a cascade of gene expression (Avery, 2005, supra). At least 50 genes are known to be involved directly in competence, and as many as 165 genes are regulated (directly or indirectly) by the central transcription factor ComK (Berka et al., 2002, supra). The competence cascade in *Bacillus subtilis* consists of two regulatory modules punctuated by a molecular switch (FIG. 1) that involves ComS binding to the adaptor molecule MecA, thereby interfering with degradation of the transcription factor ComK by the ClpC/ClpP protease (Turgay et al., 1998, *EMBO J.* 17: 6730-6738).

Much less is known about competence in the closely related species *Bacillus licheniformis*. Thorne and colleagues (Gwinn and Thorne, 1964, supra; Leonard et al., 1964, *J. Bacteriol.* 88: 220-225; Thorne and Stull, 1966, *J. Bacteriol.* 91: 1012-1020) published a series of papers in the 1960s that described transformation of three auxotrophic mutants derived from *Bacillus licheniformis* ATCC 9945A via natural competence. Natural competence was observed only in three specific auxotrophic mutants, 9945A-M28 ($gly^-$), -M30 (uncharacterized auxotroph), and -M33 ($pur^-$). Numerous other auxotrophs derived from the same parental strain (ATCC 9945A) did not give rise to transformants including those with requirements for thiamine, lysine, arginine, methionine, tryptophan, histidine, uracil, adenine, or hypoxanthine, and 13 other uncharacterized auxotrophic requirements (Gwinn and Thorne, 1964, supra). Furthermore, these investigators were unable to demonstrate transformation via natural competence in *Bacillus licheniformis* ATCC 10716 (Gwinn and Thorne, 1964, supra). As suggested by the early work of Thorne and colleagues, most *Bacillus licheniformis* isolates do not manifest natural competence, and in recent years genetic transformation of many *Bacillus licheniformis* isolates has been achieved only via electroporation (Tangney et al., 1994, *Biotechnol. Techniques* 8: 463-466), conjugation (Herzog-Velikonja et al., 1994, *Plasmid* 31: 201-206), or protoplasting (Pragai et al., 1994, *Microbiol* (Reading) 140: 305-310). The reasons for the apparent lack of a competent state in *Bacillus licheniformis* are unknown.

Ashikaga et al., 2000, *Journal of Bacteriology* 182: 2411-2415, describe the ability of *Bacillus subtilis* subsp. *natto* to develop genetic competence and the expression of the late competence genes required for incorporation of exogenous DNA. Liu et al., 1996, *Journal of Bacteriology* 178: 5144-5152, describe the elevation of competence gene transcription and transformation efficiency in wild-type *Bacillus sub-*

*tilis* by multicopy expression of comS. Tortosa et al., 2000, *Molecular Microbiology* 35: 1110-1119, demonstrate that disruption of the ylbF gene leads to a decrease in expression of comK and that overexpression of comS suffices to bypass the competence phenotype of a ylbF mutation.

Since *Bacillus licheniformis* is a species of industrial importance, engineering strains that manifest natural competence is highly desirable for construction of new and improved production strains. The availability of a turn-key method for inducing competence in poorly transformable *Bacillus licheniformis* strains would improve the speed and efficiency with which chromosomal markers/alleles and expression vectors could be introduced. As described herein, the terms poorly transformable and non-competent are used interchangeably, and these terms mean that the number of transformants per microgram of DNA is less than twice the spontaneous mutation frequency when using the methods for competence-mediated transformation in *Bacillus subtilis* or *Bacillus licheniformis* as described previously (Anagnostopoulos and Spizizen, 1961, *J. Bacteriol.* 81: 741-746; Thorne and Stull, 1966, *J. Bacteriol.* 91: 1012-1020; Gwinn and Thorne, 1964, supra).

The present invention relates to methods of obtaining genetic competence in non-competent *Bacillus* cells.

SUMMARY OF THE INVENTION

The present invention relates to methods of obtaining a competent *Bacillus* host cell, comprising:

(a) introducing into a non-competent *Bacillus* host cell at least one copy of a first nucleic acid construct comprising a promoter region operably linked to a polynucleotide encoding a ComS polypeptide, wherein the polynucleotide encoding the ComS polypeptide is foreign to the *Bacillus* host cell; and (b) isolating a competent *Bacillus* host cell comprising the polynucleotide encoding the ComS polypeptide.

The present invention also relates to methods of obtaining a *Bacillus* transformant, comprising:

(a) transforming an exogenous DNA into a *Bacillus* host cell made competent by at least one copy of an introduced first nucleic acid construct comprising a promoter region operably linked to a polynucleotide encoding a ComS polypeptide, wherein the polynucleotide encoding the ComS polypeptide is foreign to the *Bacillus* host cell; and (b) isolating a transformant of the *Bacillus* host cell comprising the exogenous DNA.

The present invention also relates to methods of producing a biological substance, comprising:

(a) cultivating a *Bacillus* host cell transformed with an exogenous DNA encoding or involved in the expression of a substance having biological activity under conditions conducive for production of the substance, wherein the *Bacillus* host cell is made competent by at least one copy of an introduced nucleic acid construct comprising a promoter region operably linked to a polynucleotide encoding a ComS polypeptide, wherein the polynucleotide encoding the ComS polypeptide is foreign to the *Bacillus* host cell that was non-competent prior to introduction of the nucleic acid construct; and (b) recovering the substance having biological activity.

The present invention also relates to a competent *Bacillus* host cell comprising at least one copy of an introduced first nucleic acid construct comprising a promoter region operably linked to a polynucleotide encoding a ComS polypeptide, wherein the polynucleotide encoding the ComS polypeptide is foreign to the *Bacillus* host cell that was non-competent prior to introduction of the first nucleic acid construct.

The present invention also relates to methods of producing a mutant of a parent *Bacillus* cell, comprising:

(a) transforming into a parent *Bacillus* cell an exogenous DNA comprising a nucleic acid construct to modify a gene encoding a polypeptide in the parent *Bacillus* cell, which results in a mutant cell producing less of the polypeptide or producing a polypeptide with lower biological activity than the parent cell when cultivated under the same conditions, wherein the parent *Bacillus* cell is made competent by at least one copy of an introduced nucleic acid construct comprising a promoter region operably linked to a polynucleotide encoding a ComS polypeptide, wherein the polynucleotide encoding the ComS polypeptide is foreign to the parent *Bacillus* cell that was non-competent prior to introduction of the nucleic acid construct; and (b) isolating the mutant cell.

In a preferred aspect, a *Bacillus* cell made competent above further comprises at least one copy of an introduced second nucleic acid construct comprising a promoter region operably linked to a polynucleotide encoding a ComK polypeptide to render the *Bacillus* host cell even further competent.

DESCRIPTION OF THE FIGURES

FIGS. 2A and 2B show the genomic DNA sequence and the deduced amino acid sequence of a *Bacillus licheniformis* DNA methyltransferase (SEQ ID NOs: 51 and 52, respectively).

FIGS. 3A, 3B, and 3C show the genomic DNA sequence of the *Bacillus licheniformis* Bli1904II restriction-modification system comprising the genes encoding Bli1904II restriction endonuclease and M.Bli1904II DNA methyltransferase (SEQ ID NO: 53). Reverse complement of the Bli1904II restriction endonuclease coding region is indicated by double underscoring and the M.Bli1904II DNA methyltransferase coding region is indicated by single underscoring.

FIG. 15 shows an amino acid sequence alignment of ComS proteins encoded by the genomes of *Bacillus subtilis* and *Bacillus licheniformis*.

DEFINITIONS

Figure 1:
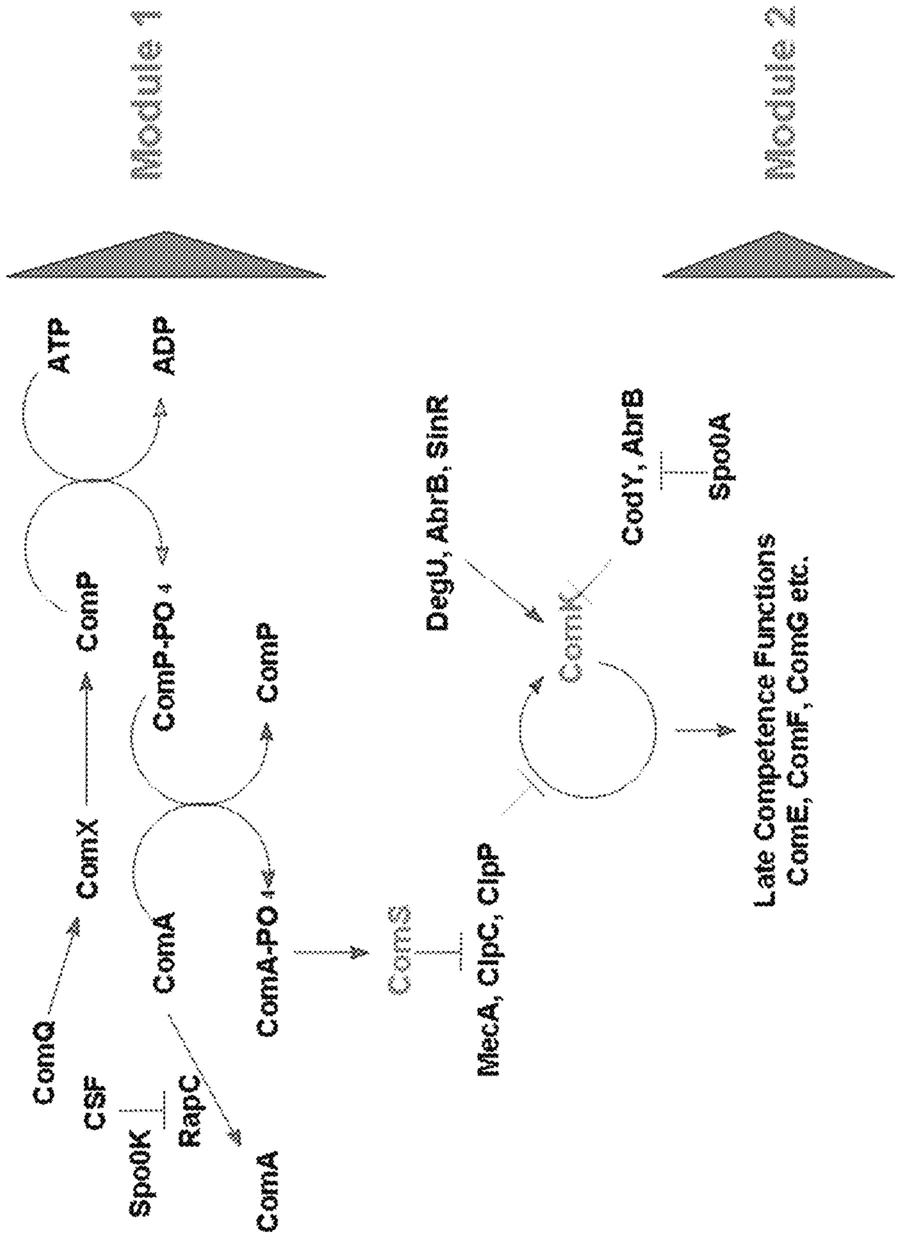
FIG. 1 shows the competence regulatory cascade of *Bacillus subtilis*. Module 1 involves detection of the competence pheromone CSF and signal transduction via a phosphorelay mechanism resulting in synthesis of the ComS peptide. ComS interferes with proteolytic degradation of the transcription factor ComK via binding to MecA that activates Module 2 encoding the late competence functions encoding DNA transport machinery.

Competence: The term "competence" is defined herein as a natural physiological state in which exogenous (extracellular) DNA can be internalized into a *Bacillus* host cell, leading to a transformation event (Berka et al., 2002, *Mol. Microbiol.* 43: 1331-45). Competence is distinct from artificial transformation involving electroporation, protoplasts, heat shock, or $CaCl_2$ treatment.

Competence mechanism (cascade): The terms "competence mechanism" and "competence cascade" are used interchangeably herein and refer to a cellular differentiation process that converts *Bacillus* cells into naturally transformable cells that can take up and incorporate exogenous (extracellular) DNA using specific transport proteins encoded by the late competence genes comprising the comC, comE, comF, and comG operons.

Non-Competent: As described herein, the terms "non-competent" and "poorly transformable" are used interchangeably, and these terms mean that the number of transformants per microgram of DNA is less than twice the spontaneous mutation frequency when using the methods for competence-mediated transformation in *Bacillus subtilis* or *Bacillus licheniformis* as described previously (Anagnostopoulos and Spizizen, 1961, *J. Bacteriol.* 81: 741-746; Thorne and Stull, 1966, *J. Bacteriol.* 91: 1012-1020; Gwinn and Thorne, 1964, supra).

ComS polypeptide: The term "ComS polypeptide" is defined herein as the product of a comS gene that is involved in regulation of genetic competence. ComS is an assembly link between other regulatory components of the competence signal transduction pathway (Ogura et al., 1999, *Mol. Microbiol.* 32: 799-812; Liu and Zuber, 1998, *J. Bacteriol.* 180: 4243-4251).

ComK polypeptide: The term "ComK polypeptide" is defined herein as the product of a comK gene; a transcription factor that acts as the final autoregulatory control switch prior to competence development; involved with activation of the expression of late competence genes involved in DNA-binding and uptake and in recombination (Liu and Zuber, 1998, supra; Hamoen et al., 1998, *Genes Dev.* 12:1539-1550).

Foreign polynucleotide: The term "foreign polynucleotide" and variations thereof are defined herein as a polynucleotide that is not native to a *Bacillus* cell or a polynucleotide that is native to the *Bacillus* cell but has been modified through the use of genetic elements not native to the *Bacillus* cell, or use of native elements that have been manipulated to function in a manner that does not normally occur in the *Bacillus* cell.

Exogenous DNA: The term "exogenous DNA" is defined herein as DNA that is external to a *Bacillus* cell.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

$$(\text{Identical Deoxyribonucleotides} \times 100)/(\text{Length of Alignment} - \text{Total Number of Gaps in Alignment})$$

Peptide fragment: The term "peptide fragment" is defined herein as a ComS polypeptide or a ComK polypeptide having one or more amino acids deleted from the amino and/or carboxyl terminus of the ComS polypeptide or the ComK polypeptide, wherein the fragment has ComS or ComK activity. In a preferred aspect, a ComS fragment of SEQ ID NO: 2, 4, 6, 8, or 10, or a homolog thereof, contains at least 30 amino acid residues, more preferably at least 35 amino acid residues, and most preferably at least 40 amino acid residues. In another preferred aspect, a ComK fragment of SEQ ID NO: 12, 14, 16, 18, 20, 22, 24, 26, 28, 30, 32, 34, 36, 38, 40, 42, 44, 46, 48, or 50, or a homolog thereof, contains at least 400 amino acid residues, more preferably at least 420 amino acid residues, and most preferably at least 440 amino acid residues.

Subsequence: The term "subsequence" is defined herein as a polynucleotide encoding a ComS polypeptide or a ComK polypeptide having one or more nucleotides deleted from the 5' and/or 3' end of the polynucleotide, wherein the subsequence encodes a peptide fragment having ComS or ComK activity. In a preferred aspect, a comS subsequence of SEQ ID NOs: 1, 3, 5, 7, or 9, or a homolog thereof, contains at least 90 nucleotides, more preferably at least 105 nucleotides, and most preferably at least 120 nucleotides. In another preferred aspect, a comK subsequence of SEQ ID NO: 11, 13, 15, 17, 19, 21, 23, 25, 27, 29, 31, 33, 35, 37, 39, 41, 43, 45, 47, or 49, or a homolog thereof, contains at least 1200 nucleotides, more preferably at least 1260 nucleotides, and most preferably at least 1320 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Nucleic acid construct: The term "nucleic acid construct" as used herein refers to a nucleic acid molecule, either single- or double-stranded, which is isolated from a naturally occurring gene or is modified to contain segments of nucleic acids in a manner that would not otherwise exist in nature or is synthetic. The term nucleic acid construct is synonymous with the term "expression cassette" when the nucleic acid construct contains the control sequences required for expression of a coding sequence.

Control sequences: The term "control sequences" is defined herein to include all components, which are necessary or advantageous for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Promoter: The term "promoter" is defined herein as a DNA sequence that binds RNA polymerase and directs the polymerase to the correct downstream transcriptional start site of a polynucleotide encoding a polypeptide having biological activity to initiate transcription. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and/or other nucleotide sequences capable of interacting with transcription factors. The promoter can be a wild-type, variant, hybrid, or consensus promoter.

Promoter region: The term "promoter region" is defined herein as a nucleotide sequence comprising one or more (several) promoter sequences, e.g., tandem triple promoter.

Promoter variant: The term "promoter variant" is defined herein as a promoter having a nucleotide sequence comprising a substitution, deletion, and/or insertion of one or more (several) nucleotides of a parent promoter, wherein the mutant promoter has more or less promoter activity than the corresponding parent promoter. The term "promoter variant" will also encompass natural variants and in vitro generated variants obtained using methods well known in the art such as classical mutagenesis, site-directed mutagenesis, and DNA shuffling.

Tandem promoter: The term "tandem promoter" is defined herein as two or more promoter sequences each of which is operably linked to a coding sequence and mediates the transcription of the coding sequence into mRNA.

Hybrid promoter: The term "hybrid promoter" is defined herein as parts of two or more promoters that are fused together to generate a sequence that is a fusion of the two or more promoters, which when operably linked to a coding sequence of a polynucleotide encoding a polypeptide having biological activity mediates the transcription of the coding sequence into mRNA.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, synthetic, or recombinant nucleotide sequence.

Expression: The term "expression" includes any step involved in the production of a polypeptide of interest including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of interest, and is operably linked to additional nucleotides that provide for its expression.

Host cell: The term "host cell", as used herein, includes any cell type that is susceptible to transformation, transfection, transduction, conjugation, and the like with a nucleic acid construct or expression vector.

Transformation: The term "transformation" is defined herein as introducing an exogenous DNA into a *Bacillus* cell so that the DNA is maintained as a chromosomal integrant or as a self-replicating extra-chromosomal vector.

Transfection: The term "transfection" is defined herein as the transformation of a *Bacillus* host cell with a viral nucleic acid.

Transduction: The term "transduction" is defined herein as the packaging of DNA from a first *Bacillus* cell into a virus particle and the transfer of that bacterial DNA to a second *Bacillus* cell by infection of the second cell with the virus particle.

Conjugation: The term "conjugation" is defined herein as the transfer of DNA directly from one *Bacillus* cell to another *Bacillus* cell through cell-to-cell contact.

Transformant: The term "transformant" is defined herein to generally encompass any *Bacillus* host cell into which an exogenous DNA has been introduced by transformation. The term "transformant" does not include transfectants, conjugants, and transformants generated by an artificial method such as electroporation, protoplasts, heat shock, or $CaCl_2$ treatment.

Modification: The term "modification" means herein any chemical modification of a ComS polypeptide or ComK polypeptide, as well as genetic manipulation of the DNA encoding such a ComS polypeptide or ComK polypeptide. The modification can be a substitution, deletion, and/or insertion of one or more amino acids as well as a replacement of one or more amino acid side chains.

Artificial variant: When used herein, the term "ComS artificial variant" means a ComS polypeptide produced by an organism expressing a modified ComS coding sequence. The term "ComK artificial variant" means a ComK polypeptide produced by an organism expressing a modified ComK coding sequence. The modified nucleotide sequence is obtained through human intervention by modification of a parent ComS or parent ComK coding sequence. The parent sequence can be a wild-type sequence, synthetic sequence, mutated sequence, etc.

DETAILED DESCRIPTION OF THE INVENTION

The present invention relates to methods of obtaining a competent *Bacillus* host cell, comprising: (a) introducing into a non-competent *Bacillus* host cell at least one copy of a first nucleic acid construct comprising a promoter region operably linked to a polynucleotide encoding a ComS polypeptide, wherein the polynucleotide encoding the ComS polypeptide is foreign to the *Bacillus* host cell; and (b) isolating a competent *Bacillus* host cell comprising the polynucleotide encoding the ComS polypeptide.

The present invention also relates to methods of obtaining a *Bacillus* transformant, comprising: (a) transforming an exogenous DNA into a *Bacillus* host cell made competent by at least one copy of an introduced first nucleic acid construct comprising a promoter region operably linked to a polynucleotide encoding a ComS polypeptide, wherein the polynucleotide encoding the ComS polypeptide is foreign to the *Bacillus* host cell that was non-competent prior to introduction of the first nucleic acid construct; and (b) isolating a transformant of the *Bacillus* host cell comprising the DNA.

The methods of the present invention increase the number of transformants obtained by at least 10-fold, preferably at least 100-fold, more preferably at least 1000-fold, even more preferably at least 10,000-fold, and most preferably at least 100,000-fold compared to a non-competent *Bacillus* cell.

*Bacillus* Host Cells

In the methods of the present invention, the *Bacillus* host cell may be any non-competent or poorly transformable *Bacillus* cell. As described herein, the term non-competent or poorly transformable means that the number of transformants per microgram of DNA is less than twice the spontaneous mutation frequency when using the methods for competence-mediated transformation in *Bacillus subtilis* or *Bacillus licheniformis*. The terms non-competent and poorly transformable are used interchangeably herein. It is understood that the term "*Bacillus*" herein also encompasses synonyms of *Bacillus* and genera formerly classified as *Bacillus* such *Geobacillus* and *Paenibacillus*. Non-competent *Bacillus* host cells useful in the practice of the present invention include, but are not limited to, *Bacillus alkalophilus, Bacillus amyloliquefaciens, Bacillus atrophaeus, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus mojavensis, Bacillus pumilus, Bacillus stearothermophilus, Bacillus subtilis, Bacillus thuringiensis*, and *Bacillus vallismortis* cells.

In a preferred aspect, the non-competent *Bacillus* host cell is a *Bacillus amyloliquefaciens, Bacillus lentus, Bacillus licheniformis, Bacillus stearothermophilus* or *Bacillus subtilis* cell. In a more preferred aspect, the non-competent *Bacillus* host cell is a *Bacillus amyloliquefaciens* cell. In another more preferred aspect, the non-competent *Bacillus* host cell is a *Bacillus clausii* cell. In another more preferred aspect, the non-competent *Bacillus* host cell is a *Bacillus licheniformis* cell. In another more preferred aspect, the non-competent *Bacillus* host cell is a *Bacillus subtilis* cell. In a most preferred aspect, the non-competent *Bacillus* host cell is a *Bacillus licheniformis* cell.

In a further aspect of the present invention, the *Bacillus* host cells may additionally contain one or more (several) modifications, e.g., deletions or disruptions, of other genes that may be detrimental to the production, recovery, or application of a polypeptide or biochemical of interest. In a preferred aspect, the *Bacillus* host cell is a protease-deficient cell. In a more preferred aspect, the *Bacillus* host cell comprises a disruption or deletion of aprE and nprE. In another preferred aspect, the *Bacillus* host cell does not produce spores. In another more preferred aspect, the *Bacillus* host cell comprises a disruption or deletion of spoIIAC. In another preferred aspect, the *Bacillus* host cell comprises a disruption or deletion of one of the genes involved in the biosynthesis of surfactin, e.g., srfA, srfB, srfC, and srfD. See, for example, U.S. Pat. No. 5,958,728. Other genes, e.g., the amyE gene, which are detrimental to the production, recovery, or application of a polypeptide or biological substance of interest may also be disrupted or deleted.

The present invention also relates to a competent *Bacillus* host cell comprising at least one copy of an introduced first nucleic acid construct comprising a promoter region operably linked to a polynucleotide encoding a ComS polypeptide, wherein the polynucleotide encoding the ComS polypeptide is foreign to the *Bacillus* host cell that was non-competent prior to introduction of the first nucleic acid construct.

In a preferred aspect, a *Bacillus* host cell made competent above further comprises at least one copy of an introduced second nucleic acid construct comprising a promoter region operably linked to a polynucleotide encoding a ComK polypeptide to render the *Bacillus* host cell even further competent above the competence obtained by expression of a ComS polypeptide. The *Bacillus* host cell is even further competent by further increasing the number of transformants obtained by at least 2-fold, preferably at least 5-fold, more preferably at least 10-fold, more preferably at least 100-fold, even more preferably at least 1000-fold, most preferably at least 10,000-fold, and even most preferably at least 100,000-fold compared to the competent *Bacillus* cell obtained by expression of a ComS polypeptide.

The present invention also relates to such competent *Bacillus* host cells comprising a nucleic acid construct or recombinant expression vector comprising a DNA of interest encoding or involved in the expression of a biological substance.

ComS Polypeptides and ComK Polypeptides and Polynucleotides Thereof

In the methods of the present invention, any isolated polynucleotide encoding a ComS polypeptide may be used that is suitable for rendering a non-competent *Bacillus* cell genetically competent. In addition, any isolated polynucleotide encoding a ComK polypeptide may be used that is suitable for rendering a competent *Bacillus* cell genetically more competent.

The isolated polynucleotide may be of genomic, cDNA, semisynthetic, synthetic origin, or any combinations thereof.

Polynucleotides encoding a ComS polypeptide can be obtained from, for example, *Bacillus amyloliquefaciens* (Accession No. Q70KJ5), *Bacillus subtilis* (Accession Nos. P80355 and Q83WC2), or *Bacillus licheniformis.*

Polynucleotides encoding a ComK polypeptide can be obtained from, for example, *Bacillus subtilis* 168 (Accession No. P40396), *Bacillus licheniformis* (DSM 13/ATCC 14580; (Accession No. Q65LN7), *Bacillus licheniformis* (Accession No. Q8VQ66), *Bacillus* sp. Bt 24 (Accession No. Q2HQ42), *Bacillus weihenstephanensis* KBAB4 (Accession No. Q2AUN4), *Bacillus thuringiensis* subsp. *Konkukian* (Accession No. Q6HM51), *Bacillus cereus* (ATCC 10987; (Accession No. Q73C31), *Bacillus cereus* (strain ZK/E33L; (Accession No. Q63EM6), *Bacillus cereus* G9241 (Accession No. Q4MPH9), *Bacillus anthracis* (Accession No. Q81TW5), *Bacillus cereus* (ATCC 14579/DSM 31; Accession No. Q81GQ3), *Bacillus cereus* subsp. *cytotoxis* NVH 391-98 (Accession No. Q2E900), *Bacillus* sp. NRRL B-14911 (Accession No. Q2B9A0), *Bacillus* sp. Ob 20 (Accession No. Q2HQ30), *Bacillus* sp. Bt 26 (Accession No. Q2HQ36), *Bacillus* sp. Ob 07 (Accession No. Q2HQ38), *Bacillus* sp. Bt 30 (Accession No. Q2HQ39), *Bacillus* sp. Bt 35 (Accession No. Q2HQ35), *Bacillus* sp. Ob 12b (Accession No. Q2HQ37), and *Bacillus thuringiensis* subsp. *israelensis* (ATCC 35646; (Accession No. Q3EYL1).

In a first aspect, the isolated polynucleotides encoding ComS polypeptides comprise an amino acid sequence having a degree of identity to SEQ ID NO: 2, SEQ ID NO: 4, SEQ ID NO: 6, SEQ ID NO: 8, or SEQ ID NO: 10, of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% (hereinafter "homologous ComS polypeptides" or "ComS homologs"). In a preferred aspect, the homologous ComS polypeptides comprise an amino acid sequence that differs by ten amino acids, preferably by five amino acids, more preferably by four amino acids, even more preferably by three amino acids, most preferably by two amino acids, and even most preferably by one amino acid from SEQ ID NO: 2, SEQ ID NO: 4, SEQ ID NO: 6, SEQ ID NO: 8, or SEQ ID NO: 10.

The isolated polynucleotide preferably encodes a ComS polypeptide comprising the amino acid sequence of SEQ ID NO: 2, SEQ ID NO: 4, SEQ ID NO: 6, SEQ ID NO: 8, or SEQ ID NO: 10, or an allelic variant thereof; or a fragment thereof having ComS activity. In a preferred aspect, the ComS polypeptide comprises the amino acid sequence of SEQ ID NO: 2, SEQ ID NO: 4, SEQ ID NO: 6, SEQ ID NO: 8, or SEQ ID NO: 10. In another preferred aspect, the ComS polypeptide consists of the amino acid sequence of SEQ ID NO: 2, SEQ ID NO: 4, SEQ ID NO: 6, SEQ ID NO: 8, or SEQ ID NO: 10, or an allelic variant thereof; or a fragment thereof having ComS activity. In another preferred aspect, the ComS polypeptide consists of the amino acid sequence of SEQ ID NO: 2, SEQ ID NO: 4, SEQ ID NO: 6, SEQ ID NO: 8, or SEQ ID NO: 10.

In another first aspect, the isolated polynucleotides encoding ComK polypeptides comprise an amino acid sequence having a degree of identity to SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% (hereinafter "homologous ComK polypeptides" or "ComK homologs"). In a preferred aspect, the homologous ComK polypeptides comprise an amino acid sequence that differs by ten amino acids, preferably by five amino acids, more preferably by four amino acids, even more preferably by three amino acids, most preferably by two amino acids, and even most preferably by one amino acid from SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50.

The isolated polynucleotide preferably encodes a ComK polypeptide comprising the amino acid sequence of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50, or an allelic variant thereof; or a fragment thereof having ComK activity. In a preferred aspect, the ComK polypeptide comprises the amino acid sequence of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50. In another preferred aspect, the ComK polypeptide consists of the amino acid sequence of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50, or an allelic variant thereof; or a fragment thereof having ComK activity. In another preferred aspect, the ComK polypeptide consists of the amino acid sequence of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50.

In a second aspect, the isolated polynucleotides encoding ComS polypeptides hybridize under preferably at least very low stringency conditions, more preferably at least low stringency conditions, more preferably at least medium stringency conditions, more preferably at least medium-high stringency conditions, even more preferably at least high stringency conditions, and most preferably at least very high stringency conditions with SEQ ID NO: 1, SEQ ID NO: 3, SEQ ID NO: 5, SEQ ID NO: 7, or SEQ ID NO: 9, (ii) a subsequence of (i), or (iii) a full-length complementary strand of (i) or (ii) (J. Sambrook, E. F. Fritsch, and T. Maniatis, 1989, *Molecular Cloning, A Laboratory Manual,* 2d edition, Cold Spring Harbor, N.Y. A subsequence of SEQ ID NO: 1, SEQ ID NO: 3, SEQ ID NO: 5, SEQ ID NO: 7, or SEQ ID NO: 9 contains at least 90 contiguous nucleotides or preferably at least 120 contiguous nucleotides. Moreover, the subsequence may encode a polypeptide fragment having ComS activity.

In another second aspect, the isolated polynucleotides encoding ComK polypeptides hybridize under preferably at least very low stringency conditions, more preferably at least low stringency conditions, more preferably at least medium stringency conditions, more preferably at least medium-high stringency conditions, even more preferably at least high stringency conditions, and most preferably at least very high stringency conditions with SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49, (ii) a subsequence of (i), or (iii) a full-length complementary strand of (i) or (ii) (J. Sambrook, E. F. Fritsch, and T. Maniatis, 1989, *Molecular Cloning, A Laboratory Manual,* 2d edition, Cold Spring Harbor, N.Y. A subsequence of SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49 contains at least 100 contiguous nucleotides or preferably at least 200 contiguous nucleotides. Moreover, the subsequence may encode a polypeptide fragment having ComK activity.

The nucleotide sequences described above, or subsequences thereof, as well as the amino acid sequences described above, or fragments thereof, may be used to design nucleic acid probes to identify and clone DNA encoding ComS polypeptides and ComK polypeptides from strains of different genera or species according to methods well known in the art. In particular, such probes can be used for hybridization with the genomic DNA of the genus or species of interest, following standard Southern blotting procedures, in order to identify and isolate the corresponding gene therein. Such probes can be considerably shorter than the entire sequence, but should be at least 14, preferably at least 17, more preferably at least 20, and most preferably at least 50 nucleotides in length. It is, however, preferred that the nucleic acid probes are at least 60 nucleotides in length. For example, the nucleic acid probes may be at least 100 nucleotides. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other organisms may, therefore, be screened for DNA that hybridizes with the probes described above and encodes a ComS polypeptide or a ComK polypeptide. Genomic DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, or SEQ ID NO: 9, or a subsequence thereof, or SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49, a full-length complementary strand thereof, or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, SEQ ID NO: 3, SEQ ID NO: 5, SEQ ID NO: 7, or SEQ ID NO: 9, a full-length complementary strand thereof, or a subsequence thereof, or SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49, a full-length complementary strand thereof, or a subsequence thereof, under very low to very high stringency conditions. Molecules to which the nucleic acid probe hybridizes under these conditions can be detected using, for example, X-ray film.

In a preferred aspect, the nucleic acid probe is a polynucleotide that encodes the ComS polypeptide of SEQ ID NO: 2, or a subsequence thereof. In another preferred aspect, the nucleic acid probe is SEQ ID NO: 1 or its full-length complementary strand.

In another preferred aspect, the nucleic acid probe is a polynucleotide that encodes the ComS polypeptide of SEQ ID NO: 4, or a subsequence thereof. In another preferred aspect, the nucleic acid probe is SEQ ID NO: 3 or its full-length complementary strand.

In another preferred aspect, the nucleic acid probe is a polynucleotide that encodes the ComS polypeptide of SEQ ID NO: 6, or a subsequence thereof. In another preferred aspect, the nucleic acid probe is SEQ ID NO: 5 or its full-length complementary strand.

In another preferred aspect, the nucleic acid probe is a polynucleotide that encodes the ComS polypeptide of SEQ ID NO: 8, or a subsequence thereof. In another preferred aspect, the nucleic acid probe is SEQ ID NO: 7 or its full-length complementary strand.

In another preferred aspect, the nucleic acid probe is a polynucleotide that encodes the ComS polypeptide of SEQ ID NO: 10, or a subsequence thereof. In another preferred aspect, the nucleic acid probe is SEQ ID NO: 9 or its full-length complementary strand.

In another preferred aspect, the nucleic acid probe is a polynucleotide that encodes the ComK polypeptide of SEQ ID NO: 12, or a subsequence thereof. In another preferred aspect, the nucleic acid probe is SEQ ID NO: 11 or its full-length complementary strand.

In another preferred aspect, the nucleic acid probe is a polynucleotide that encodes the ComK polypeptide of SEQ ID NO: 14, or a subsequence thereof. In another preferred aspect, the nucleic acid probe is SEQ ID NO: 13 or its full-length complementary strand.

In another preferred aspect, the nucleic acid probe is a polynucleotide that encodes the ComK polypeptide of SEQ ID NO: 16, or a subsequence thereof. In another preferred aspect, the nucleic acid probe is SEQ ID NO: 15 or its full-length complementary strand.

In another preferred aspect, the nucleic acid probe is a polynucleotide that encodes the ComK polypeptide of SEQ ID NO: 18, or a subsequence thereof. In another preferred aspect, the nucleic acid probe is SEQ ID NO: 17 or its full-length complementary strand.

In another preferred aspect, the nucleic acid probe is a polynucleotide that encodes the ComK polypeptide of SEQ ID NO: 20, or a subsequence thereof. In another preferred aspect, the nucleic acid probe is SEQ ID NO: 19 or its full-length complementary strand.

In another preferred aspect, the nucleic acid probe is a polynucleotide that encodes the ComK polypeptide of SEQ ID NO: 22, or a subsequence thereof. In another preferred aspect, the nucleic acid probe is SEQ ID NO: 21 or its full-length complementary strand.

In another preferred aspect, the nucleic acid probe is a polynucleotide that encodes the ComK polypeptide of SEQ ID NO: 24, or a subsequence thereof. In another preferred aspect, the nucleic acid probe is SEQ ID NO: 23 or its full-length complementary strand.

In another preferred aspect, the nucleic acid probe is a polynucleotide that encodes the ComK polypeptide of SEQ ID NO: 26, or a subsequence thereof. In another preferred aspect, the nucleic acid probe is SEQ ID NO: 25 or its full-length complementary strand.

In another preferred aspect, the nucleic acid probe is a polynucleotide that encodes the ComK polypeptide of SEQ ID NO: 28, or a subsequence thereof. In another preferred aspect, the nucleic acid probe is SEQ ID NO: 27 or its full-length complementary strand.

In another preferred aspect, the nucleic acid probe is a polynucleotide that encodes the ComK polypeptide of SEQ ID NO: 30, or a subsequence thereof. In another preferred aspect, the nucleic acid probe is SEQ ID NO: 29 or its full-length complementary strand.

In another preferred aspect, the nucleic acid probe is a polynucleotide that encodes the ComK polypeptide of SEQ ID NO: 32, or a subsequence thereof. In another preferred aspect, the nucleic acid probe is SEQ ID NO: 31 or its full-length complementary strand.

In another preferred aspect, the nucleic acid probe is a polynucleotide that encodes the ComK polypeptide of SEQ ID NO: 34, or a subsequence thereof. In another preferred aspect, the nucleic acid probe is SEQ ID NO: 33 or its full-length complementary strand.

In another preferred aspect, the nucleic acid probe is a polynucleotide that encodes the ComK polypeptide of SEQ ID NO: 36, or a subsequence thereof. In another preferred aspect, the nucleic acid probe is SEQ ID NO: 35 or its full-length complementary strand.

In another preferred aspect, the nucleic acid probe is a polynucleotide that encodes the ComK polypeptide of SEQ ID NO: 38, or a subsequence thereof. In another preferred aspect, the nucleic acid probe is SEQ ID NO: 37 or its full-length complementary strand.

In another preferred aspect, the nucleic acid probe is a polynucleotide that encodes the ComK polypeptide of SEQ ID NO: 40, or a subsequence thereof. In another preferred aspect, the nucleic acid probe is SEQ ID NO: 39 or its full-length complementary strand.

In another preferred aspect, the nucleic acid probe is a polynucleotide that encodes the ComK polypeptide of SEQ ID NO: 42, or a subsequence thereof. In another preferred aspect, the nucleic acid probe is SEQ ID NO: 41 or its full-length complementary strand.

In another preferred aspect, the nucleic acid probe is a polynucleotide that encodes the ComK polypeptide of SEQ ID NO: 44, or a subsequence thereof. In another preferred aspect, the nucleic acid probe is SEQ ID NO: 43 or its full-length complementary strand.

In another preferred aspect, the nucleic acid probe is a polynucleotide that encodes the ComK polypeptide of SEQ ID NO: 46, or a subsequence thereof. In another preferred aspect, the nucleic acid probe is SEQ ID NO: 45 or its full-length complementary strand.

In another preferred aspect, the nucleic acid probe is a polynucleotide that encodes the ComK polypeptide of SEQ ID NO: 48, or a subsequence thereof. In another preferred aspect, the nucleic acid probe is SEQ ID NO: 47 or its full-length complementary strand.

In another preferred aspect, the nucleic acid probe is a polynucleotide that encodes the ComK polypeptide of SEQ ID NO: 50, or a subsequence thereof. In another preferred aspect, the nucleic acid probe is SEQ ID NO: 49 or its full-length complementary strand.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the isolated polynucleotides encode artificial variants of a ComS polypeptide comprising a substitution, deletion, and/or insertion of one or more amino acids of SEQ ID NO: 2, SEQ ID NO: 4, SEQ ID NO: 6, SEQ ID NO: 8, or SEQ ID NO: 10, or a homologous sequence thereof; or the mature polypeptide thereof.

In another third aspect, the isolated polynucleotides encode artificial variants of a ComK polypeptide comprising a substitution, deletion, and/or insertion of one or more amino acids of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50, or a homologous sequence thereof; or the mature polypeptide thereof.

Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of a ComS polypeptide or ComK polypeptide are altered. For example, amino acid changes may improve the binding affinity and/or binding kinetics of ComS or ComK for MecA, or the binding affinity of ComK for its DNA sequence targets in the genome, and the like.

Essential amino acids in the parent ComS or ComK polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., restriction endonuclease activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145-152; Ner et al., 1988, *DNA* 7: 127-134).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions is preferably 10, more preferably 9, more preferably 8, more preferably 7, more preferably at most 6, more preferably 5, more preferably 4, even more preferably 3, most preferably 2, and even most preferably 1.

Expression of ComS and ComK Polynucleotides

A polynucleotide encoding a ComS polypeptide or a ComK polypeptide can be manipulated in a variety of ways to provide for expression of the polynucleotide in a *Bacillus* host cell. Manipulation of the polynucleotide's sequence prior to its insertion into a nucleic acid construct or vector may be desirable or necessary depending on the nucleic acid construct or vector or *Bacillus* host cell. The techniques for modifying nucleotide sequences utilizing cloning methods are well known in the art.

A nucleic acid construct comprising a polynucleotide encoding a ComS polypeptide or a ComK polypeptide may be operably linked to one or more control sequences capable of directing the expression of the coding sequence in a *Bacillus* host cell under conditions compatible with the control sequences.

Each control sequence may be native or foreign to the polynucleotide encoding a ComS polypeptide or a ComK polypeptide. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding the ComS polypeptide or the ComK polypeptide.

The control sequence may be an appropriate promoter region, a nucleotide sequence that is recognized by a *Bacillus* host cell for expression of the polynucleotide encoding a ComS polypeptide or a ComK polypeptide. The promoter region contains transcription control sequences that mediate the expression of a ComS polypeptide or a ComK polypeptide. The promoter region may be any nucleotide sequence that shows transcriptional activity in the *Bacillus* host cell of choice and may be obtained from genes directing synthesis of extracellular or intracellular polypeptides having biological activity either homologous or heterologous to the *Bacillus* host cell.

The promoter region may comprise a single promoter or a combination of promoters. Where the promoter region comprises a combination of promoters, the promoters are preferably in tandem. A promoter of the promoter region can be any promoter that can initiate transcription of a polynucleotide encoding a polypeptide having biological activity in a *Bacillus* host cell of interest. The promoter may be native, foreign, or a combination thereof, to the nucleotide sequence encoding a polypeptide having biological activity. Such a promoter can be obtained from genes directing synthesis of extracellular or intracellular polypeptides having biological activity either homologous or heterologous to the *Bacillus* host cell.

In a preferred aspect, the promoter region comprises a promoter obtained from a bacterial source. In a more preferred aspect, the promoter region comprises a promoter obtained from a Gram positive bacterium. In another more preferred aspect, the promoter region comprises a promoter obtained from a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

In a most preferred aspect, the promoter region comprises a promoter obtained from a *Bacillus* strain, e.g., *Bacillus agaradherens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or from a *Streptomyces* strain, e.g., *Streptomyces lividans* or *Streptomyces murinus*.

Examples of suitable promoters for directing transcription of a polynucleotide encoding a polypeptide having biological activity in the methods of the present invention are the promoters obtained from the *E. coli* lac operon, *Streptomyces coelicolor* agarase gene (dagA), *Bacillus lentus* or *Bacillus clausii* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, prokaryotic beta-lactamase gene (Villa-Kamaroff et al., 1978, *Proceedings of the National Academy of Sciences USA* 75:3727-3731), and *Bacillus megaterium* xylA gene (Rygus and Hillen, 1992, *J. Bacteriol.* 174: 3049-3055; Kim et al., 1996, *Gene* 181: 71-76), as well as the tac promoter (DeBoer et al., 1983, *Proceedings of the National Academy of Sciences USA* 80: 21-25), the orfβ promoter of plasmid pUB110 (Tortosa et al., 2000, *Mol. Microbiol.* 35: 1110-1119), and the spac promoter (Henner, 1990, *Methods Enzymol.* 185: 223-228). Other examples are the promoter of the spo1 bacterial phage promoter and the tac promoter (DeBoer et al., 1983, *Proceedings of the National Academy of Sciences USA* 80:21-25). Further promoters are described in "Useful proteins from recombinant bacteria" in *Scientific American*, 1980, 242:74-94; and in Sambrook, Fritsch, and Maniatus, 1989, *Molecular Cloning, A Laboratory Manual*, 2d edition, Cold Spring Harbor, N.Y.

In another preferred aspect, the promoter region comprises a promoter that is a "consensus" promoter having the sequence TTGACA for the "−35" region and TATAAT for the "−10" region. The consensus promoter may be obtained from any promoter that can function in a *Bacillus* host cell. The construction of a "consensus" promoter may be accomplished by site-directed mutagenesis using methods well known in the art to create a promoter that conforms more perfectly to the established consensus sequences for the "−10" and "−35" regions of the vegetative "sigma A-type" promoters for *Bacillus subtilis* (Voskuil et al., 1995, *Molecular Microbiology* 17: 271-279).

In another preferred aspect, the promoter region comprises a "consensus" promoter obtained from a promoter obtained from the *E. coli* lac operon, *Streptomyces coelicolor* agarase gene (dagA), *Bacillus clausii* or *Bacillus lentus* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, or prokaryotic beta-lactamase gene spo1 bacterial phage promoter.

In a more preferred aspect, the promoter region comprises a "consensus" promoter obtained from *Bacillus amyloliquefaciens* alpha-amylase gene (amyQ).

In another preferred aspect, the promoter region comprises a promoter that is a hybrid promoter.

In another preferred aspect, the promoter region comprises a promoter that is a variant promoter. See, for example, WO 05/098016, U.S. Pat. No. 5,698,415, and U.S. Pat. No. 6,100,063. In a preferred aspect, the variant promoter is $P_{amyL}4199$, wherein P=promoter In another preferred aspect, the promoter region comprises a promoter that is a tandem promoter. See, for example, WO 99/043835 and WO 05/098016. In a preferred aspect, the tandem promoter is $P_{consensus\ amyQ}$-$P_{cryIIIA}$-cryIIIA mRNA processing/stabilizing sequence. In another preferred aspect, the tandem promoter is $P_{amyL4199}$-$P_{consensus\ amyQ}$-$P_{cryIIIA}$-cryIIIA mRNA processing/stabilizing sequence.

In the methods of the present invention, a hybrid or tandem promoter will be understood to be foreign to a polynucleotide sequence encoding a polypeptide having biological activity even if the wild-type promoter is native to the polynucleotide sequence. For example, in a tandem promoter consisting of at least two promoters, one of the promoters may be a the wild-type promoter of the polynucleotide encoding a biological substance.

The control sequence may also be a suitable transcription terminator sequence, a sequence recognized by a *Bacillus* host cell to terminate transcription. The terminator sequence is operably linked to the 3' terminus of the nucleotide sequence encoding a ComS polypeptide or a ComK polypeptide. Any terminator that is functional in the *Bacillus* host cell of choice may be used in the present invention.

The control sequence may also be a suitable leader sequence, a nontranslated region of a mRNA that is important for translation by the a *Bacillus* host cell. The leader sequence is operably linked to the 5' terminus of the nucleotide sequence directing synthesis of the polypeptide having biological activity. Any leader sequence that is functional in the a *Bacillus* host cell of choice may be used in the present invention.

The control sequence may also be a mRNA stabilizing sequence. The term "mRNA stabilizing sequence" is defined herein as a sequence located downstream of a promoter region and upstream of a coding sequence of a polynucleotide encoding a ComS polypeptide or ComK polypeptide to which the promoter region is operably linked such that all mRNAs synthesized from the promoter region may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, *Journal of Bacteriology* 177: 3465-3471). The mRNA processing/stabilizing sequence is complementary to the 3' extremity of bacterial 16S ribosomal RNA. In a preferred aspect, the mRNA processing/stabilizing sequence generates essentially single-size transcripts with a stabilizing sequence at the 5' end of the transcripts. The mRNA processing/stabilizing sequence is preferably one, which is complementary to the 3' extremity of a bacterial 16S ribosomal RNA. See, U.S. Pat. Nos. 6,255,076 and 5,955,310.

An effective mRNA processing/stabilizing sequence for a *Bacillus* host cells is the *Bacillus thuringiensis* cryIIIA mRNA processing/stabilizing sequence disclosed in WO 94/25612, or portions thereof that retain the mRNA processing/stabilizing function, or the *Bacillus subtilis* SP82 mRNA processing/stabilizing sequence disclosed in Hue et al., 1995, *Journal of Bacteriology* 177: 3465-3471, or portions thereof that retain the mRNA processing/stabilizing function.

The nucleic acid construct can then be introduced into a *Bacillus* host cell using methods known in the art or those methods described herein for expressing the ComS polypeptide or ComK polypeptide.

A nucleic acid construct comprising a DNA of interest encoding or involved in the expression of a substance having biological activity can also be constructed similarly as described above.

For obtaining secretion of the product of the introduced DNA, the control sequence may also be a signal peptide coding region, which codes for an amino acid sequence linked to the amino terminus of a polypeptide that can direct the expressed polypeptide into the cell's secretory pathway. The signal peptide coding region may be native to the polypeptide or may be obtained from foreign sources. The 5' end of the coding sequence of the nucleotide sequence may inherently contain a signal peptide coding region naturally linked in translation reading frame with the segment of the coding region that encodes the secreted polypeptide. Alternatively, the 5' end of the coding sequence may contain a signal peptide coding region that is foreign to that portion of the coding sequence that encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a *Bacillus* species. However, any signal peptide coding region capable of directing the expressed polypeptide into the secretory pathway of a *Bacillus* host cell of choice may be used in the present invention.

An effective signal peptide coding region for a *Bacillus* host cell, is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57:109-137.

Recombinant Expression Vectors

In the methods of the present invention, a recombinant expression vector comprising a polynucleotide encoding a ComS polypeptide or a ComK polypeptide, a promoter, and transcriptional and translational stop signals may be used for the recombinant production of the ComS polypeptide or the ComK polypeptide. The various nucleic acid and control sequences described above may be joined together to produce a recombinant expression vector that may include one or more convenient restriction sites to allow for insertion or substitution of the polynucleotide directing synthesis of the ComS polypeptide or the ComK polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression, and possibly secretion.

The recombinant expression vector may be any vector that can be conveniently subjected to recombinant DNA procedures and can bring about the expression of the nucleotide sequence. The choice of the vector will typically depend on the compatibility of the vector with the *Bacillus* host cell into which the vector is to be introduced. The vectors may be linear or closed circular plasmids. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the *Bacillus* host cell, is integrated into the genome and replicated together with the chromosome(s) into which it has been integrated. The vector system may be a single vector or plasmid or two or more vectors or plasmids that together contain the total DNA to be introduced into the genome of the *Bacillus* cell, or a transposon.

The vectors may be integrated into the genome when introduced into a *Bacillus* host cell. For integration, the vector may rely on the nucleotide sequence directing synthesis of a ComS polypeptide or a ComK polypeptide, or any other element of the vector for stable integration of the vector into the genome by homologous recombination. Alternatively, the vector may contain additional nucleotide sequences for directing integration by homologous recombination into the genome of the *Bacillus* host cell. The additional nucleotide sequences enable the vector to be integrated into the *Bacillus* host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the *Bacillus* host cell. Furthermore, the integrational elements may be non-encoding or encoding nucleotide sequences.

For autonomous replication, the vector may further comprise an origin of replication enabling the vector to replicate autonomously in the *Bacillus* host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in the *Bacillus* host cell (see, e.g., Ehrlich, 1978, *Proceedings of the National Academy of Sciences USA* 75:1433-1436).

More than one copy of a nucleotide sequence directing synthesis of a polypeptide having biological activity, or a ComS polypeptide or a ComK polypeptide, may be introduced into the *Bacillus* host cell to amplify expression of the nucleotide sequence. Stable amplification of the nucleotide sequence can be obtained by integrating at least one additional copy of the sequence into the *Bacillus* host cell genome using methods well known in the art and selecting for transformants. A convenient method for achieving amplification of genomic DNA sequences is described in WO 94/14968.

The vectors preferably contain one or more selectable markers that permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Furthermore, selection may be accomplished by co-transformation, e.g., as described in WO 91/09129, where the selectable marker is on a separate vector.

The procedures used to ligate the elements described above to construct the recombinant expression vectors are well known to one skilled in the art (see, e.g., Sambrook et al., 1989, supra).

A recombinant expression vector comprising a DNA of interest encoding or involved in the expression of a substance having biological activity can also be constructed similarly as described above.

The introduction of a vector into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278).

DNA

In the methods of the present invention, the exogenous DNA transformed into a competent *Bacillus* cell, obtained according to the methods of the present invention, can be any DNA of interest. The DNA may be of genomic, cDNA, semisynthetic, synthetic origin, or any combinations thereof. The DNA may encode any substance having biological activity of interest (hereinafter "biological substance") or may be a DNA involved in the expression of the biological substance, e.g., a promoter.

The substance having a biological activity may be any polypeptide of interest. The polypeptide may be native or heterologous (foreign) to the *Bacillus* host cell of interest. The term "heterologous polypeptide" is defined herein as a polypeptide that is not native to the host cell; a native polypeptide in which structural modifications have been made to alter the native polypeptide, e.g., the protein sequence of a native polypeptide; or a native polypeptide whose expression is quantitatively altered as a result of a manipulation of the DNA encoding the polypeptide by recombinant DNA techniques, e.g., a stronger promoter. The polypeptide may be a naturally occurring allelic and engineered variations of the below-mentioned polypeptides and hybrid polypeptides.

The term "polypeptide" is not meant herein to refer to a specific length of the encoded product and, therefore, encompasses peptides, oligopeptides, and proteins. The term "polypeptide" also encompasses hybrid polypeptides, which comprise a combination of partial or complete polypeptide sequences obtained from at least two different polypeptides wherein one or more may be heterologous to the *Bacillus* cell. Polypeptides further include naturally occurring allelic and engineered variations of a polypeptide.

In a preferred aspect, the polypeptide is an antibody, antigen, antimicrobial peptide, enzyme, growth factor, hormone, immunodilator, neurotransmitter, receptor, reporter protein, structural protein, and transcription factor.

In a more preferred aspect, the polypeptide is an oxidoreductase, transferase, hydrolase, lyase, isomerase, or ligase. In a most preferred aspect, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is an albumin, collagen, tropoelastin, elastin, or gelatin.

In another preferred aspect, the polypeptide is a hybrid polypeptide, which comprises a combination of partial or complete polypeptide sequences obtained from at least two different polypeptides wherein one or more may be heterologous to the *Bacillus* host cell.

In another preferred aspect, the polypeptide is a fused polypeptide in which another polypeptide is fused at the N-terminus or the C-terminus of the polypeptide or fragment thereof. A fused polypeptide is produced by fusing a nucleotide sequence (or a portion thereof) encoding one polypeptide to a nucleotide sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator.

The DNA encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

Techniques used to isolate or clone a DNA encoding a polypeptide of interest are known in the art and include isolation from genomic DNA, preparation from cDNA, or a combination thereof. The cloning of the DNA of interest from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant *Bacillus* cell where multiple copies or clones of the nucleic acid sequence will be replicated. The DNA may be of genomic, cDNA, RNA, semisynthetic, synthetic origin, or any combinations thereof.

A DNA encoding a polypeptide of interest may be manipulated in a variety of ways to provide for expression of the DNA in a suitable *Bacillus* host cell. The construction of nucleic acid constructs and recombinant expression vectors for the DNA encoding a polypeptide of interest can be carried out as described herein for the expression of a ComS polypeptide or a ComK polypeptide.

The DNA can also be a control sequence, e.g., promoter, for manipulating the expression of a gene of interest. Non-limiting examples of control sequences are described herein.

The DNA can further be a nucleic acid construct for inactivating a gene of interest in a *Bacillus* cell.

The DNA is not to be limited in scope by the specific examples disclosed above, since these examples are intended as illustrations of several aspects of the invention.

Methods of Production

The present invention also relates to methods of producing a biological substance, comprising: (a) cultivating a *Bacillus* host cell transformed with an exogenous DNA encoding or involved in the expression of the substance having biological activity under conditions conducive for production of the substance, wherein the *Bacillus* host cell is made competent by at least one copy of an introduced nucleic acid construct comprising a promoter region operably linked to a polynucleotide encoding a ComS polypeptide, wherein the polynucleotide encoding the ComS polypeptide is foreign to the *Bacillus* host cell that was non-competent prior to introduction of the nucleic acid construct; and (b) recovering the substance having biological activity.

In a preferred aspect, the *Bacillus* host cell made competent above further comprises at least one copy of an introduced second nucleic acid construct comprising a promoter region operably linked to a polynucleotide encoding a ComK polypeptide to render the *Bacillus* host cell even further competent.

The competent *Bacillus* host cells are cultivated in a nutrient medium suitable for production of a polypeptide of interest using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide of interest to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted substance of interest, e.g., polypeptide, can be recovered directly from the medium.

The biological substance of interest, e.g., polypeptide, may be detected using methods known in the art that are specific for the substance. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of a polypeptide having enzyme activity. Procedures for determining enzyme activity are known in the art for many enzymes (see, for example, D. Schomburg and M. Salzmann (eds.), *Enzyme Handbook*, Springer-Verlag, New York, 1990).

The resulting biological substance of interest, e.g., polypeptide, may be isolated by methods known in the art. For example, a polypeptide of interest may be isolated from the cultivation medium by conventional procedures including, but not limited to, centrifugation, filtration, extraction, spray-drying, evaporation, or precipitation. The isolated substance of interest may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

Modification of Genes

The present invention also relates to methods of producing a mutant of a parent *Bacillus* cell, which comprises (a) transforming into a parent *Bacillus* cell an exogenous DNA comprising a nucleic acid to modify a gene encoding a polypeptide in the parent *Bacillus* cell, which results in a mutant cell producing less of the polypeptide or producing a polypeptide with lower biological activity than the parent cell when cultivated under the same conditions, wherein the parent *Bacillus* cell is made competent by at least one copy of an introduced first nucleic acid construct comprising a promoter region operably linked to a polynucleotide encoding a ComS polypeptide, wherein the polynucleotide encoding the ComS polypeptide is foreign to the parent *Bacillus* cell that was non-competent prior to introduction of the first nucleic acid construct; and (b) isolating the mutant cell.

In a preferred aspect, the modification is an inactivation of a gene eliminating production of its product.

In another preferred aspect, the *Bacillus* cell made competent above further comprises at least one copy of an introduced second nucleic acid construct comprising a promoter region operably linked to a polynucleotide encoding a ComK polypeptide to render the *Bacillus* cell even further competent.

The mutant cell comprising a modified gene may be constructed using methods well known in the art, for example, insertions, disruptions, replacements, or deletions. The gene to be modified may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the gene. Other control sequences for possible modification include, but are not limited to, a leader, polyadenylation sequence, propeptide sequence, signal peptide sequence, transcription terminator, and transcriptional activator.

Modification of the gene may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame.

An example of a convenient way to modify a gene is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

The *Bacillus* mutant cells so created are particularly useful as host cells for the expression of polypeptides native or foreign to the cells. Therefore, the present invention further relates to methods of producing a native or foreign polypeptide comprising: (a) cultivating the mutant cell under conditions conducive for production of the polypeptide; and (b) recovering the polypeptide. The term "foreign polypeptide" is defined herein as a polypeptide that is not native to the host cell, a native protein in which modifications have been made to alter the native sequence, or a native protein whose expression is quantitatively altered as a result of a manipulation of the host cell by recombinant DNA techniques.

Examples of polypeptides that can expressed in such mutants are described herein.

The methods used for cultivation and purification of the product of interest may be performed by methods known in the art and described herein.

The present invention is further described by the following examples that should not be construed as limiting the scope of the invention.

EXAMPLES

DNA Sequencing

DNA sequencing was performed using an Applied Biosystems Model 3130X Genetic Analyzer (Applied Biosystems, Foster City, Calif., USA) using dye terminator chemistry (Giesecke et al., 1992, *Journal of Virol. Methods* 38: 47-60). Sequences were assembled using phred/phrap/consed (University of Washington, Seattle, Wash., USA) with sequence specific primers.

*Escherichia Coli* Strains

ONE SHOT® TOP10 chemically competent *E. coli* cells (Invitrogen Corporation, Carlsbad, Calif., USA), SURE® Competent *E. coli* cells (Stratagene, La Jolla, Calif., USA), XL1-Blue competent *E. coli* cells (Stratagene, La Jolla, Calif., USA), and SOLOPACK® Gold supercompetent *E. coli* cells (Stratagene, La Jolla, Calif., USA) were used for routine plasmid constructions and propagation.

*Bacillus* Strains

*Bacillus subtilis* 168Δ4 is derived from the *Bacillus subtilis* type strain 168 (BGSC 1A1, *Bacillus* Genetic Stock Center, Columbus, Ohio, USA) and has deletions in the spoIIAC, aprE, nprE, and amyE genes. The deletion of these four genes was performed essentially as described for *Bacillus subtilis* A164Δ5, which is described in detail in U.S. Pat. No. 5,891,701. Tryptophan, at 50 μg/ml, was supplemented to cultures of *Bacillus subtilis* 168Δ4.

All temperature-sensitive plasmids were constructed in *Bacillus subtilis* 168Δ4 (*Bacillus subtilis* 168 ΔsigF ΔaprE ΔnprE amyE). *Bacillus subtilis* A164Δ5 (*Bacillus subtilis* A164 ΔspoIIAC, ΔaprE, ΔnprE, ΔamyE, ΔsrfAC) was used as a host to assess the effects of *Bacillus licheniformis* comK overexpression on the transformation efficiency of *Bacillus subtilis. Bacillus subtilis* strain MDT101, described herein, which expresses the DNA methyltransferase component of the *Bacillus licheniformis* SJ1904 restriction-modification system was used for modifying plasmid DNA prior to transformation experiments. *Bacillus licheniformis* SJ1904 (U.S. Pat. No. 5,733,753) was used as a host for expression of the *Bacillus subtilis* comS gene, for increased expression of the *Bacillus licheniformis* comK gene, and for subsequent induction of a competent state in *Bacillus licheniformis.*

*Bacillus subtilis* was transformed according to the procedure of Anagnostopoulos and Spizizen, 1961, *J. Bacteriol.* 81: 741-746. *Bacillus licheniformis* strain SJ1904 was transformed by electroporation, according to the procedure of Susanna et al., 2004, *J. Bacteriol.* 186: 1120-1128. Restriction-proficient *Bacillus licheniformis* strains were transformed with plasmid DNA that had been methylated in order to render it resistant to restriction in *Bacillus licheniformis*. In order to provide proper methylation, DNA was isolated from a previous transformant of *Bacillus subtilis* MDT101.

Media

2×YT plates were composed per liter of 16 g tryptone, 10 g of yeast extract, 5 g of NaCl, and 15 g of bacto agar.

2×YT ampicillin plates were composed per liter of 16 g tryptone, 10 g of yeast extract, 5 g of NaCl, and 15 g of bacto agar supplemented with 100 μg of ampicillin per ml.

TBAB was composed of Tryptose Blood Agar Base (Difco Laboratories, Sparks, Md., USA).

LB medium was composed per liter of 10 g of tryptone, 5 g of yeast extract, and 5 g of NaCl.

LB plates were composed of LB medium and 15 g of bacto agar per liter.

LB erythromycin medium was composed of LB medium containing 5 μg of erythromycin per ml.

LB erythromycin/lincomycin plates were composed of LB medium and 1 μg of erythromycin and 25 μg of lincomycin per ml.

LB chloramphenicol plates were composed of LB medium and 5 μg of chloramphenicol per ml.

LB erythromycin/chloramphenicol plates were composed of LB medium and 1 μg of erythromycin and 5 μg of chloramphenicol per ml.

VY medium was composed per liter of 25 g of veal infusion (BD Diagnostics, Franklin Lakes, N.J., USA) and 5 g of yeast extract.

Spizizen I medium was composed of 1× Spizizen salts, 0.5% glucose, 0.1% yeast extract, and 0.02% casein hydrolysate. This medium is also referred to herein as minimal medium.

1× Spizizen salts was composed per liter of 6 g of $KH_2PO_4$, 14 g of $K_2HPO_4$, 2 g of $(NH_4)_2SO_4$, 1 g of sodium citrate, and 0.2 g of $MgSO_4$, pH 7.0.

Spizizen II medium was composed of Spizizen I medium supplemented with 0.5 mM $CaCl_2$ and 2.5 mM $MgCl_2$.

TBAB erythromycin/lincomycin plates were composed of TBAB medium and 1 μg of erythromycin and 25 μg of lincomycin per ml.

Example 1

Determination of the Genome Sequence for *Bacillus licheniformis* Strain SJ1904

The genome sequence for the entire chromosome of *Bacillus licheniformis* strain SJ1904 was determined from contigs generated using 454 DNA sequencing technology (Margulies et al., 2005, *Nature* 437: 376-380), random paired reads using Sanger sequencing technology, and, to close gaps and resolve repeats, reads from PCR fragments of genomic DNA. Sequencing data was assembled using Phrap, and edited and viewed in Consed. Gene models were predicted from the genomic DNA sequence using Glimmer (Delcher et al., 1999, *Nucleic Acids Research* 27: 4636-4641). Gene models were machine annotated by comparison to the nonredundant database PIR-NREF (Wu et al., 2002, *Nucleic Acids Research* 30: 35-37) using a BLASTP with an E-value threshold of $1\times10^{-5}$.

Example 2

Identification of *Bacillus licheniformis* M.Bli1904II DNA Methyltransferase Gene The deduced amino acid sequences for the *Bacillus licheniformis* strain SJ1904 gene models were compared to the protein sequences from REBASE (Roberts, R. J., Macelis, M., Rebase. 2005) using BLASTP (Altschul et al., 1997, *Nucleic Acids Research* 25: 3389-3402). As the DNA methyltransferases have a moderate level of sequence conservation, this analysis identified all putative DNA methyltransferases in this genome. A cytosine-specific DNA methyltransferase signature was identified within M.Bli1904II using Prints-S version 16 as implemented through InterProScan release v3.3. In addition, six highly conserved motifs found in cytosine-specific DNA methyltransferases (Kumar et al., 1994, *Nucleic Acids Research* 22 1-10) were found to be conserved in the *Bacillus licheniformis* M.Bli1904II DNA methyltransferase.

Example 3

Characterization of the *Bacillus licheniformis* M.Bli1904II DNA Methyltransferase Gene The nucleotide sequence (SEQ ID NO: 51) and deduced amino acid sequence (SEQ ID NO: 52) of the *Bacillus licheniformis* M.Bli1904II DNA methyltransferase gene are shown in FIGS. 2A and 2B. The coding sequence is 1014 bp including the stop codon. The coding region is 36.1% G+C. The encoded predicted protein is 337 amino acids with a molecular mass of 38.5 kDa.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Bacillus licheniformis* M.Bli1904II DNA methyltransferase shared 64% identity with a *Bacillus weihenstephanensis* C-5 cytosine-specific DNA methyltransferase precursor (UniRef100_Q2AVE0) and shared 47% identity with an *Oceanobacillus iheyensis* cytosine-specific DNA methyltransferase (UniRef100_Q8EL98). When the output of Needle labeled "longest identity" was used as the percent identity and was calculated as follows:

$$(\text{Identical Residues}\times100)/(\text{Length of Alignment}-\text{Number of Gaps in Alignment})$$

the deduced amino acid sequence of the *Bacillus licheniformis* M.Bli1904II DNA methyltransferase shared 68.5% identity with the *Bacillus* weihenstephanensis C-5 cytosine-specific DNA methyltransferase precursor (UniRef100_Q2AVE0) and 55.9% identity with the *Oceanobacillus iheyensis* cytosine-specific DNA methyltransferase (UniRef100_Q8EL98).

Example 4

Cloning of the *Bacillus licheniformis* M.Bli1904II DNA Methyltransferase Gene The *Bacillus licheniformis* DNA methyltransferase M.Bli1904II gene was cloned by PCR for expression in *Bacillus subtilis*.

Genomic DNA was isolated from *Bacillus licheniformis* SJ1904 according to the procedure of Pitcher et al., 1989, *Lett. Appl. Microbiol.* 8: 151-156. FIG. 3 shows the region of the *Bacillus licheniformis* chromosome comprising the genes encoding the Bli1904II restriction endonuclease and M.Bli1904II DNA methyltransferase. An approximately 1043 bp fragment of the *Bacillus licheniformis* SJ1904 chromosome including the ribosome binding site and coding region of the M.Bli1904II DNA methyltransferase gene, comprising nucleotides 2019-3049 of SEQ ID NO: 53 (FIGS. 3A, 3B, and 3C), was amplified by PCR from *Bacillus licheniformis* SJ1904 genomic DNA using primers 999611 and 999612 shown below. Primer 999611 incorporates a Sac I restriction site, and primer 999612 incorporates an Mlu I restriction site.

```
Primer 999611:
                                     (SEQ ID NO: 54)
5'-GAGCTCTGCAAGGAGGTATAATTTTG-3'

Primer 999612:
                                     (SEQ ID NO: 55)
5'-ACGCGTTTATTCAGCTATTGCATATTC-3'
```

The PCR was performed using Pfx PLATINUM® DNA Polymerase (Invitrogen, Carlsbad, Calif., USA). The amplification reaction (50 μl) was composed of 1× Pfx Amplification Buffer (Invitrogen, Carlsbad, Calif., USA), 1 mM $MgSO_4$, 300 μM of each dNTP, 0.3 μM of each primer, 1.25 units of PLATINUM® Pfx DNA Polymerase, and approximately 200 ng of template DNA. The reaction was performed using a ROBOCYCLER® 40 Temperature Cycler (Stratagene Corporation, La Jolla, Calif., USA) programmed for 1 cycle at 95° C. for 2 minutes; 30 cycles each at 95° C. for 1 minute, 55° C. for 1 minute, and 68° C. for 1 minute; and 1 cycle at 68° C. for 3 minutes.

Figure 4:
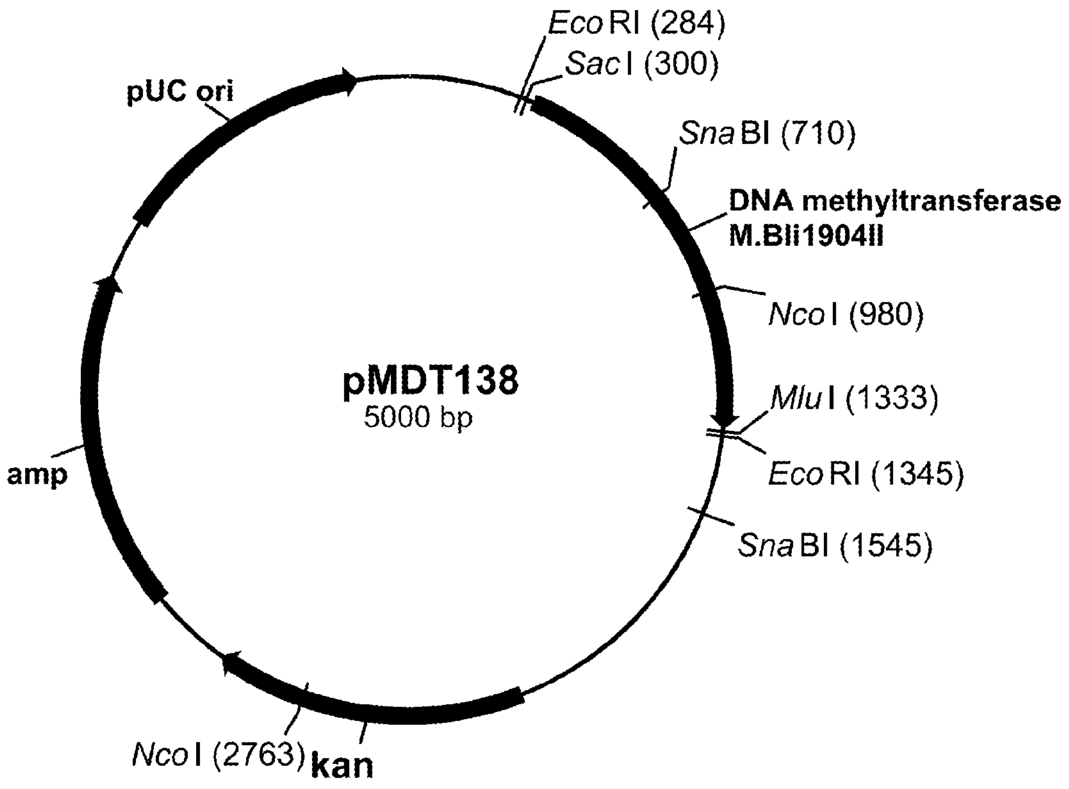
FIG. 4 shows a restriction map of pMDT138.

The resulting PCR product of approximately 1043 bp was cloned into vector pCR4Blunt using a ZERO BLUNT® TOPO® PCR Cloning Kit for Sequencing (Invitrogen, Carlsbad, Calif., USA) and transformed into ONE SHOT® TOP10 Chemically Competent *E. coli* cells according to the manufacturer's instructions. Plasmid DNA was isolated from one transformant using a Plasmid Midi Kit (QIAGEN Inc., Valencia, Calif., USA) and confirmed by digestions with Eco RI, Nco I, and Sna BI followed by 0.8% agarose electrophoresis in TBE (50 mM Tris base-50 mM boric acid-1 mM disodium EDTA) buffer, which yielded expected fragments of 3939 bp and 1061 bp for Eco RI; 3217 bp and 1783 bp for Nco I; and 4165 bp and 835 bp for Sna BI. The DNA sequence of the cloned PCR fragment was confirmed by DNA sequencing. This plasmid was designated pMDT138 (FIG. 4).

Plasmid pMDT138 was transformed into *E. coli* XL1-Blue cells (Stratagene Corporation, La Jolla, Calif., USA) according to the manufacturer's instructions, selecting for ampicillin resistance on 2×YT ampicillin plates at 37° C. One transformant was designated MDT45 and was deposited on Sep. 7, 2006, under the terms of the Budapest Treaty with the Agricultural Research Service Patent Culture Collection, Northern Regional Research Center, 1815 University Street, Peoria, Ill., 61604, and given the accession number NRRL B-41967.

Example 5

Construction of pMDT100

Plasmid pMDT100 is an *E. coli* replicon containing the $P_{amyL4199}$/$P_{short\ consensus\ amyQ}$/$P_{cryIIIA}$/cryIIIAstab triple tandem promoter driving expression of the *Bacillus clausii* alkaline protease gene (aprH). This aprH expression cassette and the cat gene of pC194 (Horinouchi and Weisblum, 1982, *J. Bacteriol.* 150: 804-814) are flanked on both sides by fragments of the *Bacillus subtilis* alpha-amylase (amyE) gene, permitting insertion of the aprH expression cassette and cat gene at the amyE locus of the *Bacillus subtilis* chromosome by double homologous recombination via the two amyE fragments. Replacement of the aprH gene in pMDT100 with another gene allows chromosomal insertion and expression of that gene in *Bacillus subtilis*. The construction of pMDT100 is described below.

Plasmid pNBT51.

Figure 5:
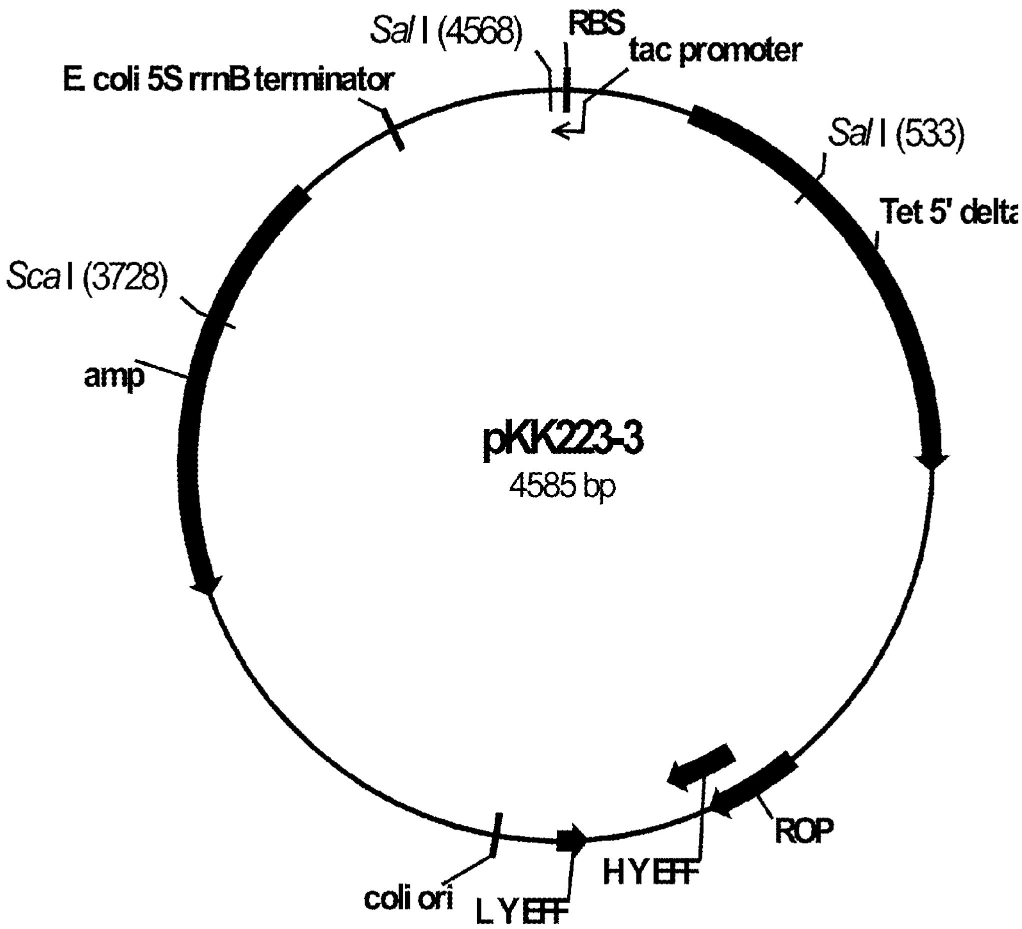
FIG. 5 shows a restriction map of pKK223-3.
Figure 6:
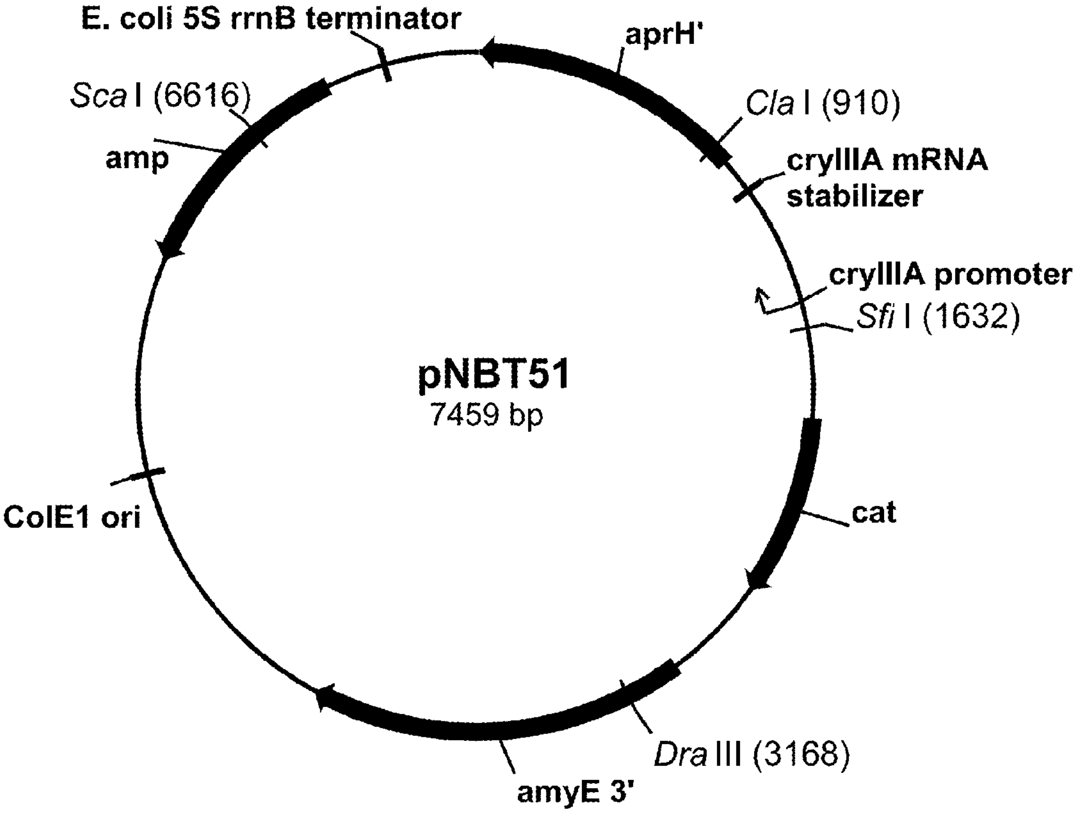
FIG. 6 shows a restriction map of pNBT51.

Plasmid pNBT10 (pDG268MCS-$Pr_{cryIIIA}$/cryIIIAstab/SAV; U.S. Pat. No. 6,255,076) was isolated from *E. coli* DH5α host, using a QIAGEN® Plasmid Kit (QIAGEN Inc., Valencia, Calif., USA) according to the manufacturer's instructions, and digested with Cla I and Sca I. Cleavage occurred at the Cla I site at approximately codon 326 of the aprH coding sequence and not at the Cla I site at approximately codon 23, which was blocked by methylation due to *E. coli* Dam DNA methyltransferase. The Cla I ends were blunted using Klenow fragment (New England Biolabs, Inc., Beverly, Mass., USA) and dNTPs according to the manufacturer's instructions. The digested plasmid was analyzed by 0.8% agarose electrophoresis with TBE buffer, and a vector fragment of approximately 6615 bp was purified using a QIAQUICK® Gel Extraction Kit (QIAGEN Inc., Valencia, Calif., USA). Plasmid pOS4301 (Bacillus Genetic Stock Center, Ohio State University, Columbus, Ohio, USA) was digested with Sal I and Sca I, and the Sal I ends were blunted using Klenow fragment and dNTPs, as described above. The digested plasmid was analyzed by 0.8% agarose electrophoresis in TBE buffer, and a fragment of approximately 840 bp bearing the *E. coli* rrnB transcription terminator was purified using a QIAQUICK® Gel Extraction Kit. The same 840 bp Sal I/Sca I fragment could be isolated from the vector pKK223-3 (GE Healthcare, Piscataway, N.J., USA) (FIG. 5). The pNBT10 vector fragment and terminator-bearing fragment were ligated together with T4 DNA ligase (Roche Diagnostics Corporation, Indianapolis, Ind., USA) according to the manufacturer's instructions, and *E. coli* DH5α (Gibco BRL, Gaithersburg, Md., USA) was transformed with the ligation according to the manufacturer's instructions, selecting for ampicillin resistance on 2×YT ampicillin plates at 37° C. The resulting plasmid was designated pNBT51 (pDG268-$P_{cryIIIA}$/cryIIIAstab/SAVΔ) (FIG. 6).

Plasmid pNBT52.

Figure 7:
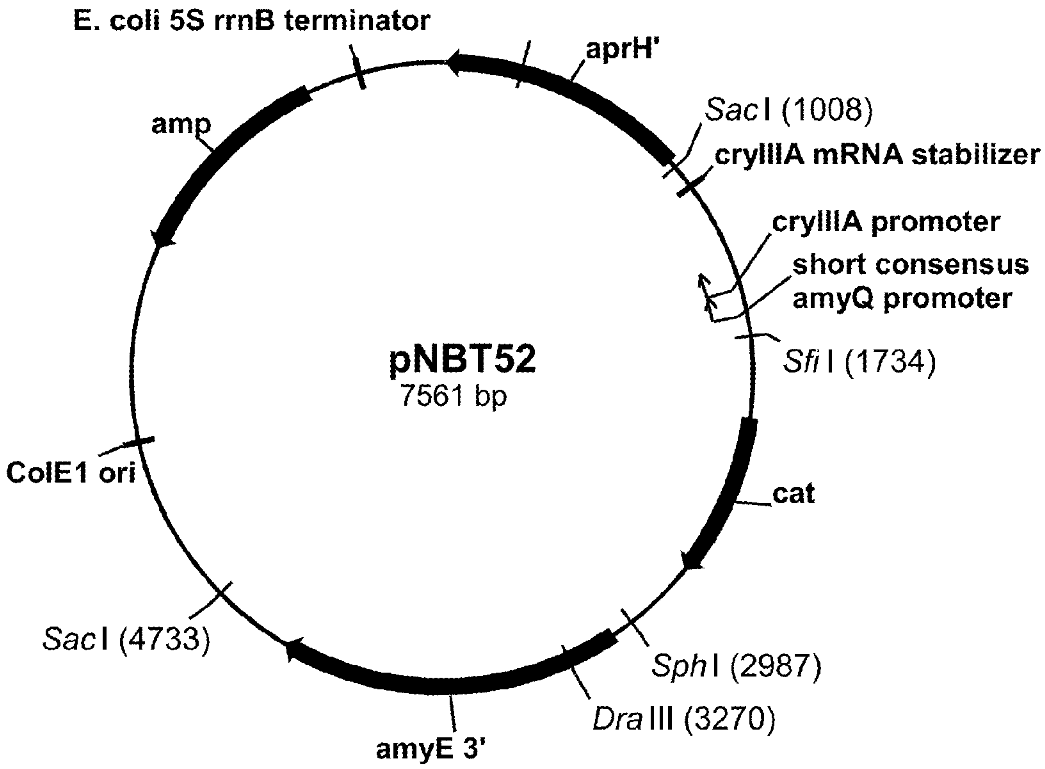
FIG. 7 shows a restriction map of pNBT52.

Plasmid pNBT51 was digested with Sfi I, and the ends were blunted by incubation for 20 minutes at 11° C. with T4 DNA polymerase (Roche Diagnostics Corporation, Indianapolis, Ind., USA) and 25 μM of each dNTP, followed by heat-inactivation of the polymerase by incubation for 10 minutes at 75° C. The blunt-ended plasmid was then digested with Dra III and analyzed by 0.8% agarose electrophoresis in TBE buffer, and a vector fragment of approximately 5920 bp was purified using a QIAQUICK® Gel Extraction Kit. Plasmid pNBT20 (pDG268MCS-$P_{short\ consensus\ amyQ}$/SAV; U.S. Pat. No. 6,255,076) was digested with Dra III and Ecl 136II, and a fragment of approximately 1641 bp bearing a short consensus amyQ promoter ($P_{short\ consensus\ amyQ}$) was purified using a QIAQUICK® Gel Extraction Kit. The pNBT51 vector fragment and $P_{short\ consensus\ amyQ}$ fragment were ligated as described above, and *E. coli* DH5α was transformed with the ligation as described above, selecting for ampicillin resistance on 2×YT ampicillin plates at 37° C. Plasmid DNA was isolated from several transformants using a QIAPREP® 8 Miniprep Kit (QIAGEN Inc. Valencia, Calif., USA), digested with Sph I, and analyzed by 0.8% agarose electrophoresis in TBE buffer. One plasmid with expected restriction fragments of approximately 4873 bp and 2688 bp was designated pNBT52 (pDG268-$P_{short\ consensus\ amyQ}$/$P_{cryIIIA}$/cryIIIAstab/SAVΔ) (FIG. 7).

Plasmid pNBT53.

Figure 8:
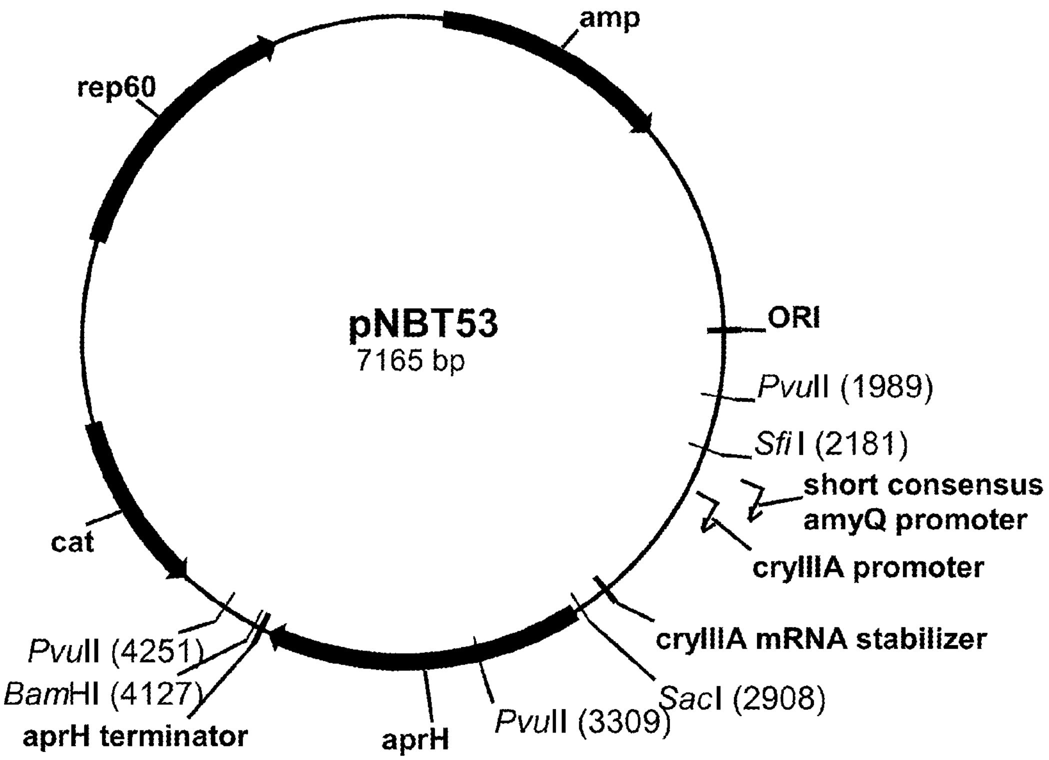
FIG. 8 shows a restriction map of pNBT53.

Plasmid pNBT6 (pHP 13 amp-SAV; U.S. Pat. No. 6,255,076) was digested with Sfi I and Sac I and analyzed by 0.8% agarose electrophoresis in TBE buffer, and a vector fragment of approximately 6438 bp was purified using a QIAQUICK® Gel Extraction Kit. Plasmid pNBT52 was digested with Sfi I and Sac I and analyzed by 0.8% agarose electrophoresis in TBE buffer, and a fragment of approximately 727 bp bearing the $P_{short\ consensus\ amyQ}$/$P_{cryIIIA}$/cryIIIAstab tandem promoter was purified using a QIAQUICK® Gel Extraction Kit. The pNBT6 vector fragment and $P_{short\ consensus\ amyQ}$/$P_{cryIIIA}$/cryIIIAstab fragment were ligated as described above, and *E. coli* DH5α cells were transformed with the ligation as described above, selecting for ampicillin resistance on 2×YT ampicillin plates at 37° C. Plasmid DNA was isolated from several transformants using a QIAPREP® 8 Miniprep Kit, digested with Pvu II, and analyzed by 0.8% agarose electrophoresis using TBE buffer. One plasmid with expected restriction fragments of approximately 4903 bp, 1320 bp, and 942 bp was designated pNBT53 (pHP13 amp-$P_{short\ consensus\ amyQ}$/$P_{cryIIIA}$/cryIIIAstab/SAV) (FIG. 8).

Plasmid pNBT54.

Figure 9:
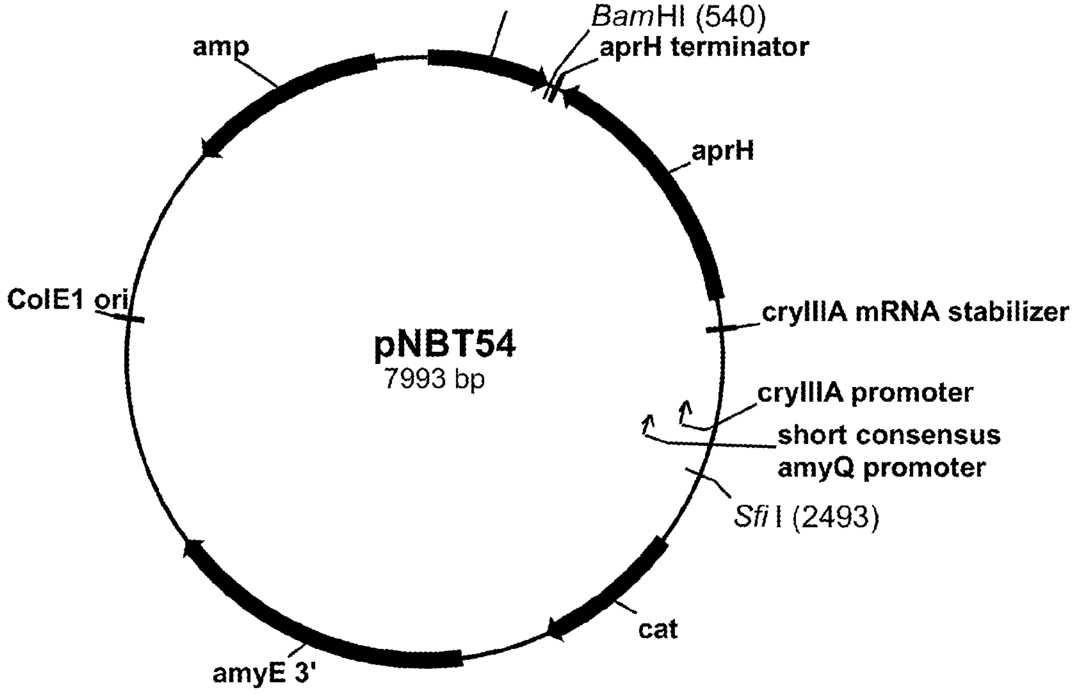
FIG. 9 shows a restriction map of pNBT54.

Plasmid pNBT1 (pDG268MCS; U.S. Pat. No. 6,255,076) was digested with Sfi I and Bam HI and analyzed by 0.8% agarose electrophoresis in TBE buffer, and a vector fragment of approximately 6040 bp was purified using a QIAQUICK® Gel Extraction Kit. Plasmid pNBT53 was digested with Sfi I and Bam HI and analyzed by 0.8% agarose electrophoresis using TBE buffer, and a fragment of approximately 1953 bp bearing the $P_{short\ consensus\ amyQ}$/$P_{cryIIIA}$/cryIIIAstab/SAV cassette was purified using a QIAQUICK® Gel Extraction Kit. The pNBT1 vector fragment and $P_{short\ consensus\ amyQ}$/$P_{cryIIIA}$/cryIIIAstab/SAV fragment were ligated as described above, and *E. coli DH*5α cells were transformed with the ligation as described above, selecting for ampicillin resistance on 2×YT ampicillin plates at 37° C. Plasmid DNA was isolated from several transformants using a QIAPREP® 8 Miniprep Kit and analyzed by simultaneous digestion with Sfi I and Bam HI followed by 0.8% agarose gel electrophoresis in TBE buffer. One plasmid with expected restriction fragments of approximately 6040 bp and 1953 bp was designated pNBT54 (pDG268MCS-$P_{short}$ consensus amyQ/$P_{cryIIIA}$/cryIIIAstab/SAV) (FIG. 9).

Plasmid pNBT35.

Figure 10:
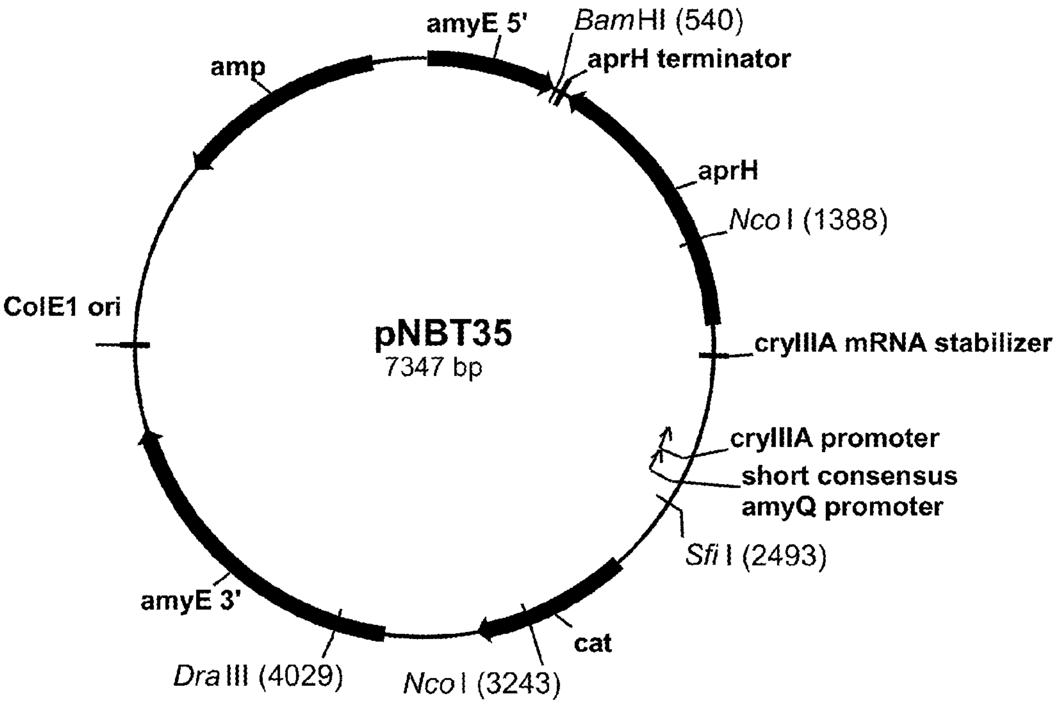
FIG. 10 shows a restriction map of pNBT35.

Plasmid pNBT2 (pDG268MCSΔ-$Pr_{cryIIIA}$/cryIIIAstab/SAV; U.S. Pat. No. 6,255,076) was digested with Sfi I and Bam HI and analyzed by 0.8% agarose gel electrophoresis in TBE buffer, and a vector fragment of approximately 5394 bp was purified using a QIAQUICK® Gel Extraction Kit. Plasmid pNBT54 was digested with Sfi I and Bam HI, and analyzed by 0.8% agarose gel electrophoresis in TBE buffer, and a fragment of approximately 1953 bp bearing the $P_{short\ consensus\ amyQ}$/$P_{cryIIIA}$/cryIIIAstab/SAV cassette was purified using a QIAQUICK® Gel Extraction Kit. The pNBT2 vector fragment and $P_{short\ consensus\ amyQ}$/$P_{cryIIIA}$/cryIIIAstab/SAV fragment were ligated as described above, and *E. coli* DH5α cells were transformed with the ligation as described above, selecting for ampicillin resistance on 2×YT ampicillin plates at 37° C. Plasmid DNA was isolated from several transformants using a QIAPREP® 8 Miniprep Kit, digested with Nco I, and analyzed by 0.8% agarose gel electrophoresis in TBE buffer. One plasmid with expected restriction fragments of approximately 5492 bp and 1855 bp was designated pNBT35 (pDG268MCSΔ-$P_{short\ consensus\ amyQ}$/$P_{cryIIIA}$/cryIIIAstab/SAV) (FIG. 10).

Plasmid pNBT30.

Plasmid pNBT30 was constructed to contain a PCR clone of the amyL4199 variant of the amyL gene promoter (U.S. Pat. No. 6,100,063). *Bacillus licheniformis* SJ1904 genomic DNA was isolated according to the procedure of Pitcher et al., 1989, supra. The amyL4199 promoter ($P_{amyL}$4199) gene was amplified by PCR from *Bacillus licheniformis* SJ1904 genomic DNA using primers 950872 and 991151 shown below. Primer 950872 incorporates an Sfi I restriction site, and primer 991151 incorporates a Sac I restriction site and the variant nucleotides of $P_{amyL4199}$.

```
Primer 950872:
                                        (SEQ ID NO: 56)
5'-CCAGGCCTTAAGGGCCGCATGCGTCCTTCTTTGTGCT-3'

Primer 991151:
                                        (SEQ ID NO: 57)
5'-GAGCTCCTTTCAATGTGATACATATGA-3'
```

The PCR was performed using AMPLITAQ® Gold DNA Polymerase (Applied Biosystems, Foster City, Calif., USA) according to manufacturer's recommendations, except that the $MgCl_2$ concentration was 3 mM, rather than the standard 1.5 mM. The amplification reaction (50 μl) was composed of 10 mM Tris-HCl (pH 8.3), 50 mM KCl, 3.0 mM $MgCl_2$, 200 μM of each dNTP, 0.5 μM of each primer, 0.25 units of AMPLITAQ® Gold DNA Polymerase, and approximately 200 ng of template DNA. The PCR was performed in a ROBOCYCLER® 40 Temperature Cycler programmed for 1 cycle at 95° C. for 9 minutes; 30 cycles each at 95° C. for 1 minute, 55° C. for 1 minute, and 72° C. for 1 minute; and 1 cycle at 72° C. for 3 minutes.

Figure 11:
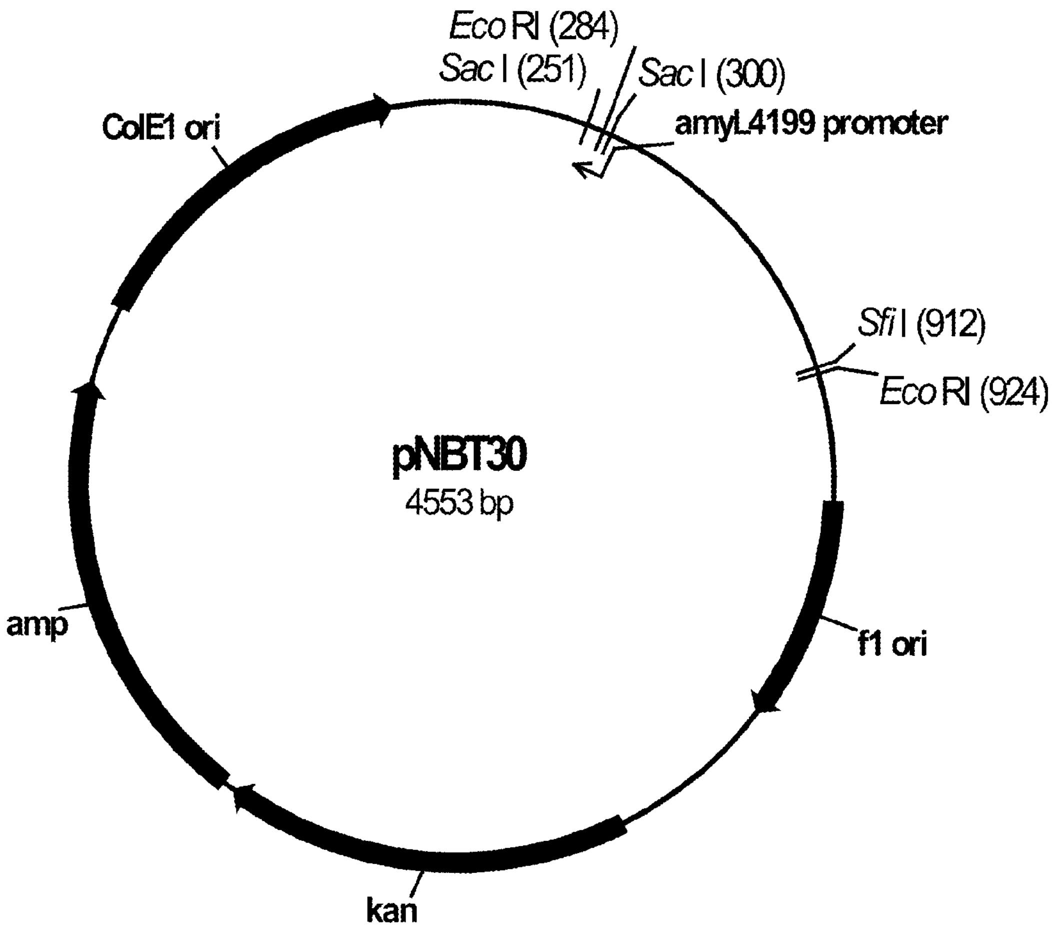
FIG. 11 shows a restriction map of pNBT30.

The resulting PCR product of approximately 625 bp was cloned into vector pCR2.1 using a TOPO® TA Cloning Kit (Invitrogen, Carlsbad, Calif., USA) and transformed into ONE SHOT® TOP10 Chemically Competent *E. coli* cells (Invitrogen, Carlsbad, Calif., USA) according to the manufacturer's instructions. Plasmid DNA was isolated from several transformants using a QIAPREP® 8 Miniprep Kit and analyzed for the presence of the cloned PCR fragment by digestion with Eco RI followed by 0.8% agarose electrophoresis in TBE buffer. One plasmid with expected restriction fragments of approximately 3913 bp and 640 bp was designated pNBT30 (pCR2.1-amyL4199) (FIG. 11). The DNA sequence of the cloned PCR fragment was confirmed by DNA sequencing.

Plasmid pNBT31.

Figure 12:
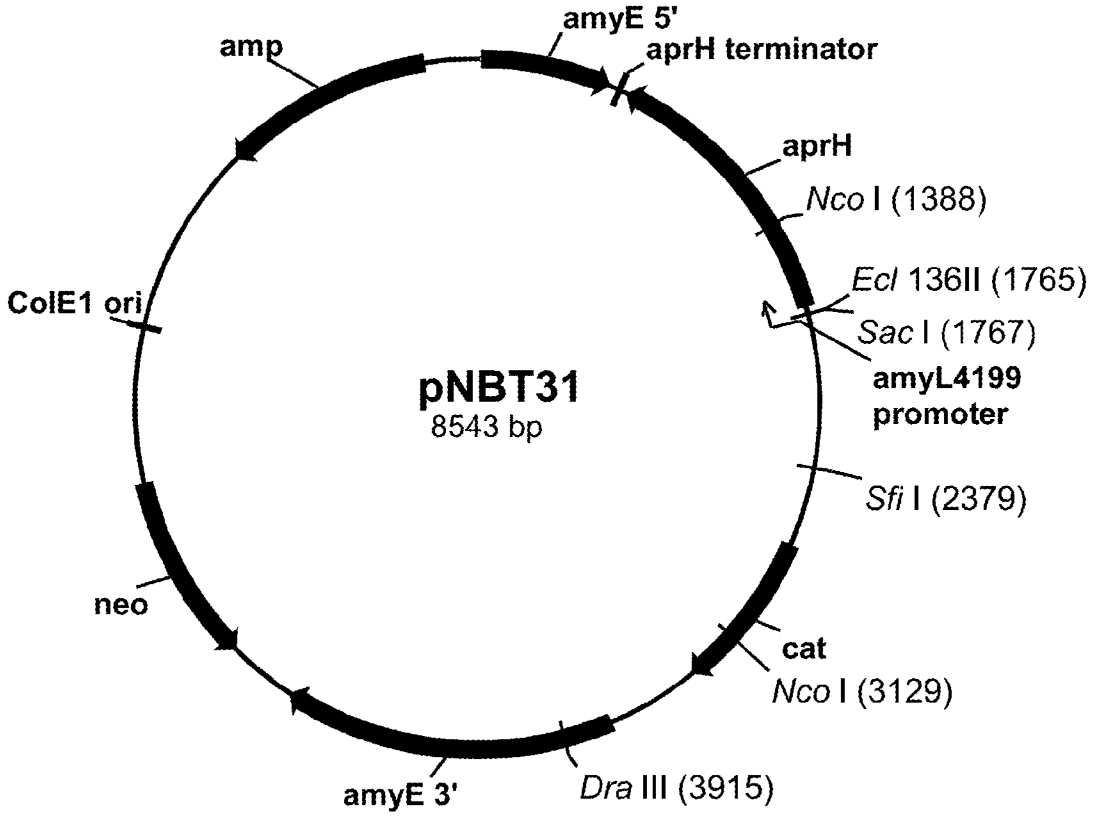
FIG. 12 shows a restriction map of pNBT31.

Plasmid pNBT3 (pDG268MCSΔneo-$Pr_{cryIIIA}$/cryIIIAstab/SAV; U.S. Pat. No. 6,255,076) was digested with Sfi I and Sac I and analyzed by 0.8% agarose electrophoresis in TBE buffer, and a vector fragment of approximately 7931 bp was purified using a QIAQUICK® Gel Extraction Kit. Plasmid pNBT30 was digested with Sfi I and Sac I, analyzed by 0.8% agarose electrophoresis in TBE buffer, and a fragment of approximately 612 bp bearing $P_{amyL4199}$ was purified using a QIAQUICK® Gel Extraction Kit. The pNBT3 vector fragment and $P_{amyL4199}$ fragment were ligated as described above, and *E. coli* XL1-Blue cells (Stratagene Corporation, La Jolla, Calif., USA) were transformed with the ligation according to the manufacturer's instructions, selecting for ampicillin resistance on 2×YT ampicillin plates at 37° C. Plasmid DNA was isolated from several transformants using a QIAPREP® 8 Miniprep Kit, digested with Nco I, and analyzed by 0.8% agarose electrophoresis in TBE buffer. One plasmid with expected restriction fragments of approximately 6802 bp and 1741 bp was designated pNBT31 (FIG. 12).

Plasmid pNBT36.

Figure 13:
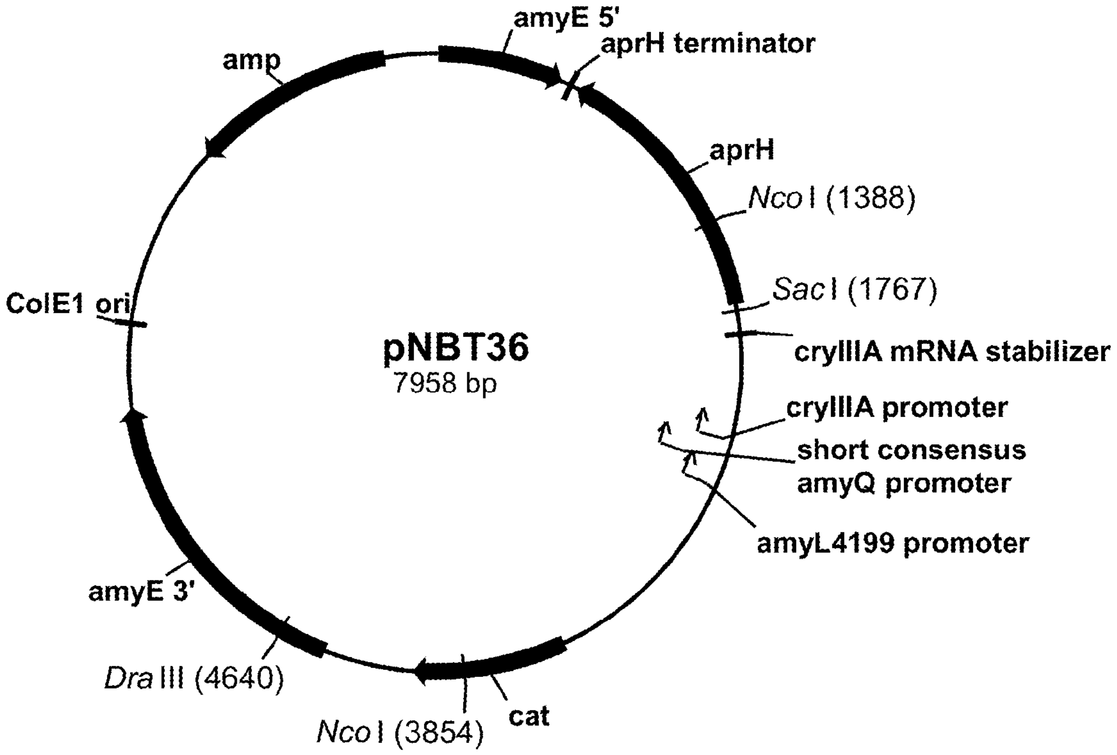
FIG. 13 shows a restriction map of pNBT36.

Plasmid pNBT35 was digested with Sfi I, and the ends were blunted using T4 DNA polymerase and dNTPs, as described above. The blunt ended plasmid was then digested with Dra III, and analyzed by 0.8% agarose electrophoresis in TBE buffer. A vector fragment of approximately 5808 bp was purified using a QIAQUICK® Gel Extraction Kit. Plasmid pNBT31 was digested with Dra III and Ecl 13611, analyzed by 0.8% agarose electrophoresis in TBE buffer, and a fragment of approximately 2150 bp bearing $P_{amyL4199}$ was purified using a QIAQUICK® Gel Extraction Kit. The pNBT35 vector fragment and $P_{amyL4199}$ fragment were ligated as described above, and *E. coli* SURE® cells (Stratagene Corporation, La Jolla, Calif., USA) were transformed with the ligation according to the manufacturer's instructions, selecting for ampicillin resistance on 2×YT ampicillin plates at 37° C. Plasmid DNA was isolated from several transformants using a QIAPREP® 8 Miniprep Kit, digested with Nco I, and analyzed by 0.8% agarose electrophoresis in TBE buffer. One plasmid with expected restriction fragments of approximately 5492 bp and 2466 bp was designated pNBT36 (FIG. 13).

Plasmid pMDT100.

Figure 14:
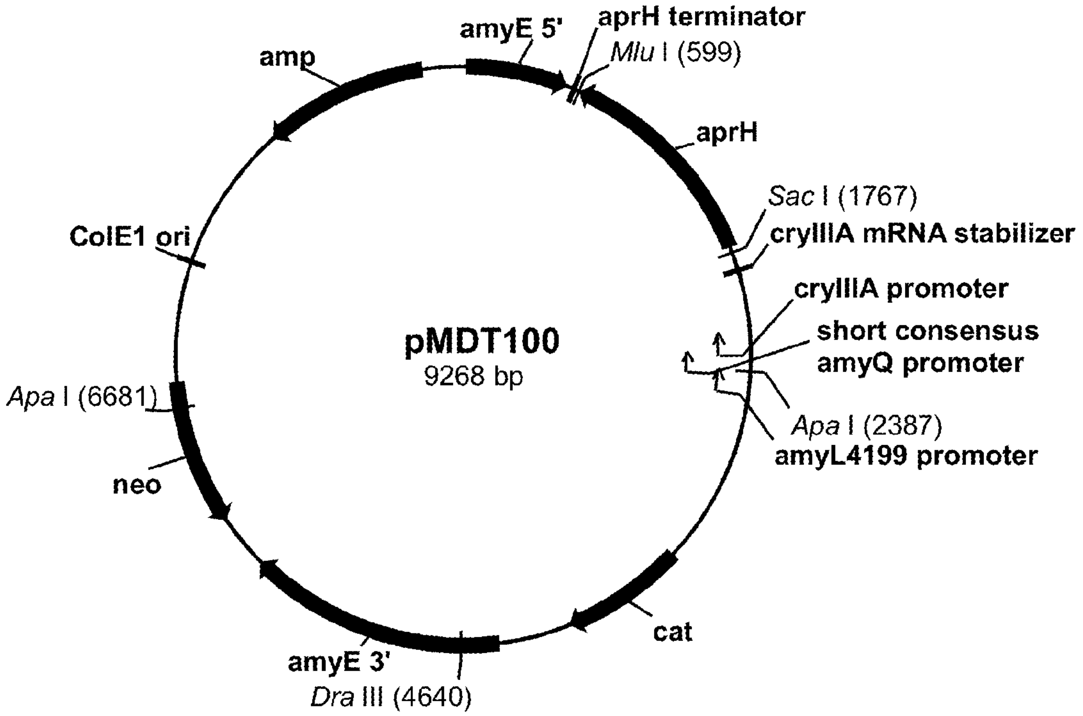
FIG. 14 shows a restriction map of pMDT100.

Plasmid pNBT13 (pDG268Δneo-$P_{amyL}$/$P_{cryIIIA}$/cryIIIAstab/SAV; U.S. Pat. No. 6,255,076) was digested with Dra III and Sac I, and a vector fragment of approximately 6395 bp was purified using a QIAQUICK® Gel Extraction Kit. Plasmid pNBT36 was digested with Dra III and Sac I, analyzed by 0.8% agarose electrophoresis in TBE buffer, and a fragment of approximately 2873 bp bearing the $P_{amyL4199}$/$P_{short\ consensus\ amyQ}$/$P_{cryIIIA}$ triple tandem promoter was purified using a QIAQUICK® Gel Extraction Kit. The pNBT13 vector fragment and $P_{amyL4199}$/$P_{short\ consensus\ amyQ}$/$P_{cryIIIA}$ fragment were ligated as described above, and *E. coli* SURE® cells were transformed with the ligation as described above, selecting for ampicillin resistance on 2×YT ampicillin plates at 37° C. Plasmid DNA was isolated from several transformants using a QIAPREP® 8 Miniprep Kit, digested with Apa I, and analyzed by 0.8% agarose electrophoresis in TBE buffer. One plasmid with expected restriction fragments of approximately 4974 bp and 4294 bp was designated pMDT100 (FIG. 14).

Example 6

Expression of the *Bacillus licheniformis* M.Bli1904II DNA Methyltransferase Gene in *Bacillus subtilis*

The *Bacillus licheniformis* M.Bli1904II DNA methyltransferase gene was inserted into the chromosome of *Bacillus subtilis* in order to express the methyltransferase in that host, thereby allowing methylation of DNA in *Bacillus subtilis.*

Plasmid pMDT100 was digested with Sac I and Mlu I, analyzed by 0.8% agarose electrophoresis in TBE buffer, and a vector fragment of approximately 8100 bp was purified using a QIAQUICK® Gel Extraction Kit. Plasmid pMDT138 was digested with Sac I and Mlu I, and a fragment of approximately 1033 bp bearing the M.Bli1904II gene was purified using a QIAQUICK® Gel Extraction Kit. The pMDT100 vector fragment and M.Bli1904II gene fragment were ligated as described above. This ligation placed the M.Bli1904II gene downstream of the $P_{amyL4199}/P_{short\ consensus\ amyQ}/P_{cryIIIA}$/cryIIIAstab promoter and upstream of the aprH transcription terminator. *Bacillus subtilis* 168Δ4 was transformed with the ligation according to the procedure of Anagnostopoulos and Spizizen, 1961, *J. Bacteriol.* 81: 741-746 and transformants were selected for chloramphenicol resistance on TBAB chloramphenicol plates at 37° C. Chloramphenicol-resistant transformants were screened for neomycin sensitivity on TBAB neomycin plates at 37° C. to determine whether the DNA had inserted into the amyE gene of the *Bacillus subtilis* chromosome by double crossover.

The presence of the M.Bli1904II DNA methyltransferase expression cassette at the amyE locus was confirmed by PCR using primers 994112 and 999592 shown below (which bind within the triple tandem promoter and M.Bli1904II DNA methyltransferase gene, respectively) and primers 999611 and 960456 shown below (which bind within the M.Bli1904II DNA methyltransferase gene and amyE gene, respectively). One such transformant, containing the cat gene and the M.Bli1904II DNA methyltransferase expression cassette at the amyE locus, was designated *Bacillus subtilis* MDT101.

```
Primer 994112:
                                        (SEQ ID NO: 58)
5'-GCGGCCGCTCGCTTTCCAATCTGA-3'

Primer 999592:
                                        (SEQ ID NO: 59)
5'-ATCGATCAGCTTGGATAAACCCTA-3'

Primer 999611:
                                        (SEQ ID NO: 60)
5'-GAGCTCTGCAAGGAGGTATAATTTTG-3'

Primer 960456:
                                        (SEQ ID NO: 61)
5'-CGTCGACGCCTTTGCGGTAGTGGTGCTT-3'
```

The PCRs were performed using Taq DNA Polymerase (New England Biolabs, Inc., Beverly, Mass., USA) according to the manufacturer's instructions. The amplification reactions (50 μl) were composed of 10 mM Tris-HCl (pH 8.3), 50 mM KCl, 3.0 mM $MgCl_2$, 200 μM of each dNTP, 0.5 μM of each primer, 0.25 units of Taq DNA Polymerase, and approximately 200 ng of genomic DNA. The PCRs were performed in a ROBOCYCLER® 40 Temperature Cycler programmed for 1 cycle at 95° C. for 2 minutes; 30 cycles each at 95° C. or 2 minutes, 55° C. or 2 minutes, and 72° C. for 2 minutes; and 1 cycle at 72° C. for 3 minutes.

Example 7

Inventory of *Bacillus licheniformis* Competence Genes

A keyword search of the *Bacillus subtilis* database (Subtilist; Moszer et al., 2002, *Nucleic Acids Res.* 30: 62-65) using the term "competence" in the query statement produced a list of 50 genes that play a role in competence development in that species (Table 1). Orthologues of *Bacillus subtilis* competence genes were identified in the genome sequence of *Bacillus licheniformis* ATCC 14580 (Rey et al., 2004, *Genome Biol.* 5: R77) using BLAST (McGinnis and Madden, 2004, *Nucleic Acids Res.* 32: W20-5) with a minimum expectancy score of $1\times10^{-10}$.

TABLE 1

Comparison of competence genes encoded by the genomes of *Bacillus subtilis* and *Bacillus licheniformis*.

| *Bacillus subtilis* gene | Swiss Prot | Function | Presence in Bacillus licheniformis |
|---|---|---|---|
| abrB | P08874 | pleiotropic transcriptional regulator of transition state genes | + |
| addA | P23478 | ATP-dependent deoxyribonuclease (subunit A) | + |
| addB | P23477 | ATP-dependent deoxyribonuclease (subunit B) | + |
| bdbC | | thiol-disulfide oxidoreductase | + |
| cinA | P46323 | competence-damage inducible protein | + |
| clpC | P37571 | class III stress response-related ATPase | + |
| clpP | P80244 | ATP-dependent Clp protease proteolytic subunit (class III heat-shock protein) | + |
| clpX | P50866 | ATP-dependent Clp protease ATP-binding subunit (class III heat-shock protein) | + |
| comA | P14204 | two-component response regulator of late competence genes/surfactin production | + |
| comC | P15378 | late competence protein required for processing and translocation of ComGC, ComGD, ComGE, ComGG | + |

TABLE 1-continued

Comparison of competence genes encoded by the genomes of *Bacillus subtilis* and *Bacillus licheniformis.*

| *Bacillus subtilis* gene | Swiss Prot | Function | Presence in Bacillus licheniformis |
|---|---|---|---|
| comEA | P39694 | exogenous DNA-binding protein | + |
| comEB | P32393 | late competence operon required for DNA binding and uptake | + |
| comEC | P39695 | late competence operon required for DNA binding and uptake | + |
| comER | P39696 | non-essential gene for competence | + |
| comFA | P39145 | late competence protein required for DNA uptake | + |
| comFB | P39146 | late competence gene | + |
| comFC | P39147 | late competence gene | + |
| comGA | P25953 | late competence gene | + |
| comGB | P25954 | DNA transport machinery | + |
| comGC | P25955 | exogenous DNA-binding | + |
| comGD | P25956 | DNA transport machinery | + |
| comGE | P25957 | DNA transport machinery | + |
| comGF | P25958 | DNA transport machinery | + |
| comGG | P25959 | DNA transport machinery | + |
| comK | P40396 | competence transcription factor (CTF) | + |
| comP | Q99027 | two-component sensor histidine kinase involved in early competence | IS3Bli1 insertion |
| comQ | P33690 | transcriptional regulator of late competence operon (comG) and surfactin expression (srfA) | + |
| comS | P80355 | assembly link between regulatory components of the competence signal transduction pathway | − |
| comX | P45453 | competence pheromone precursor | + |
| comZ | | late competence gene | + |
| degS | P13799 | two-component sensor histidine kinase involved in degradative enzyme and competence regulation | + |
| degU | P13800 | two-component response regulator involved in degradative enzyme and competence regulation | + |
| IspA | Q45479 | signal peptidase II | + |
| mecA | P37958 | negative regulator of competence | + |
| med | | positive regulator of comK | + |
| nin | P12669 | inhibitor of the DNA degrading activity of NucA | + |
| nucA | P12667 | membrane-associated nuclease | + |
| oppA | P24141 | oligopeptide ABC transporter (binding protein) (initiation of sporulation, competence development) | + |
| oppB | P24138 | oligopeptide ABC transporter (permease) (initiation of sporulation, competence development) | + |
| oppC | P24139 | oligopeptide ABC transporter (permease) (initiation of sporulation, competence development) | + |
| oppD | P24136 | oligopeptide ABC transporter (ATP-binding protein) (initiation of sporulation, competence development) | + |
| oppF | P24137 | oligopeptide ABC transporter (ATP-binding protein) (initiation of sporulation, competence development) | + |
| phrC | | phosphatase (RapC) regulator/competence and sporulation stimulating factor (CSF) | + |
| pnpA | P50849 | polynucleotide phosphorylase (PNPase) | + |
| rapE | P45943 | response regulator aspartate phosphatase | + |
| recA | P16971 | multifunctional protein involved in homologous recombination and DNA repair (LexA-autocleavage) | + |
| sinR | P06533 | transcriptional regulator of post-exponential-phase genes | + |
| slr | | transcriptional activator of competence development and sporulation genes | + |
| smf | P39813 | DNA processing Smf protein homolog | + |
| spo0F | P06628 | two-component response regulator involved in the initiation of sporulation | + |

As shown in Table 1, the *Bacillus licheniformis* ATCC 14580 genome appears to harbor all of the genes necessary for competence development except the comP gene that has been interrupted by the insertion sequence IS3Bli1 (Lapidus et al., 2002*, FEMS Microbiol. Lett.* 209: 23-30) and comS that is either not present or is substantially different than the corresponding gene in *Bacillus subtilis*. The early portion of the competence signal transduction cascade cannot function properly in *Bacillus licheniformis* without an active comP gene product. However, the early portion of the competence cascade can be circumvented by increased expression of the central transcription factor ComK, which induces transcription of the late competence genes that encode DNA binding and uptake machinery (Susanna et al., 2004*, J. Bacteriol.* 186: 1120-8). However, if the level of MecA protein is sufficiently high to bind and inactivate all of the ComK protein, then it is possible that increased comK gene expression alone might not be sufficient to induce competence. Instead increased expression of the comS gene would be required to overcome the activity of MecA, and thereby liberate ComK to activate transcription of the late competence genes.

In *Bacillus subtilis*, the comS gene is embedded within the coding region of the fourth amino acid-activation domain of srfA gene. Consequently, the corresponding IchA region (srfA orthologue) was scanned in *Bacillus licheniformis* to locate possible ComS-like sequences. The comparative alignment in FIG. 15 showed that the closest predicted *Bacillus licheniformis* orthologue differs appreciably from the known ComS gene product in *Bacillus subtilis*, and a number of residues that are known to be important for biological activity have diverged in *Bacillus licheniformis*. It was unknown whether the putative ComS orthologue in *Bacillus licheniformis* is functional.

Two experimental approaches were pursued. The first approach involved increased expression of comK to bypass the early portion of the competence cascade, and a second approach involved increasing expression of comS to circumvent degradation of ComK by the MecA/ClpCP complex (see FIG. 1).

Example 8

Construction of pMRT098

The xylA promoter and xylR gene from plasmid pAX01 (Härtl et al., 2001, *J. Bact.* 183: 2696-2699) were amplified by PCR using primers 992129 and 992130 shown below.

```
Primer 992129
                                    (SEQ ID NO: 62)
5'-GAGCTCGGATCCCATTTCC-3'

Primer 992130
                                    (SEQ ID NO: 63)
5'-ATCTCTGAGCTCGCGATGATTAATTAATTCAGAACGCTCGGTTG
CCGCCGGGCGTTTTTTATGCAGCAATGGCAAGAACGTCCCGGTTAGC
TCC-3'
```

The PCR amplification was conducted in a 50 μl reaction composed of 10 ng of pAX01 DNA, 0.4 μM of each primer, 200 μM each of dATP, dCTP, dGTP, and dTTP, 1×PCR Buffer II with 2.5 mM $MgCl_2$, and 2.5 units of AMPLITAQ GOLD® enzyme (Applied Biosystems, Inc., Foster City, Calif., USA). The reactions were performed in a ROBOCYCLER® 40 Temperature Cycler programmed for 1 cycle at 95° C. for 10 minutes; 25 cycles each at 95° C. for 1 minute, 53° C. for 1 minute, and 72° C. for 1.5 minutes; and 1 cycle at 72° C. for 7 minutes. The PCR product was visualized by 0.8% agarose gel electrophoresis in 0.5×TBE buffer. The expected fragment was about 1500 bp long.

The PCR fragment was cloned into pCR2.1 using a TA-TOPO® Cloning Kit (Invitrogen, Carlsbad, Calif., USA) and transformed into *E. coli* ONE SHOT® competent cells according to the manufacturer's instructions. Transformants were selected on 2×YT agar plates supplemented with 100 μg of amplicillin per ml incubated at 37° C. for 16 hours. Plasmid DNA from several of these transformants was purified using a BIOROBOT® 9600 (QIAGEN Inc., Valencia, Calif., USA) according to manufacturer's instructions and the DNA sequence of the inserts confirmed by DNA sequencing using M13 (−20) forward and M13 reverse primers (Invitrogen, Inc, Carlsbad, Calif., USA). The plasmid harboring the correct PCR fragment was designated pMRT091.

Plasmids pMRT091 and pUC18 (Yanisch-Perron et al., 1985, *Gene* 33: 103-119) were digested with Bam HI and Sac I. The digestions were resolved by 0.8% agarose gel electrophoresis in 0.5×TBE buffer and the larger vector fragment from pUC18 and the smaller fragment from pMRT091 were gel-purified using a QIAQUICK® DNA Extraction Kit according to manufacturer's instructions. The two purified fragments were ligated together using a Rapid DNA Ligation Kit (Roche Applied Science, Indianapolis, Ind., USA) according to the manufacturer's instructions and the ligation mix was transformed into *E. coli* XL1 SE competent cells (Stratagene, Inc., La Jolla, Calif., USA). Transformants were selected on 2×YT agar plates supplemented with 100 μg/ml ampicillin.

Plasmid DNA was purified from several transformants using a BIOROBOT® 9600 according to manufacturer's instructions and analyzed by Bam HI and Sac I digestion followed by 0.8% agarose gel electrophoresis in 0.5×TBE buffer. The correct plasmid was identified by the presence of an approximately 700 bp Ave I/Bam HI pMRT091 fragment and was designated pMRT096.

In addition, the Hind III and Eco RI sites present in the xylR gene of pMRT096 were deleted by SOE PCR (Horton et al., 1989, *Gene* 77: 61-68) with primers 992131 and 992132, and then with primers 992129 and 992131.

```
Primer 992131
                                    (SEQ ID NO: 64)
5'-CTTCTCGAGAATAATATTTCCTTCTAAGTCGGTTAGGATTCCG-3'

Primer 992132
                                    (SEQ ID NO: 65)
5'-CAAGCATCAAAAAACACCAACTTAGTTCGGTGGATAAACAAAGGA
GTGGTTATTATTCAAATTGCAGATCAGGCTTTAG-3'
```

The PCR amplification was conducted in a 50 μl reaction composed of 10 ng of pAX01 DNA, 0.4 μM of each primer, 200 μM each of dATP, dCTP, dGTP, and dTTP, 1×PCR Buffer II with 2.5 mM $MgCl_2$, and 2.5 units of AMPLITAQ GOLD® enzyme. The reactions were performed in a ROBOCYCLER® 40 Temperature Cycler programmed for 1 cycle at 95° C. for 10 minutes; 25 cycles each at 95° C. for 1 minute, 55° C. for 1 minute, and 72° C. for 1 minutes; and 1 cycle at 72° C. for 7 minutes. The PCR product was visualized by 0.8% agarose gel electrophoresis in 0.5×TBE buffer. The expected fragment was approximately 700 bp.

The PCR fragment was cloned into pCR2.1 using a TA-TOPO® Cloning Kit and transformed into *E. coli* ONE SHOT® competent cells according to the manufacturer's instructions. Transformants were selected on 2×YT agar plates supplemented with 100 μg of ampicillin per ml incubated at 37° C. for 16 hours. Plasmid DNA from several of these transformants was purified using a BIOROBOT® 9600 according to manufacturer's instructions and the DNA sequence of the inserts confirmed by DNA sequencing using M13 (−20) forward and M13 reverse primers (Invitrogen, Inc, Carlsbad, Calif., USA). The plasmid harboring the correct PCR fragment was designated pMRT092.

Plasmids pMRT096 and pMRT092 were digested with Bam HI and Ave I. The digestions were resolved by 0.8% agarose gel electrophoresis in 0.5×TBE buffer and the larger vector fragment from pMRT096 and the smaller fragment from pMRT092 were gel-purified using a QIAQUICK® DNA Extraction Kit according to manufacturer's instructions. The two purified fragments were ligated together using a Rapid DNA Ligation Kit according to manufacturer's instructions and the ligation mix was transformed into *E. coli* XL1 SE competent cells (Stratagene, Inc., La Jolla, Calif., USA). Transformants were selected on 2×YT agar plates supplemented with 100 μg of amplicillin per ml.

Figure 16:
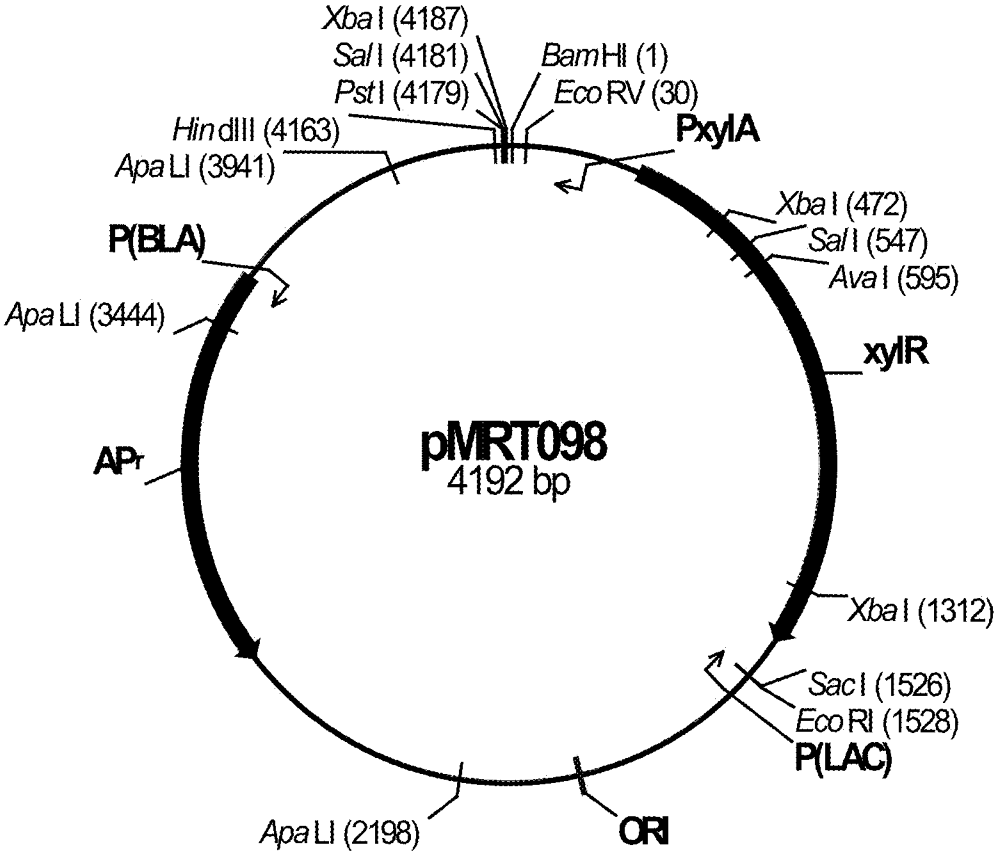
FIG. 16 shows a restriction map of pMRT098.

Plasmid DNA was purified from several transformants using a BIOROBOT® 9600 according to manufacturer's instructions and analyzed by digestion with Eco RI and Hind III followed by 0.8% agarose gel electrophoresis in 0.5×TBE buffer. The correct plasmid was identified by the presence a single 4200 bp fragment when digested with Eco RI or Hind III. This construct was designated pMRT098 (FIG. 16).

Example 9

Construction of pΔComS

Plasmid pΔComS was constructed by digesting pBD2528 (also termed pComS; Hahn et al., 1996, *Mol. Microbiol.* 21: 763-75) with Bam HI plus Hind III, treating with DNA polymerase I (Klenow fragment) to generate blunt ends, and by re-circularizing the vector with T4 DNA ligase to create a control plasmid that was identical to pBD2528 but lacking the comS gene. To ensure proper methylation for further transformation into *Bacillus licheniformis* SJ1904, plasmids pΔcomS and pComS were transformed into *Bacillus subtilis* MDT101 described herein according to the procedure of Anagnostopoulos and Spizizen, 1961, supra. Transformants were selected on TBAB media supplemented with 20 μg of kanamycin per ml.

Example 10

Amplification and Cloning of *Bacillus licheniformis* SJ1904 comK Gene into the *E. Coli* Vector pMRT098

The following PCR primers were designed to amplify DNA encoding ComK from *Bacillus licheniformis* SJ1904. Restriction enzyme sites Bam HI and Pst I (underlined) were added to facilitate cloning of the comK gene segment into pMRT098.

```
Primer 999722:
                                        (SEQ ID NO: 66)
5'-GTGGATCCgattaggaggatcaaaatg-3'
      BamHI

Primer 999723:
                                        (SEQ ID NO: 67)
5'-CAGTACTGCAGtcaatagcgctttttcagctccctgaggatAa
         PstI
attcgtatatc-3'
```

A comK gene fragment was amplified by PCR using an Expand High Fidelity PCR System (Roche Applied Science, Indianapolis, Ind., USA). Genomic DNA was isolated from *Bacillus licheniformis* SJ1904 according to the procedure of Pitcher et al., 1989, supra. The PCR amplification reaction mixture contained 1 μl of 145 ng/μl of *Bacillus licheniformis* SJ1904 genomic DNA, 1 μl of primer 999722 (50 pmol/μl), 1 μl of primer 999723 (50 pmol/μl), 5 μl of 10×PCR buffer with 15 mM $MgCl_2$, 1 μl of dNTP mix (10 mM each), 37.25 μl of water, and 0.75 μl (3.5 units/μl) of DNA polymerase mix. An EPPENDORF® MASTERCYCLER® 5333 (Hamburg, Germany) was used to amplify the fragment programmed for 1 cycle at 94° C. for 2 minutes; 10 cycles each at 94° C. for 15 seconds, 60° C. for 30 seconds, and 72° C. for 1 minute; 15 cycles each at 94° C. for 15 seconds, 60° C. for 30 seconds, 72° C. for 1 minute plus a 5 second elongation at each successive cycle; and 1 cycle at 72° C. for 7 minutes; and a 4° C. hold.

A 579 bp PCR product was purified using a NANOSEP® 30K OMEGA™ centrifugal device according to the manufacturer's instructions (Pall Life Science, Inc., Ann Arbor, Mich., USA). Then the 579 bp PCR product and vector pMRT098 were digested with Bam HI and Pst I. The fragments were ligated together using a Rapid DNA Ligation Kit following the manufacturer's instructions. Two μl of the reaction was used to transform *E. coli* SURE® Cells according to manufacturer's instructions.

Figure 17:
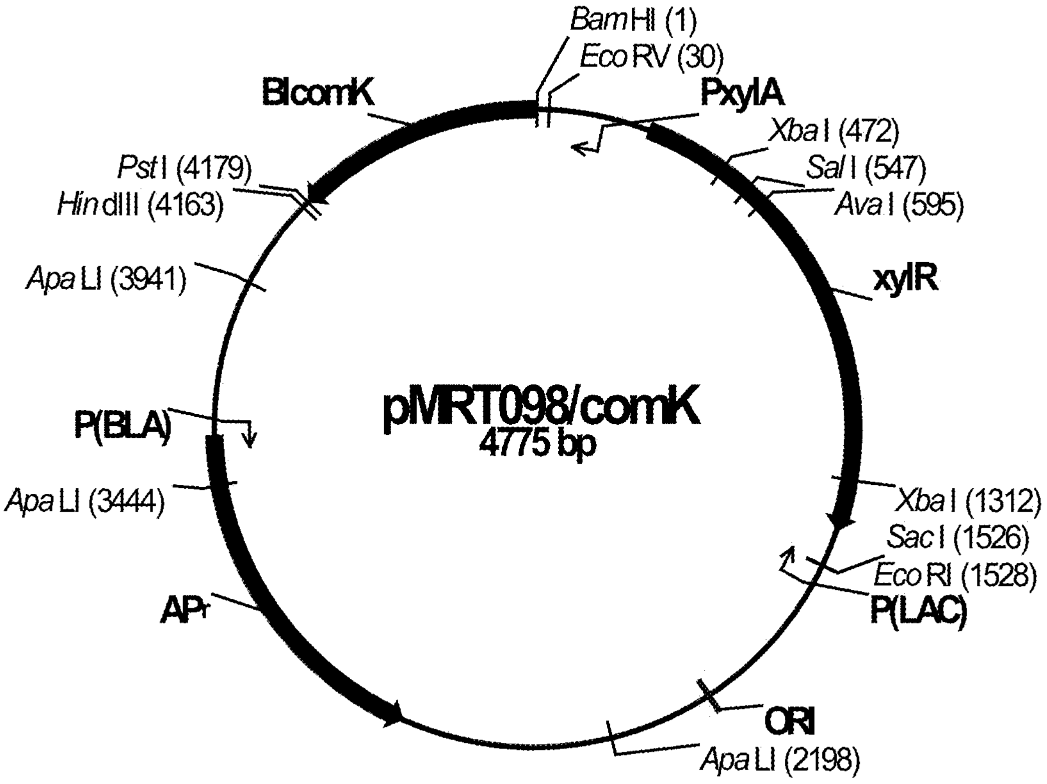
FIG. 17 shows a restriction map of pMRT098/comK.

Plasmid DNA was prepared from the *E. coli* transformants and sequenced using 1 μl of plasmid template, 1.6 ng of primer 999722 or primer 999723 (described above), and water to 6 μl. DNA sequencing was performed with an Applied Biosystems Model 377 Sequencer XL using dye-terminator chemistry. The resulting plasmid identified as having the correct sequence was designated pMRT098/comK (FIG. 17).

Example 11

Construction of *E. Coli* Plasmid Containing the *Bacillus licheniformis* SJ1904 comK Gene Under Control of a Xylose Inducible Promoter Flanked by amyL Integration Arms The following PCR primers were designed to amplify DNA encoding the 3'-amyL integration arms from pMRT074 (U.S. Published Application 2003/0175902):

```
Primer 999726:
                                        (SEQ ID NO: 68)
5'-ctgaaacaacaaaaacggctttac-3'

Primer 999727:
                                        (SEQ ID NO: 69)
5'-ACTGAAGCTTggttgcggtcagcgggatcg-3'
         Hind III
```

Since the 3'-amyL integration arm has a native Pst I site, a Hind III cleavage site was added for cloning the 3'-amyL integration arm into pMRT098/comK as a Pst I-Hind III fragment. The fragment of interest was amplified by PCR using an Expand High Fidelity PCR System. The PCR amplification reaction mixture contained approximately 10 ng of pMRT074 plasmid DNA, 1 μl of primer 999726 (50 pmol/μl), 1 μl of primer 999727 (50 pmol/μl), 5 μl of 10×PCR buffer with 15 mM $MgCl_2$, 1 μl of dNTP mix (10 mM each), 37.25 μl of water, and 0.75 μl (3.5 U/μl) of DNA polymerase mix. An EPPENDORF® MASTERCYCLER® 5333 was used to amplify the fragment programmed for 1 cycle at 94° C. for 2 minutes; 10 cycles each at 94° C. for 15 seconds, 60° C. for 30 seconds, and 72° C. for 1 minute; 15 cycles each at 94° C. for 15 seconds, 60° C. for 30 seconds, 72° C. for 1 minute plus 5 second elongation at each successive cycle; 1 cycle at 72° C. for 7 minutes; and a 4° C. hold.

Figure 18:
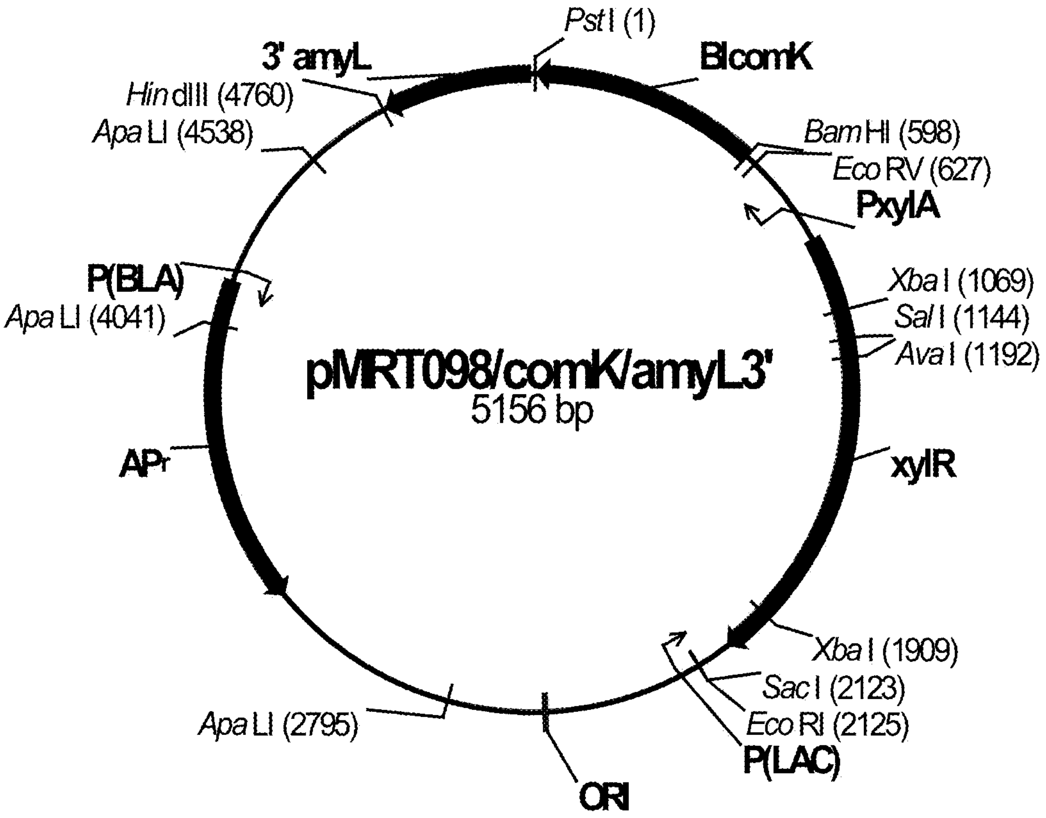
FIG. 18 shows a restriction map of pMRT098/comK/amyL3'.

A 450 bp PCR product was purified using a NANOSEP® 30K OMEGA™ centrifugal device according to the manufacturer's instructions. The purified PCR product along with vector pMRT098/comK were digested with Hind III and Pst I, analyzed by 1% agarose gel electrophoresis in TBE buffer, and both fragments were purified using a QIAQUICK® Gel Extraction Kit. The fragments were ligated using a Rapid DNA Ligation Kit following the manufacturer's instructions. Two μl of the reaction was used to transform *E. coli* SURE® Cells according to manufacturer's instructions. Plasmid DNA was prepared from the *E. coli* transformants and digested with Hind III and Pst I, followed by 1% agarose gel electrophoresis in TBE buffer. The resulting plasmid identified as having the correct restriction pattern was designated pMRT098/comK/amyL3' (FIG. 18).

The following PCR primers were designed to amplify DNA encoding the 5'-amyL integration arms from pMRT074:

```
Primer 999724:
                                   (SEQ ID NO: 70)
      Eco RI
5'-AGTCgaattcgactggaagcagagc-3'

Primer 999756:
                                   (SEQ ID NO: 71)
       Sac I
5'-TCAGGAGCTCagtaccattttccctata-3'
```

Restriction sites for Eco RI and Sac I were added to facilitate cloning of the 5'-amyL integration arm into the pMRT098/comK/amyL3' (described above). The fragment of interest was amplified by PCR using conditions described above.

Figure 19:
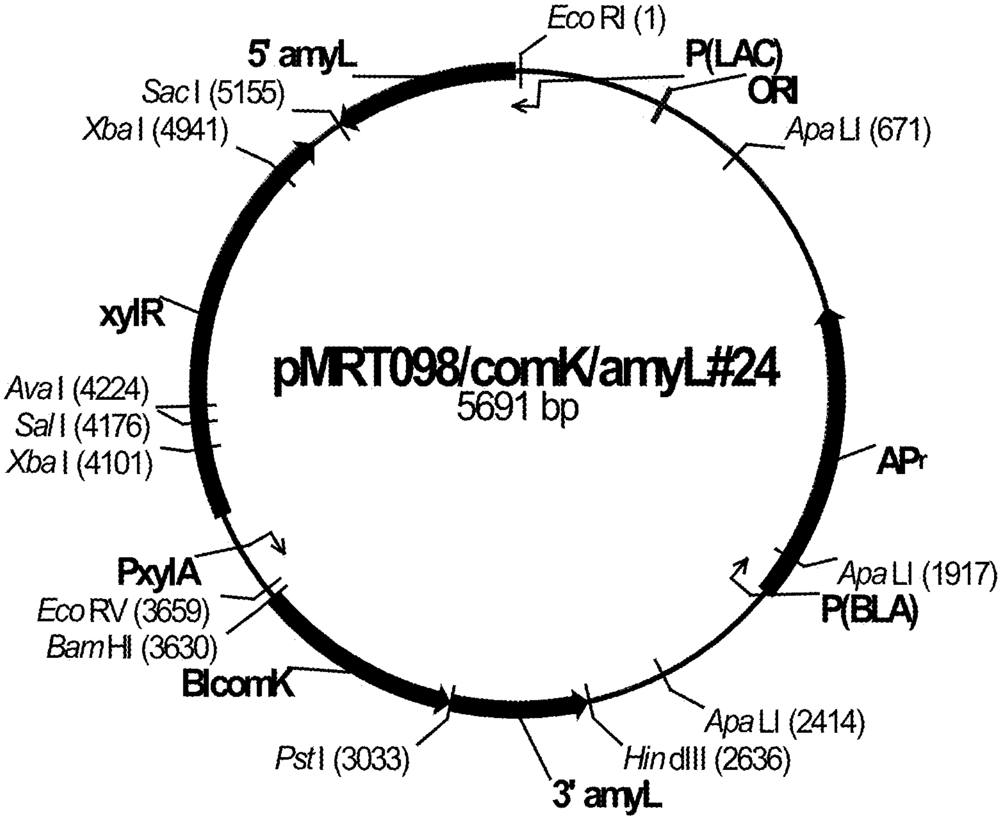
FIG. 19 shows a restriction map of pMRT098/comK/amyL#24.

A 523 bp PCR product was purified using a NANOSEP® 30K OMEGA™ centrifugal device according to the manufacturer's instructions. Then the 523 bp PCR product and vector pMRT098/comK/amyL3' were digested with Eco RI and Sac I, analyzed by 1% agarose gel electrophoresis in TBE buffer, and both fragments were purified using a QIAQUICK® Gel Extraction Kit. The fragments were ligated using a Rapid DNA Ligation Kit following the manufacturer's instructions. A 2 μl aliquot of the ligation was used to transform *E. coli* SURE® Cells according to manufacturer's instructions. Plasmid DNA was prepared from the *E. coli* transformants and digested with Eco RI and Sac I, followed by 1% agarose gel electrophoresis in 1×TBE buffer. The resulting plasmid identified as having the correct restriction pattern was designated pMRT098/comK/amyL#24 (FIG. 19).

Example 12

Construction of *Bacillus licheniformis* SJ1904 comK Expression Vector pMMar2

Plasmid pMRT098/comK/amyI#24 was digested with Eco RI, Sca I, and Hind III, and a 3178 bp fragment was purified by 0.7% agarose gel electrophoresis in TAE buffer (4.84 g of Tris Base, 1.14 ml of glacial acetic acid, and 2 ml of 0.5 M EDTA pH 8.0 per liter) in conjunction with a QIAQUICK® Gel Extraction Kit. A vector fragment from pMRT077 (WO 2003/054163) was generated by digestion with Eco RI and Hind III, and a 4340 bp fragment was purified by 0.7% agarose gel electrophoresis in TAE buffer in conjunction with a QIAQUICK® Gel Extraction Kit. The 3178 bp and 4340 bp fragments were subsequently ligated in approximately equimolar concentrations using T4 DNA ligase at 16° C. for 16 hours. The entire ligation mixture was used to transform *Bacillus subtilis* 168Δ4 competent cells according to the procedure of Anagnostopoulos and Spizizen, 1961, supra. Transformants were selected on TBAB erythromycin/lincomycin plates.

*Bacillus subtilis* genomic DNA was prepared from a few transformants according to the procedure described by Pitcher et al., 1989, supra. PCR amplification was used to confirm plasmid construction using an Expand High Fidelity PCR System. The 50 μl PCR amplification reaction mixture contained 100 ng of genomic DNA, 1 μl of primer 999722 (50 pmol/μl), 1 μl of primer 999727 (50 pmol/μl), 5 μl of 10×PCR buffer with 15 mM $MgCl_2$, 1 μl of dNTP mix (10 mM each), 37.25 μl of water, and 0.75 μl (3.5 U/μl) of DNA polymerase mix. An Eppendorf Mastercycler 5333 was used to amplify the fragment programmed for 1 cycle at 94° C. for 2 minutes; 10 cycles each at 94° C. for 15 seconds, 60° C. for 30 seconds, and 72° C. for 1 minute; 15 cycles each at 94° C. for 15 seconds, 60° C. for 30 seconds, and 72° C. for 1 minute plus 5 second elongation at each successive cycle; 1 cycle at 72° C. for 7 minutes; and a 4° C. hold.

Figure 20:
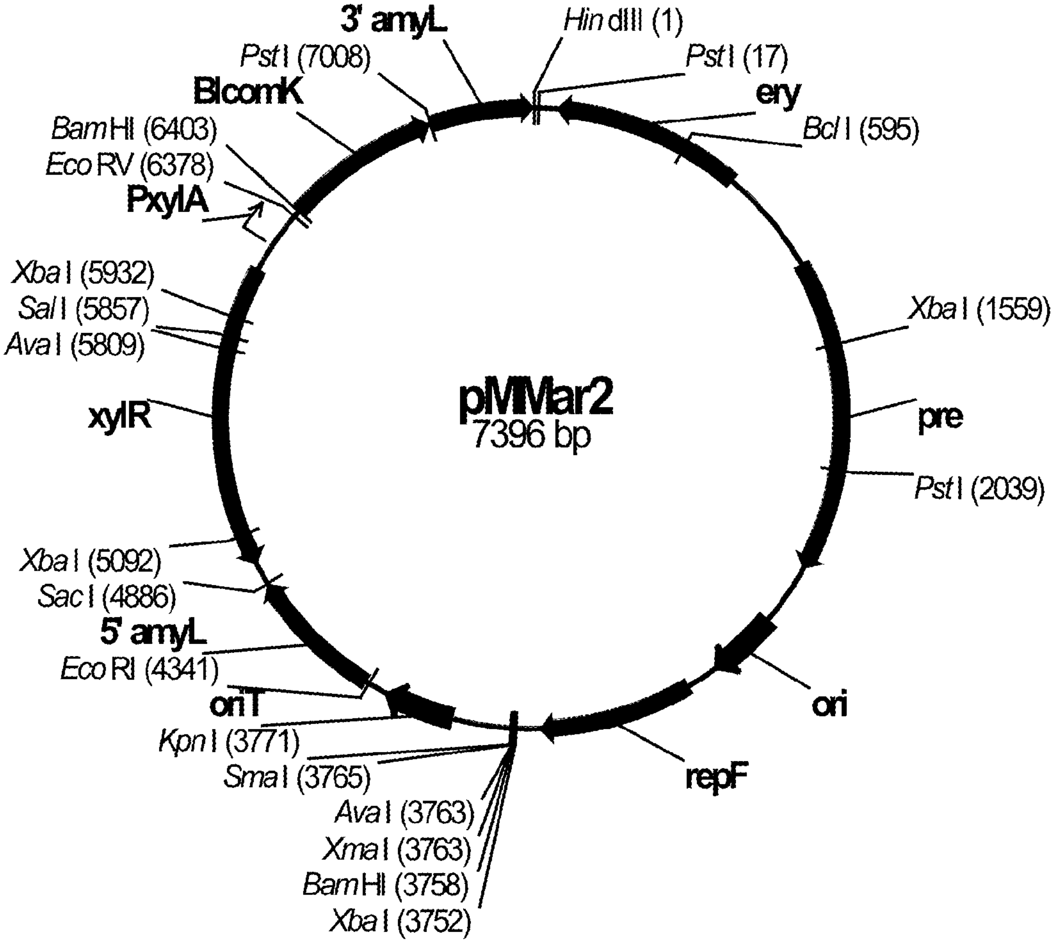
FIG. 20 shows a restriction map of pMMar2.

A transformant containing the expected 1029 bp amplified fragment, as determined by 0.8% agarose gel electrophoresis in TBE buffer, was designated pMMar2 (FIG. 20). Furthermore, plasmid DNA prepared from *Bacillus subtilis* 168Δ4/pMMar2, followed by restriction enzyme digestion, resulted in the expected size fragments, when analyzed by gel electrophoresis. To ensure proper methylation for further transformation into *Bacillus licheniformis* SJ1904, plasmid pMMar2 was transformed into *Bacillus subtilis* MDT101 described herein according to the procedure of Anagnostopoulos and Spizizen, 1961, supra. Transformants were selected on TBAB erythromycin/lincomycin plates.

Example 13

Integration of pMMar2 into the amyL Locus of *Bacillus licheniformis SJ*1904

An expression cassette comprising the *Bacillus licheniformis* comK gene under control of a xylose-inducible xylA promoter (Kim et al., 1996, *Gene* 181: 71-6) was incorporated into the genomic DNA of *Bacillus licheniformis* SJ1904 by chromosomal integration and excision of the temperature-sensitive plasmid pMMar2. *Bacillus licheniformis* transformants containing plasmid pMMar2 were plated on TBAB erythromycin/lincomycin plates at 45° C. to force integration of the vector. Desired integrants were chosen based on their ability to grow on TBAB erythromycin/lincomycin plates at 45° C. Integrants were then grown without selection in VY medium at 34° C. to induce excision of the integrated plasmid. Cells were plated on LB plates or minimal medium plates, and colonies were screened for erythromycin-sensitivity. Erythromycin-sensitive clones were screened for gene conversion by PCR to detect the integrated xylA::comK cassette. The resulting strain, containing the xylA promoter driving *Bacillus licheniformis* comK expression integrated at the amyL locus, was designated *Bacillus licheniformis* SJ 1904 xylA::comK.

Example 14

*Bacillus Licheniformis* SJ1904 and SJ1904 xylA::comK Transformation with pMMar2, pComS, or pΔComS Plasmids pMMar2, pComS, and pΔComS were isolated from *Bacillus subtilis* MDT101 using a Plasmid Midi Kit. *Bacillus licheniformis* strain SJ1904 was transformed with pMMar2, pComS, and pΔComS plasmid DNA, and *Bacillus licheniformis* xylA::comK was transformed with pComS plasmid DNA by electroporation as described herein. The resulting *Bacillus licheniformis* transformants were designated SJ1904 (pMMar2), SJ1904 (pComS), SJ1904 (pΔComS), and SJ1904 xylA::comK (pComS), respectively.

Example 15

Expression of the *Bacillus licheniformis* comK Gene in *Bacillus Subtilis* A164Δ5 and *Bacillus licheniformis* SJ1904

Plasmid pMMar2 carrying the *Bacillus licheniformis* comK gene under transcriptional control of the xylose-inducible xylA promoter was first introduced into *Bacillus subtilis* 164Δ5 by transformation as described above. The pMMar2 vector also harbors a gene conferring resistance to erythromycin. An erythromycin resistant transformant, designated *Bacillus subtilis* 164Δ5/pMMar2, was subsequently tested for competence development in medium that contained either glucose (represses the xylA promoter) or glucose plus xylose (partial repression of the xylA promoter) or xylose (de-repression of the xylA promoter). *Bacillus subtilis* 164Δ5/pMMar2 and *Bacillus subtilis* 164Δ5 competent cells were prepared by growth in Spizizen I medium containing either 1% xylose and/or 0.5% glucose using methods described above. Cells were stored frozen at −80° C. prior to use. For transformation, the cell mixtures were quickly thawed in a 37° C. water bath. One microgram of pGME086 plasmid DNA was added to each transformation mixture along with LB medium containing 0.5% glucose or 1% xylose and 0.2 μg of chloramphenicol per ml. Plasmid pGME086, a pE194 (Gryczan et al., 1982, *J. Bacteriol.* 152: 722-735) derivative, carries the chloramphenicol resistance marker from pC194 (Horinouchi et al., 1982, *J. Bacteriol.* 150: 815-825). The transformation mixtures were grown for 1 hour in a shaking incubator at 34° C. After 1 hour, the reaction mixtures were plated on LB chloramphenicol/erythromycin plates. Plates were incubated at 34° C. for 24 hours. Colonies were counted on the following day to determine transformation efficiencies.

Table 2 shows that the number of transformants following growth of the recipient strain in medium with xylose as the sole carbon source was approximately 200 times the number obtained following growth in glucose or glucose plus xylose. These results demonstrated that the heterologous *Bacillus licheniformis* comK gene was not only transcribed from the xylA promoter, but that the *Bacillus licheniformis* ComK protein effectively induced a competent state in *Bacillus subtilis*.

TABLE 2

Competence induction in *Bacillus subtilis* using the comK gene from *Bacillus licheniformis*

| Growth medium | Total number of colonies resistant to both chloramphenicol and erythromycin |
|---|---|
| Control mediums† | 81 (102) |
| Spizizen I medium with glucose | 69 (156) |
| Spizizen I medium with glucose and xylose | 180 (149) |
| Spizizen I medium with xylose | 36,600 (34,400)‡ |

†Control medium was standard *Bacillus subtilis* competence medium (Anagnostopolous and Spizizen, 1961, supra)
‡These numbers determined from a 1:50 dilution of the transformation reaction. Numbers in parentheses are from replicate experiments.

Example 16

DNA Microarray Analysis

DNA microarrays were used to compare global transcription profiles in *Bacillus licheniformis* strain SJ1904 xylA::comK grown on glucose medium (comK repressed) and on xylose medium (comK induced).

DNA microarrays were prepared by spotting CDS-specific oligonucleotides (50 mers) selected from the protein-coding genes in the *Bacillus licheniformis* ATCC 14580 genome as deposited in Genbank (accession number CP000002). The oligonucleotides were purchased from MWG-Biotech, Inc., Highpoint, N.C., USA. Methods for microarray spotting, hybridization, and analysis were performed as described by Berka et al., 2003, *Proc. Natl. Acad. Sci. USA* 100: 5682-5687.

*Bacillus licheniformis* SJ1904 xylA::comK cells were cultured in Spizizen I medium containing either 0.5% glucose (repressing medium) or 1% xylose (inducing medium). Cells were harvested at 1, 3, and 5 hours post inoculum, and total cellular RNA was isolated using the methods described in Berka et al., 2003, supra. Fluorescent probes were prepared by reverse transcription of 25 μg of total RNA to incorporate aminoallyl-dUTP into first strand cDNA according to the procedure of Berka et al., 2003, supra. The amino-cDNA products were subsequently labeled by direct coupling to either Cy3 or Cy5 monofunctional reactive dyes (Amersham Pharmacia Biotech, Arlington Heights, Ill., USA) according to the procedure of Berka et al., 2003, supra. Probes derived from cells grown in glucose medium were labeled with Cy3, and probes derived from cells grown in xylose medium were labeled with Cy5. Hybridization and washing conditions were the same as those described in Berka et al., 2003, supra.

Microarray slides were imaged using an GENEPIX® 4000B scanner (Axon Instruments, Union City, Calif., USA). The fluorescence intensity values for microarray spots were quantified (including background subtraction) with GENEPIX® software (Axon Instruments), and the resulting figures were normalized using the Lowess function provided in S+ARRAYANALYZER™ software (Insightful Corporation, Seattle, Wash., USA). Genes that were induced by expression of the xylA::comK expression unit were assigned on the basis of Cy5/Cy3 ratios ≥2.0.

DNA microarrays were used to compare global transcription profiles in the *Bacillus licheniformis* strain SJ1904 xylA::comK grown on glucose medium (comK repressed) and on xylose medium (comK induced). The results of this analysis showed that comK transcript levels were increased substantially in cells grown on xylose medium (10 to 30-fold) compared to glucose medium. However, there was no concomitant increase in transcription of the late competence genes (comE, comF, and comG operons) in this experiment. Previous studies in *Bacillus subtilis* (Brzuszkiewicz et al., 2006, *Proc. Natl. Acad. Sci. USA* 103: 12879-84) showed that increased transcription of comK caused elevated transcription of the late competence genes. However, this correlation was not observed in *Bacillus licheniformis.*

Example 17

Construction of pMDT131

Figure 21:
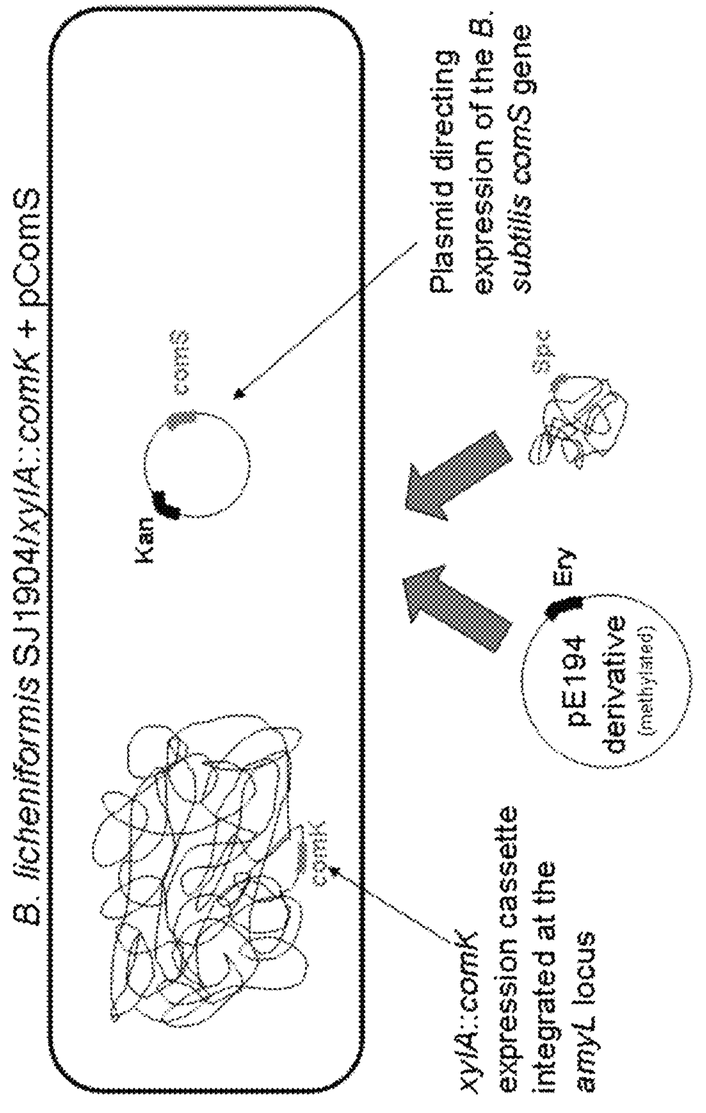
FIG. 21 shows a schematic diagram of the co-expression of *Bacillus subtilis* comS and *Bacillus licheniformis* comK.

Plasmid pMDT131 was constructed to create a temperature-sensitive plasmid conferring chloramphenicol resistance. Plasmid pMRT074 (U.S. Published Application 2003/0175902) was digested with Eco RI and then treated with T4 DNA polymerase plus dNTPs to generate blunt ends, as described in Example 5. The plasmid was then digested with Not I, analyzed by 0.8% agarose gel electrophoresis in TBE buffer, and a vector fragment of approximately 4355 bp was purified using a QIAQUICK® Gel Extraction Kit. Plasmid pNBT1 was digested with Eco 47III and Not I, analyzed by 0.8% agarose gel electrophoresis in TBE buffer, and a fragment of approximately 1222 bp bearing the cat gene and a multiple cloning site was purified using a QIAQUICK® Gel Extraction Kit. The pMRT074 vector fragment was ligated with the pNBT1 cat fragment using T4 DNA ligase as described above, and *Bacillus subtilis* 168Δ4 was transformed with the ligation according to the procedure of Anagnostopoulos and Spizizen, 1961, supra, selecting for chloramphenicol resistance on TBAB chloramphenicol plates at 34° C. Plasmid DNA was isolated from one transformant using a Plasmid Midi Kit and confirmed by digestion with Bam HI followed by 0.8% agarose gel electrophoresis in TBE buffer, which yielded expected fragments of approximately 3779 bp and 1802 bp. The resulting plasmid was designated pMDT131 (FIG. 21).

Example 18

Co-Expression of the *Bacillus subtilis* comS and *Bacillus Licheniformis* comK Genes in *Bacillus licheniformis*

There are two possible approaches to test the hypothesis that unexpectedly high activity of the MecA/ClpCP complex prevents ComK from inducing the late competence genes in *Bacillus licheniformis*. The first would involve disruption of the mecA gene. However, previous studies have indicated that mecA may act generally as an adapter molecule, targeting proteins for regulated degradation (Persuh et al., 1999, *Mol. Microbiol.* 33: 886-94), and thus, processes other than competence may be adversely affected in mecA-deficient cells. A second approach involved increasing the expression of ComS that would ostensibly release ComK from the MecA/ClpCP complex, protecting it from degradation and thereby enabling induction of the late competence genes. To employ this approach, *Bacillus licheniformis* strain SJ1904 xylA::comK+pComS (Example 14) was tested for competence development by transformation with plasmid and chromosomal DNAs. *Bacillus licheniformis* strain SJ1904 xylA::comK+pComS (a) contained a copy of the xylA::comK transcription unit integrated at the amyL gene locus, and (b) harbored a plasmid that contained a copy of the *Bacillus subtilis* comS gene (FIG. 22). As controls, a number of additional *Bacillus licheniformis* strains were tested in the same assay including the SJ1904 background strain, and strains that harbored only the xylA::comK expression unit, the pComS vector, or the pΔComS control plasmid (Example 14).

The following *Bacillus licheniformis* transformation hosts were spread from frozen glycerol stocks to obtain confluent growth, on appropriate selective medium, after overnight incubation: SJ1904 xylA::comK, SJ1904 xylA::comK+pComS, SJ1904+pComS, SJ1904+pΔComS, and SJ1904. Fifty milliliters of Spizizen I medium containing 2% xylose was added to 500 ml side-arm flasks. Next 5 ml Spizizen I medium with 2% xylose was added to the culture plates, the cells were collected by scraping with sterile spreaders and transferred into sterile tubes. Five hundred microliters from each 5 ml culture was added to a side-arm flask to obtain a Klett reading of 30. Cultures were incubated at 37° C., 250 rpm for 11 hours. Two hundred fifty microliters from each 11 hour culture plus 250 μl of Spizizen II medium containing 2% xylose and 2 mM EGTA were added to Falcon 2059 tubes. One microgram of transforming DNA, either plasmid or chromosomal DNA, was added to each tube; 10 mM Tris-0.1 mM EDTA (TE) buffer was used as a negative control. The tubes were incubated at 37° C. for chromosomal DNA and 34° C. for plasmid DNA, 250 rpm for 1 hour. Transformation reactions with chromosomal DNA were plated to TBAB plates containing 100 μg of spectinomycin per ml. Transformation reactions with plasmid DNA were plated on TBAB erythromycin/lincomycin plates. The plates were incubated at 37° C. for selection on spectinomycin and 34° C. for selection on plates containing erythromycin. Colonies were counted the following day to determine transformation efficiency.

The results in Table 4 show that *Bacillus licheniformis* recipient strains that harbored the plasmid-borne *Bacillus subtilis* comS gene (samples 2 and 3) gave approximately 20 to 45 transformants per plate with chromosomal DNA and 3 to 7 transformants per plate when using plasmid DNA under the conditions employed in this experiment. In contrast, strains that did not harbor the *Bacillus subtilis* comS gene gave only background levels of spectinomycin resistant colonies and no erythromycin resistant colonies. A combination of elevated comS and comK gene expression roughly doubled the transformation frequency in *Bacillus licheniformis*, although elevated expression of comK alone did not induce competence. PCR analysis of three independent erythromycin and kanamycin resistant colonies derived from pMDT131 transformation of the *Bacillus licheniformis* SJ1904 xylA::comK+pComS strain showed that all contained the integrated xylA::comK expression cassette, the pComS plasmid, and the pE194-based plasmid, confirming that they were bona fide transformants.

TABLE 3

Competence-mediated transformation of *Bacillus licheniformis* SJ194 derivatives with plasmid and chromosomal DNA
Colonies per plate

| Sample | Recipient | MDT232 chromo-somal DNA* | No chromosomal DNA control*** | pMDT131 plasmid DNA** | No pMDT131 plasmid DNA control*** |
|---|---|---|---|---|---|
| 1 | xylA:: comK | 1 | 3 | 0 | 0 |
| 2 | xylA:: comK + pComS | 45 | 1 | 7 | 0 |
| 3 | pComS | 19 | 0 | 3 | 0 |
| 4 | pΔComS | 2 | 1 | 0 | 0 |
| 5 | SJ1904 | 2 | 1 | 0 | 0 |

*Average of three plates
**Average of four plates
***No DNA controls were plated on medium with spectinomycin [a low level of spontaneous spectinomycin resistant mutants is possible with spectinomycin selection (Kimura et aL, 1973, *Mol. Gen. Genet.* 124: 17-115)].

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method of obtaining a *Bacillus licheniformis* transformant, comprising:

(a) transforming an exogenous DNA into a *Bacillus licheniformis* host cell made competent by at least one copy of an introduced first nucleic acid construct comprising a promoter region operably linked to a polynucleotide encoding a ComS polypeptide, wherein the polynucleotide encoding the ComS polypeptide is foreign to the *Bacillus licheniformis* host cell that was non-competent prior to introduction of the first nucleic acid construct; and and wherein the ComS polypeptide comprises an amino acid sequence having at least 90% sequence identity with SEQ ID NO: 4; and (b) isolating a transformant of the *Bacillus licheniformis* host cell comprising the DNA.

2. The method of claim 1, wherein the ComS polypeptide comprises an amino acid sequence having at least 95% sequence identity with SEQ ID NO: 4.

3. The method of claim 1, wherein the ComS polypeptide comprises an amino acid sequence having at least 97% sequence identity with SEQ ID NO: 4.

4. The method of claim 1, wherein the ComS polypeptide comprises the amino acid sequence of SEQ ID NO: 4.

5. The method of claim 1, wherein the polynucleotide encoding the ComS polypeptide comprises the nucleotide sequence of SEQ ID NO: 5.

6. The method of claim 1, wherein the competent *Bacillus licheniformis* host cell further comprises at least one copy of an introduced second nucleic acid construct comprising a promoter region operably linked to a polynucleotide encoding a ComK polypeptide.

7. The method of claim 6, wherein the ComK polypeptide comprises the amino acid sequence of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50.

8. The method of claim 6, wherein the ComK polypeptide comprises the amino acid sequence of SEQ ID NO: 14.

9. A method of obtaining a competent *Bacillus licheniformis* host cell, comprising:

(a) introducing into a non-competent *Bacillus licheniformis* host cell at least one copy of a first nucleic acid construct comprising a promoter region operably linked to a polynucleotide encoding a ComS polypeptide, wherein the polynucleotide encoding the ComS polypeptide is foreign to the *Bacillus licheniformis* host cell; and wherein the ComS polypeptide comprises an amino acid sequence having at least 90% sequence identity with SEQ ID NO: 4; and (b) isolating a competent *Bacillus licheniformis* host cell comprising the polynucleotide encoding the ComS polypeptide.

10. The method of claim 9, wherein the competent *Bacillus licheniformis* host cell further comprises at least one copy of an introduced second nucleic acid construct comprising a promoter region operably linked to a polynucleotide encoding a ComK polypeptide.

11. The method of claim 10, wherein the ComK polypeptide comprises the amino acid sequence of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50.

12. The method of claim 10, wherein the ComK polypeptide comprises the amino acid sequence of SEQ ID NO: 14.

13. The method of claim 9, wherein the ComS polypeptide comprises an amino acid sequence having at least 95% sequence identity with SEQ ID NO: 4.

14. The method of claim 9, wherein the ComS polypeptide comprises an amino acid sequence having at least 97% sequence identity with SEQ ID NO: 4.

15. The method of claim 9, wherein the ComS polypeptide comprises the amino acid sequence of SEQ ID NO: 4.

16. The method of claim 9, wherein the polynucleotide encoding the ComS polypeptide comprises the nucleotide sequence of SEQ ID NO: 5.

17. A competent *Bacillus licheniformis* host cell comprising at least one copy of an introduced first nucleic acid construct comprising a promoter region operably linked to a polynucleotide encoding a ComS polypeptide, wherein the polynucleotide encoding the ComS polypeptide is foreign to the *Bacillus licheniformis* host cell that was non-competent prior to introduction of the first nucleic acid construct, and wherein the ComS polypeptide comprises an amino acid sequence having at least 90% sequence identity with SEQ ID NO: 4.

18. The competent *Bacillus licheniformis* host cell of claim 17, wherein the competent *Bacillus licheniformis* host cell further comprises at least one copy of an introduced second nucleic acid construct comprising a promoter region operably linked to a polynucleotide encoding a ComK polypeptide.

19. The competent *Bacillus licheniformis* host cell of claim 18, wherein the ComK polypeptide comprises the amino acid sequence of SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, or SEQ ID NO: 50.

20. The competent *Bacillus licheniformis* host cell of claim 18, wherein the ComK polypeptide comprises the amino acid sequence of SEQ ID NO: 14.

21. The competent *Bacillus licheniformis* host cell of claim 17, which has been transformed with an exogenous DNA.

22. A method of producing a biological substance, comprising:

(a) cultivating the *Bacillus licheniformis* host cell of claim 17 transformed with an exogenous DNA encoding or involved in the expression of a substance having biological activity under conditions conducive for production of the substance; and (b) recovering the substance having biological activity.

23. A method of producing a mutant of a *Bacillus licheniformis* cell, comprising:

(a) transforming into the *Bacillus licheniformis* cell of claim 17 an exogenous DNA capable of modifying a gene encoding a polypeptide, which results in a mutant cell producing less of the polypeptide; and (b) isolating the mutant cell.

24. The competent *Bacillus licheniformis* host cell of claim 17, wherein the ComS polypeptide comprises an amino acid sequence having at least 95% sequence identity with SEQ ID NO: 4.

25. The competent *Bacillus licheniformis* host cell of claim 17, wherein the ComS polypeptide comprises an amino acid sequence having at least 97% sequence identity with SEQ ID NO: 4.

26. The competent *Bacillus licheniformis* host cell of claim 17, wherein the ComS polypeptide comprises the amino acid sequence of SEQ ID NO: 4.

27. The competent *Bacillus licheniformis* host cell of claim 17, wherein the polynucleotide encoding the ComS polypeptide comprises the nucleotide sequence of SEQ ID NO: 5.

* * * * *